(12) United States Patent
Sung et al.

(10) Patent No.: US 11,466,286 B2
(45) Date of Patent: Oct. 11, 2022

(54) METHODS AND COMPOSITIONS FOR CONFERRING AND/OR ENHANCING HERBICIDE TOLERANCE USING PROTOPORPHYRINOGEN OXIDASE OR VARIANT THEREOF

(71) Applicant: FarmHannong Co., Ltd., Seoul (KR)

(72) Inventors: Soon-Kee Sung, Daejeon (KR); Joonseon Yoon, Daejeon (KR); Yunjung Han, Daejeon (KR); Young Ock Ahn, Daejeon (KR); Joonghyuk Park, Daejeon (KR); Myoung-Ki Hong, Daejeon (KR)

(73) Assignee: FARMHANNONG CO., LTD., Seoul (KR)

( * ) Notice: Subject to any disclaimer, the term of this patent is extended or adjusted under 35 U.S.C. 154(b) by 47 days.

(21) Appl. No.: 17/067,999

(22) Filed: Oct. 12, 2020

(65) Prior Publication Data

US 2021/0095305 A1    Apr. 1, 2021

Related U.S. Application Data

(62) Division of application No. 16/307,680, filed as application No. PCT/KR2017/006275 on Jun. 15, 2017, now Pat. No. 10,844,395.

(30) Foreign Application Priority Data

Jun. 16, 2016  (KR) .................. 10-2016-0075358

(51) Int. Cl.
*C12N 15/82* (2006.01)
*C07K 14/195* (2006.01)

(52) U.S. Cl.
CPC ........ *C12N 15/8275* (2013.01); *C07K 14/195* (2013.01); *C12N 15/8277* (2013.01); *C12Y 103/03004* (2013.01)

(58) Field of Classification Search
CPC .................................................. C12N 15/8274
See application file for complete search history.

(56) References Cited

U.S. PATENT DOCUMENTS 10,308,953 B2 *   6/2019   Aponte .............. C12N 15/8274

* cited by examiner

*Primary Examiner* — Weihua Fan
(74) *Attorney, Agent, or Firm* — Lex IP Meister, PLLC

(57) ABSTRACT

Provided is technology for conferring enhanced herbicide tolerance and/or enhancing herbicide tolerance of plants and/or algae using a protoporphyrinogen oxidase derived from prokaryotes or its amino acid variants.

21 Claims, 41 Drawing Sheets

Specification includes a Sequence Listing.

[Fig. 1]
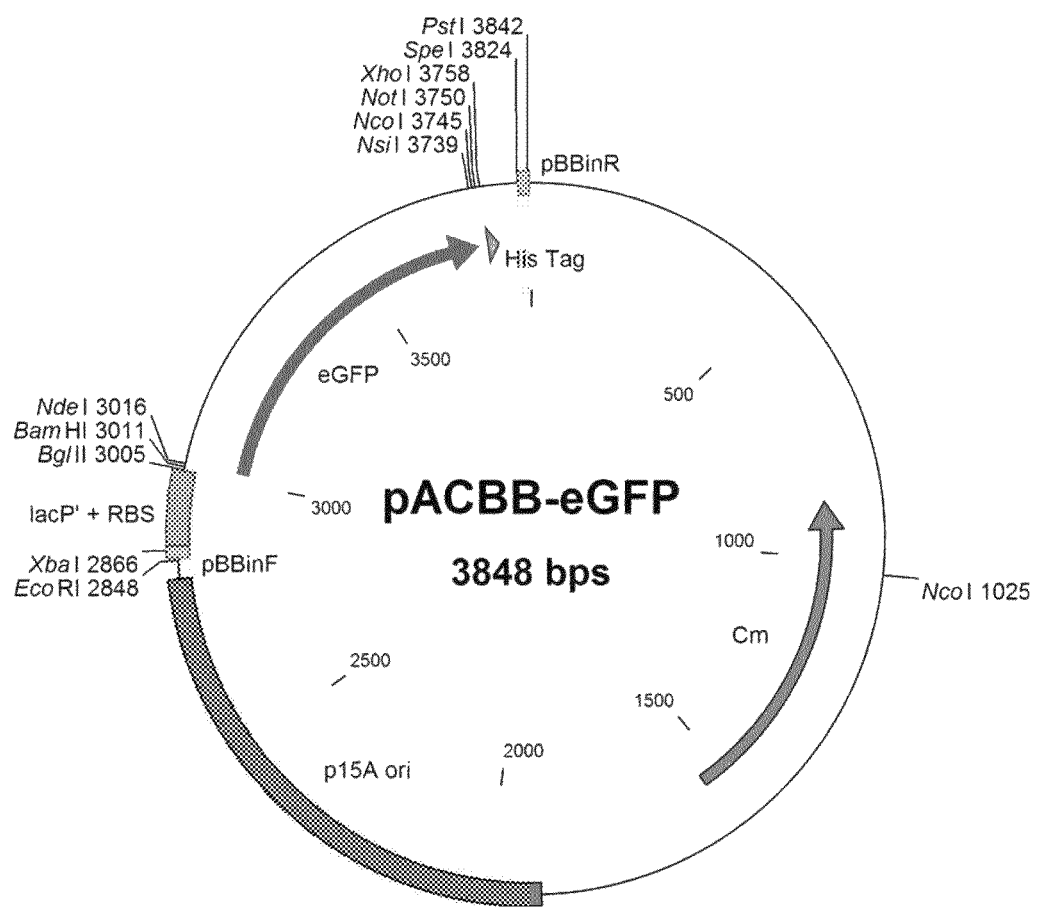

[Fig. 2]
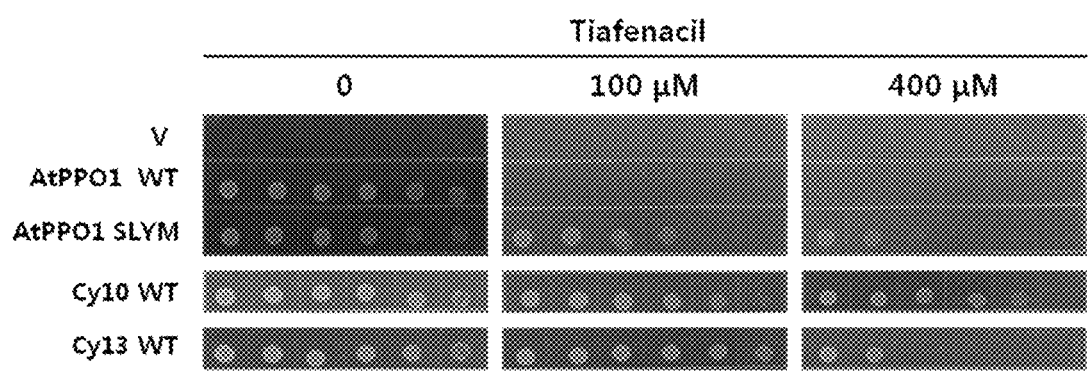

[Fig. 3]
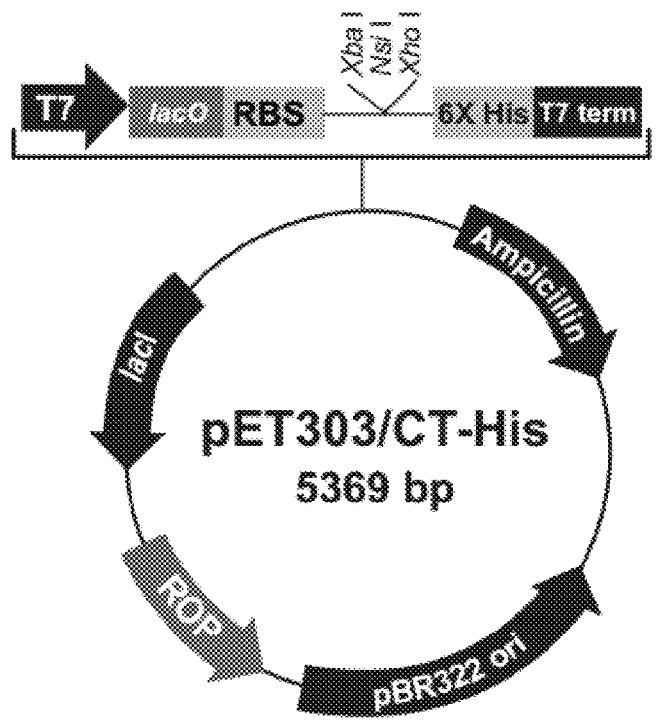
Comments for pET303 CT-His
5369 nucleotides
T7 promoter: bases 20-36
T7 promoter priming site: bases 20-39
lac operator (lacO): bases 39-63
Ribosome binding site (RBS): bases 95-100
6X His Tag: bases 119-136
T7 reverse priming site: bases 186-206
T7 transcription termination region: bases 147-277
F1 origin: bases 287-742
*bla* promoter: bases 775-879
Ampicillin (*bla*) resistance gene: bases 874-1734
pBR322 origin: bases 1945-2678 (c)
*ROP* ORF: bases 2920-3011 (c)
*lacI* ORF: bases 3914-5032 (c)

[Fig. 4]
Vector for Fusion Protein of PPO and MBP(Maltose binding protein)
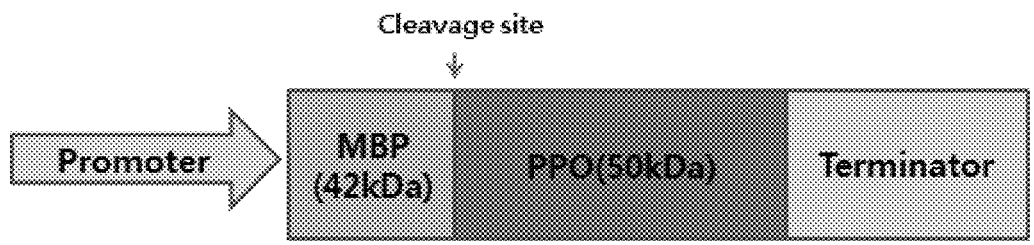
[Fig. 5]
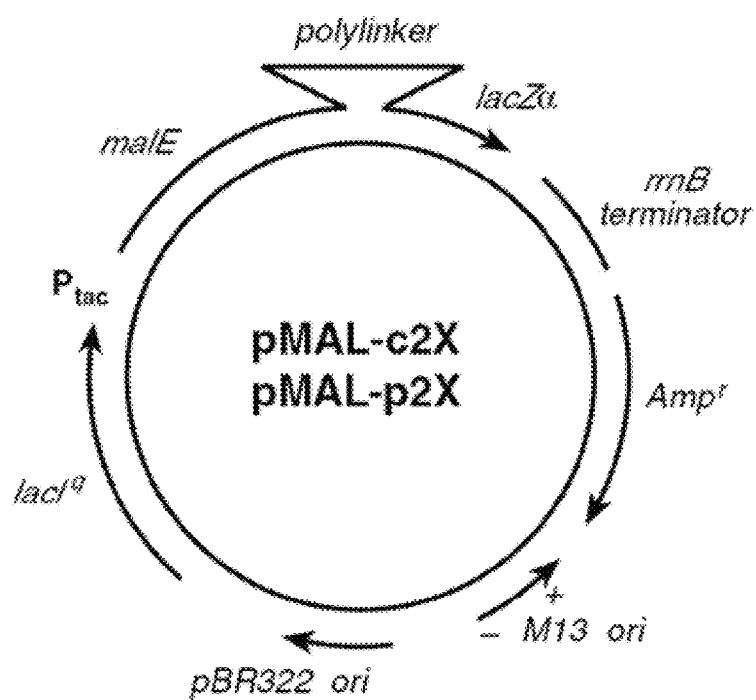

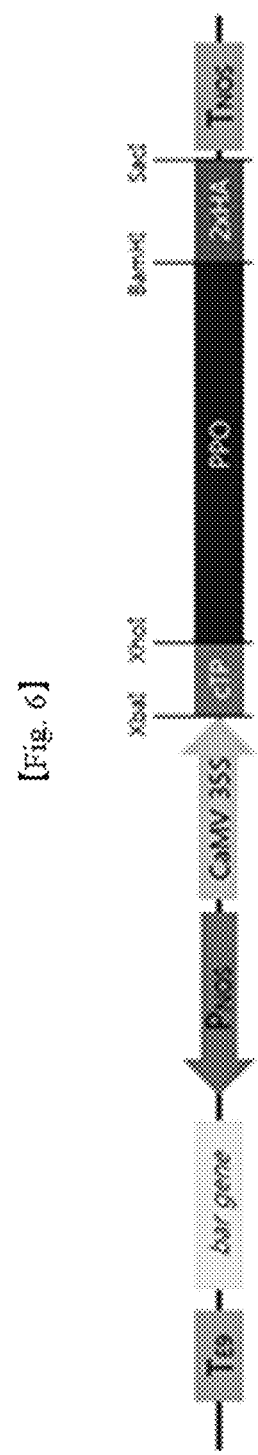
[Fig. 6]

[Fig. 7]
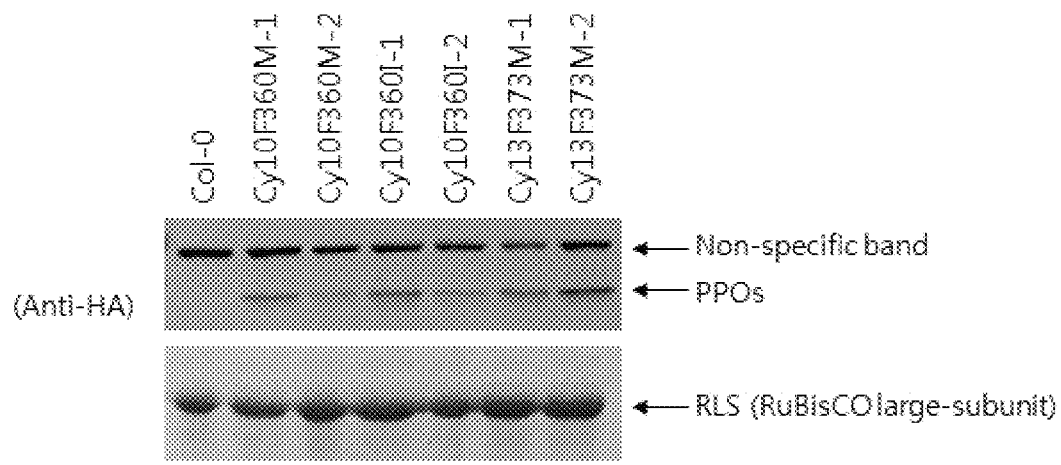
[Fig. 8]
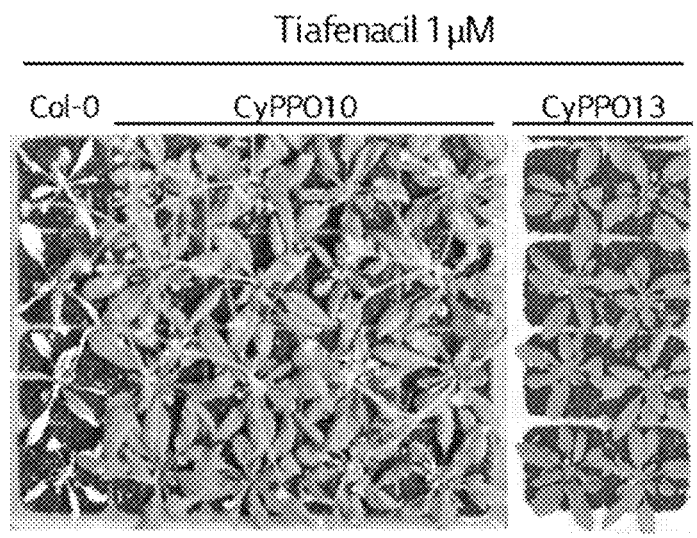

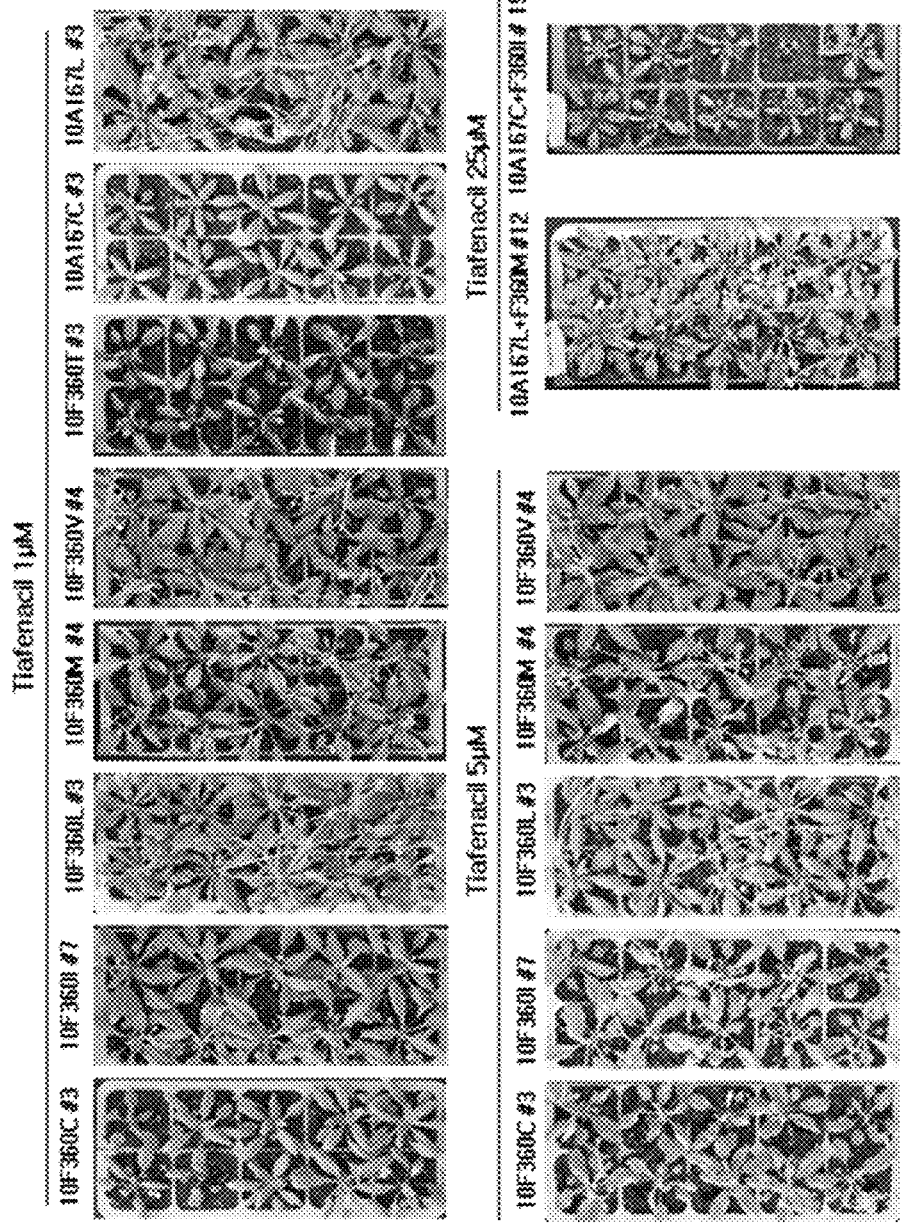

[Fig. 10]
Tiafenacil 1μM
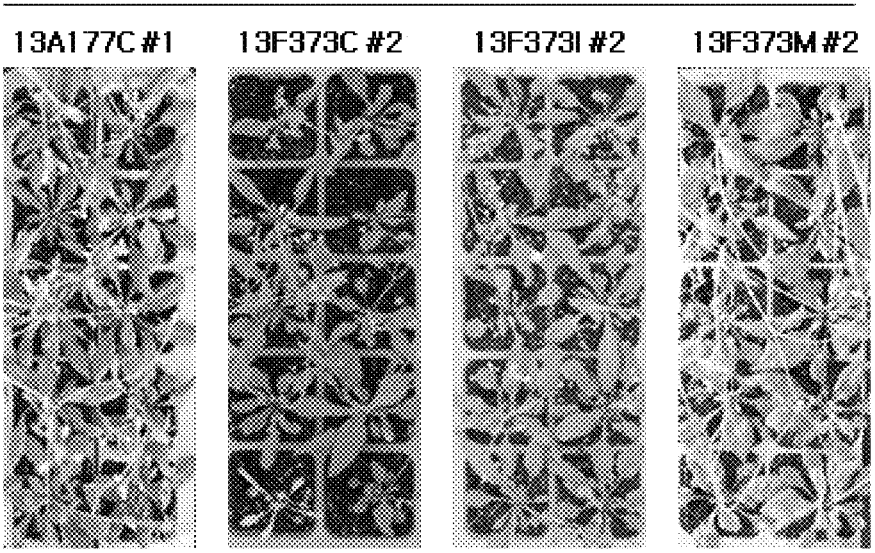
Tiafenacil 10μM
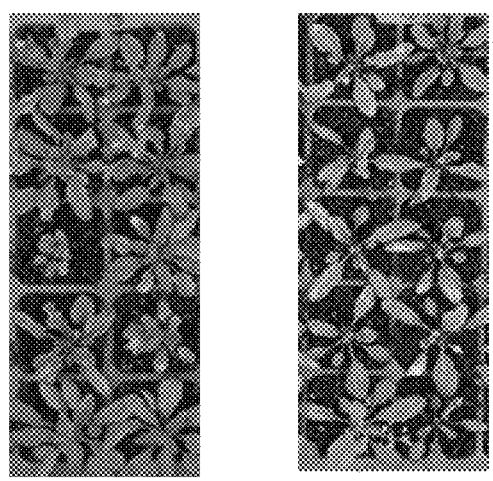

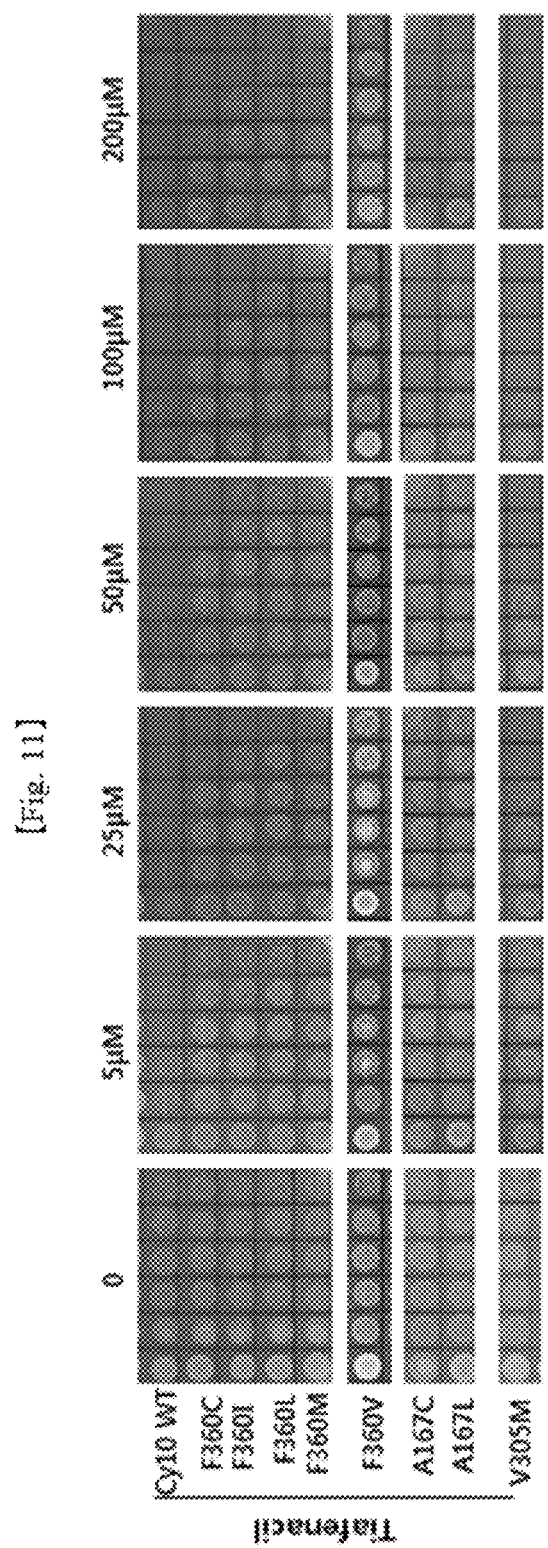
[Fig. 11]

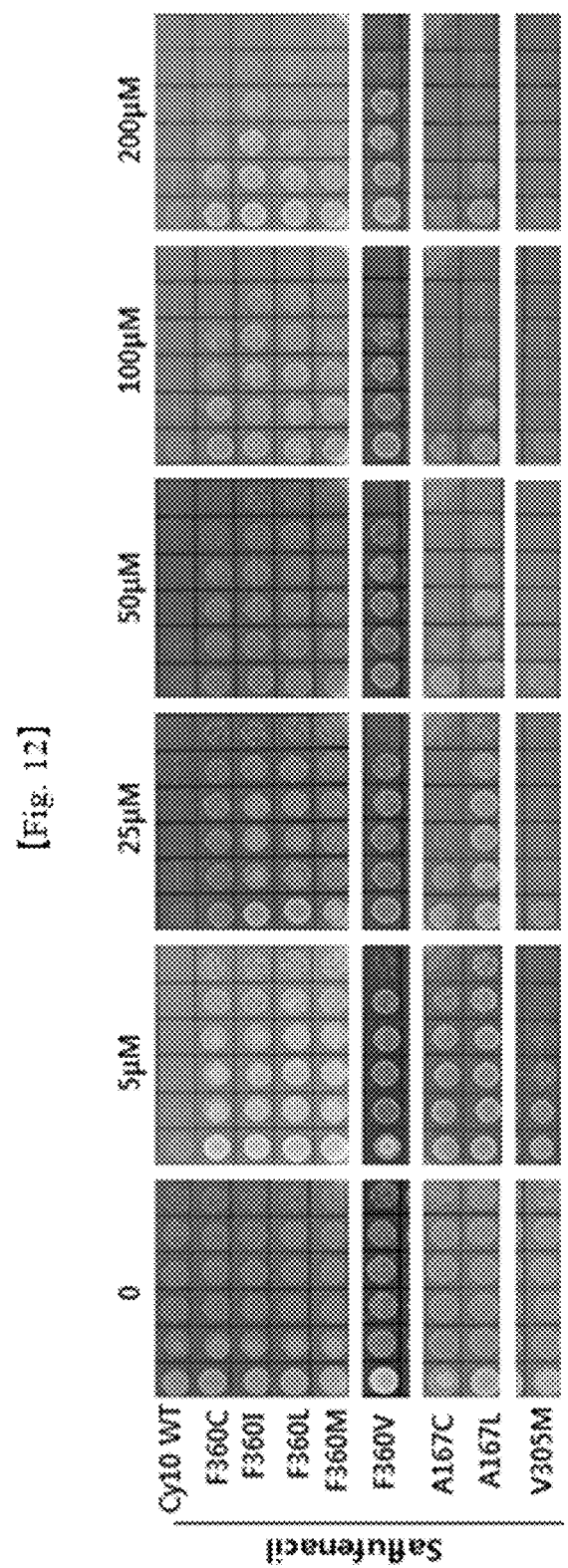
[Fig. 12]

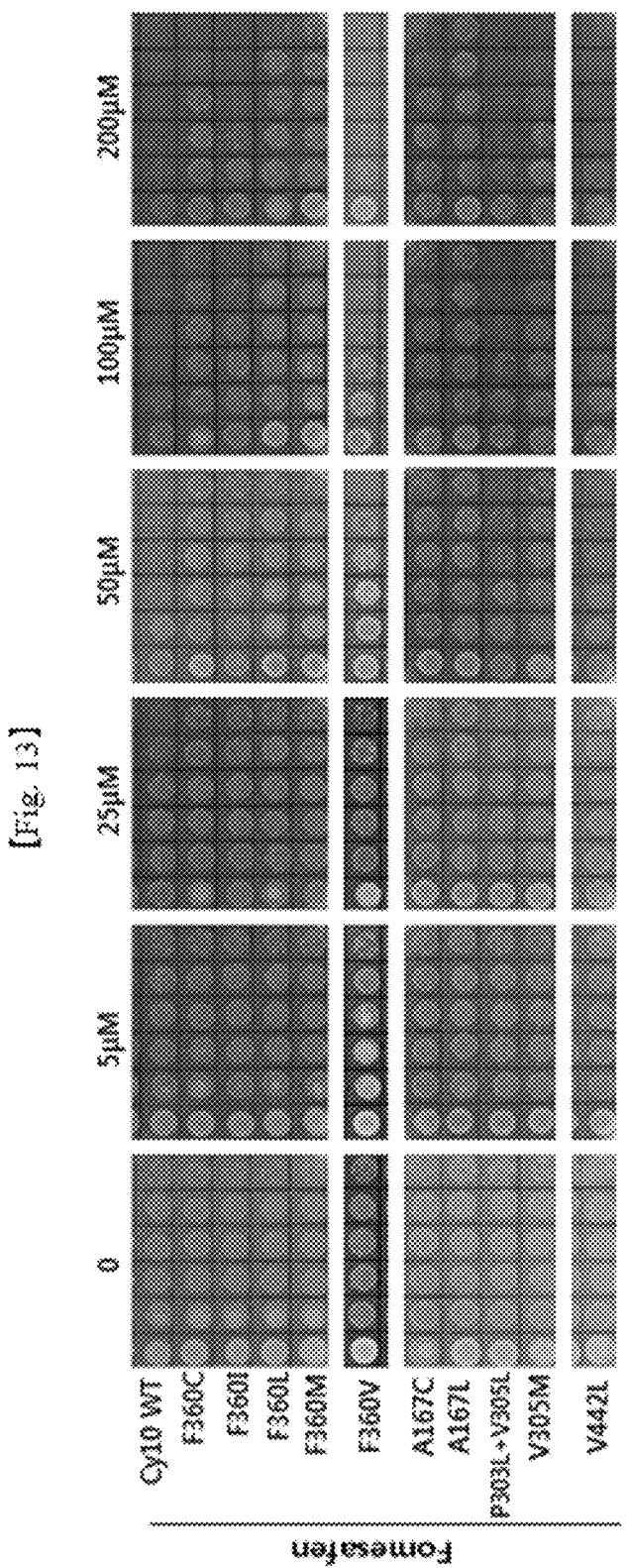
[Fig. 13]

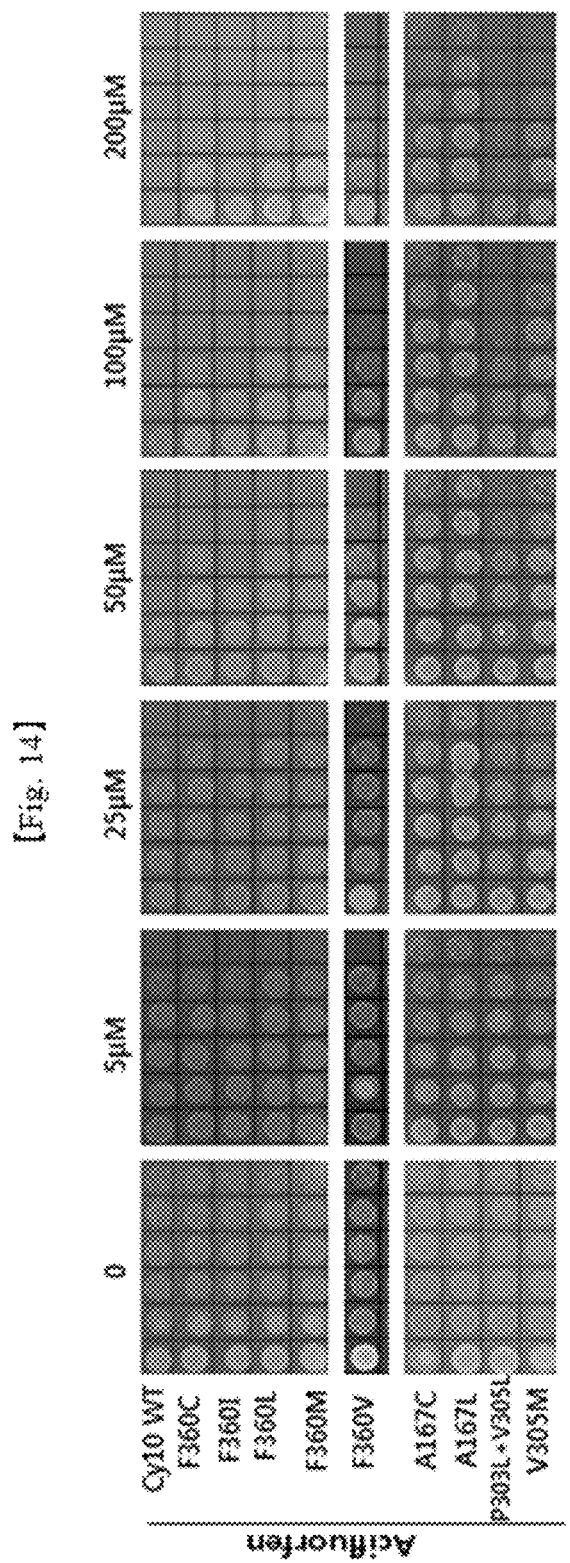
[Fig. 14]

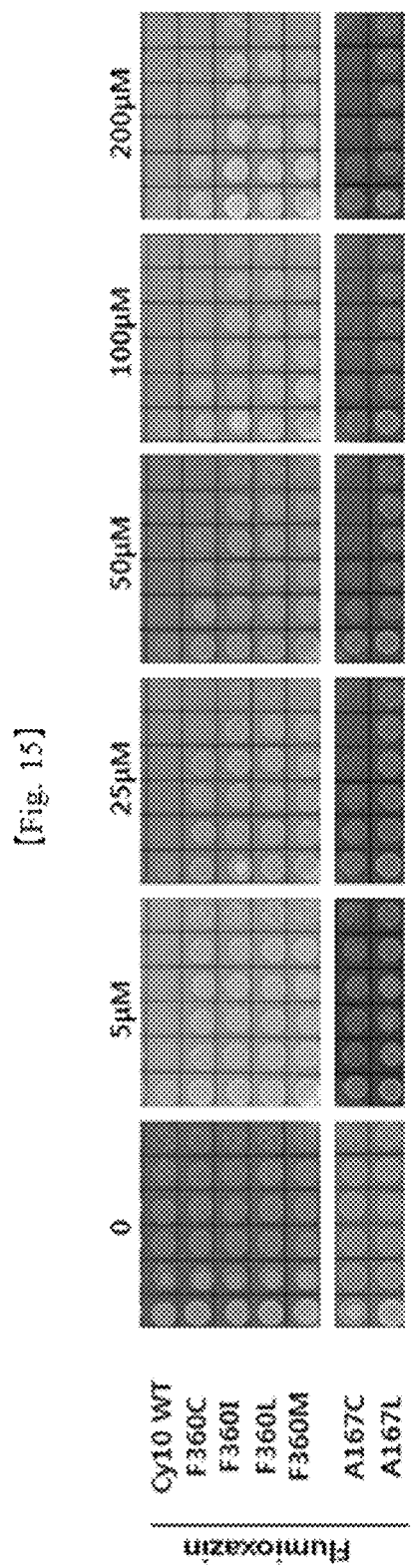
[Fig. 15]

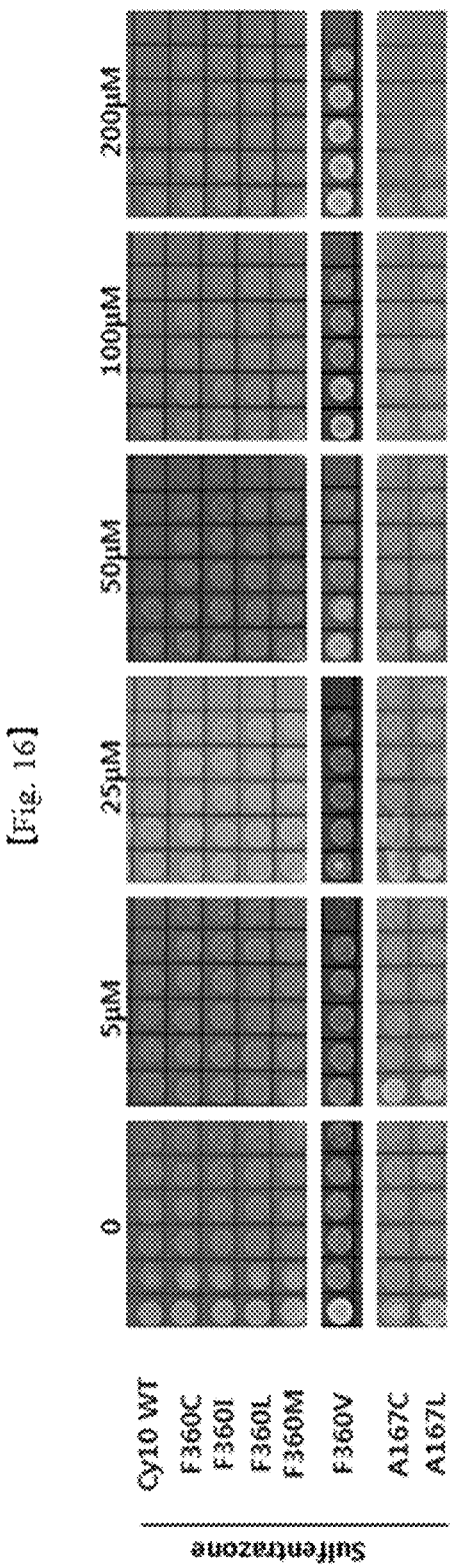
[Fig. 16]

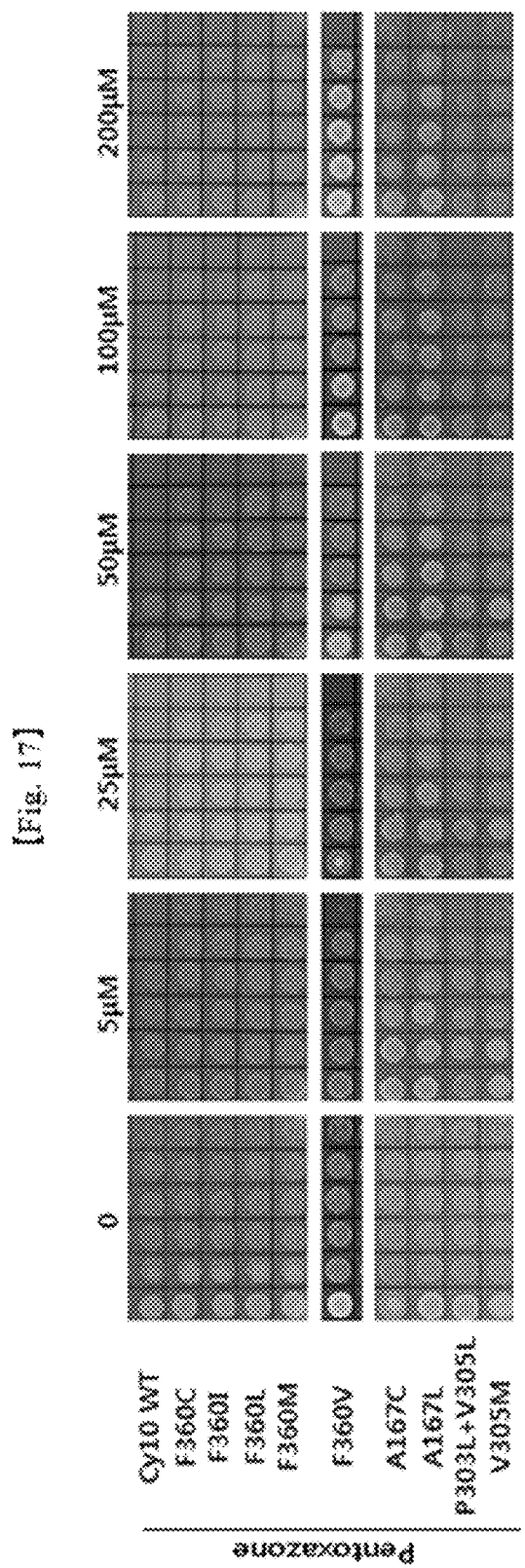

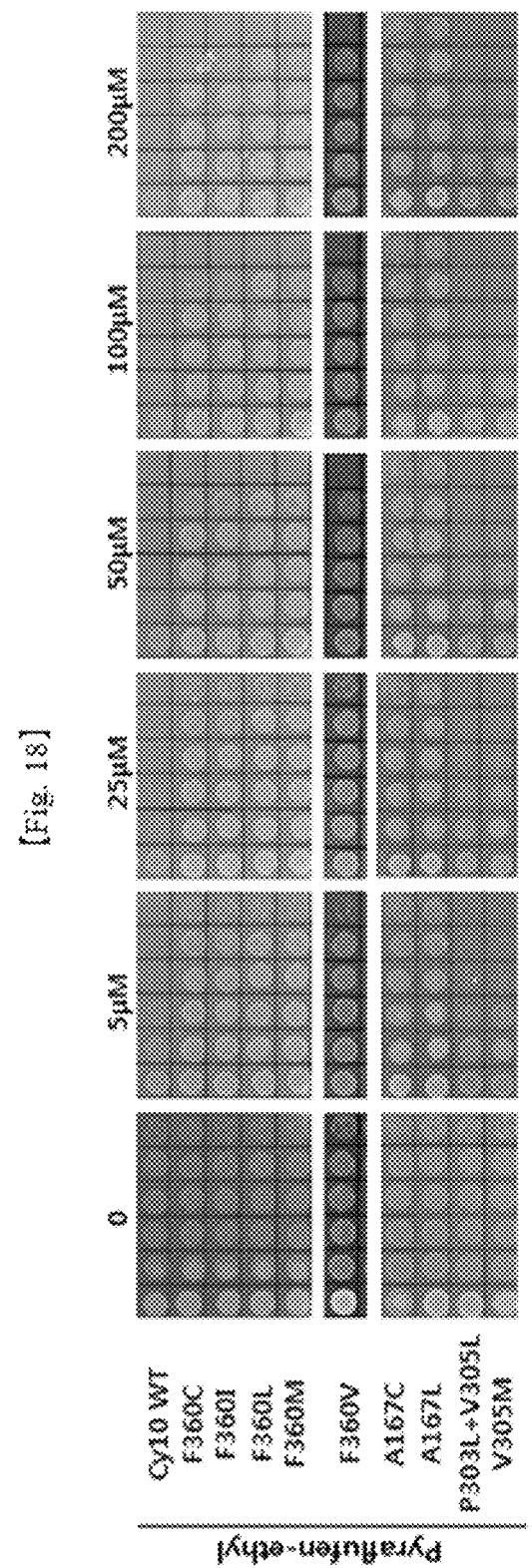

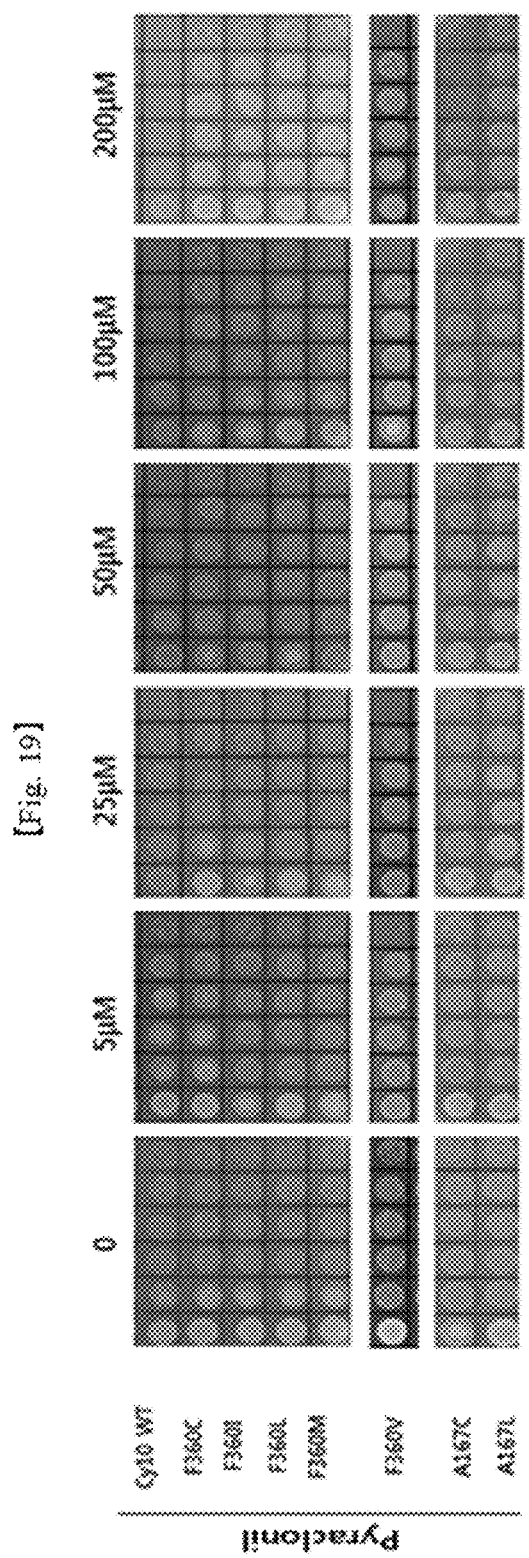
[Fig. 19]

[Fig. 20]
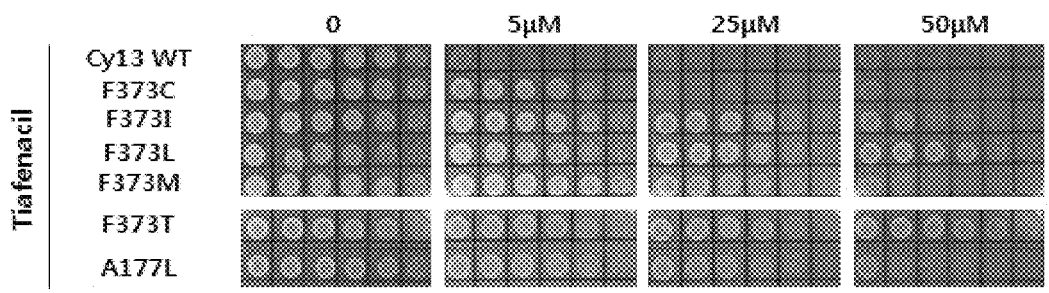
[Fig. 21]
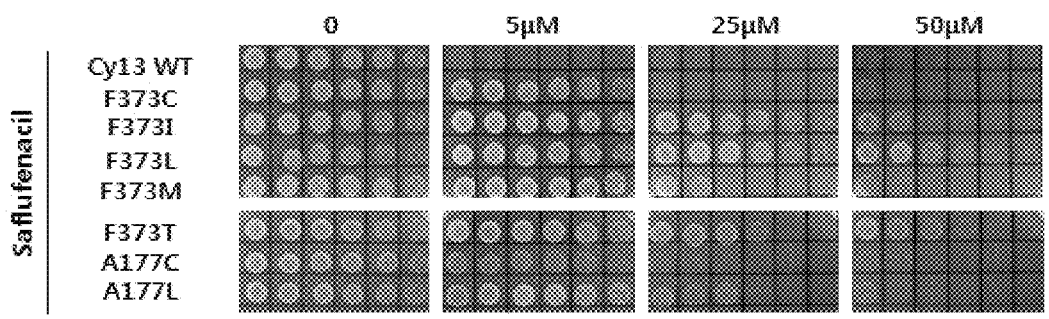

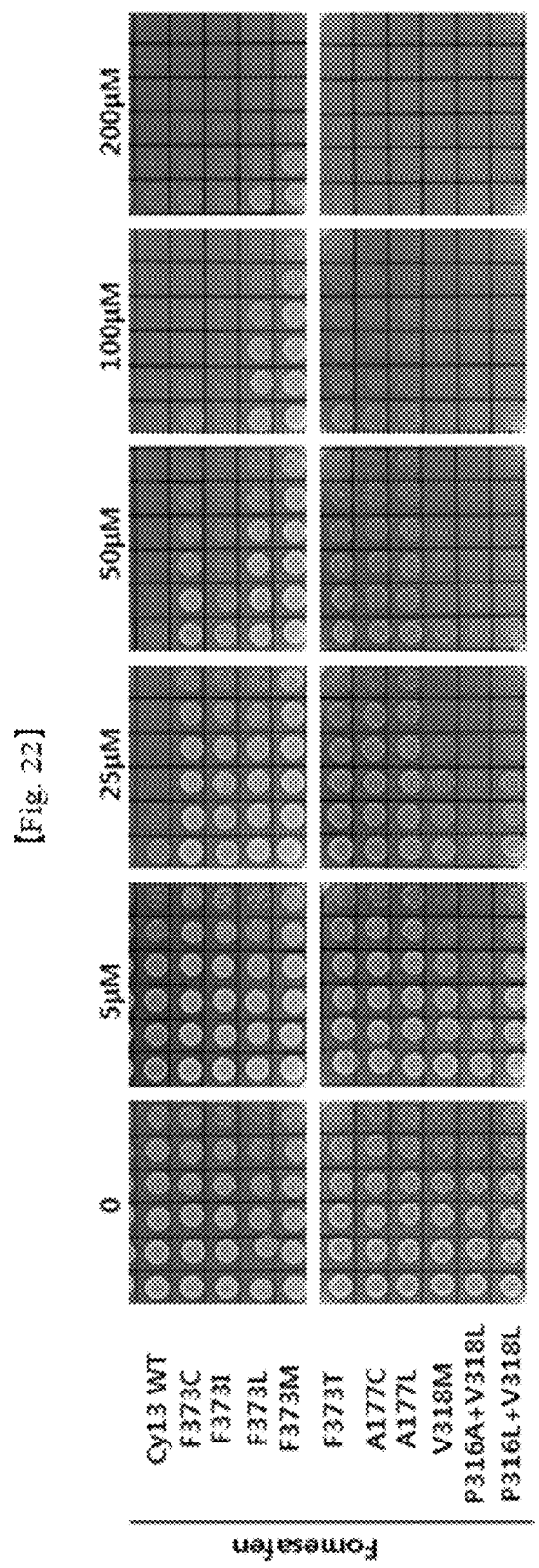

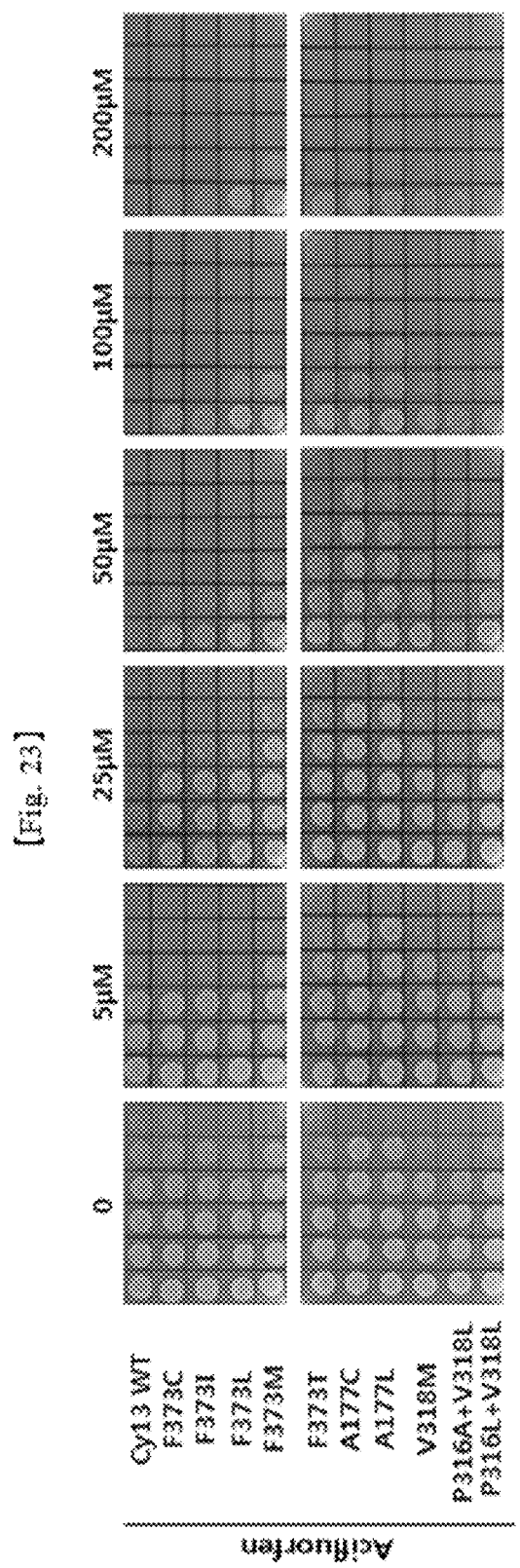
[Fig. 23]

[Fig. 24]
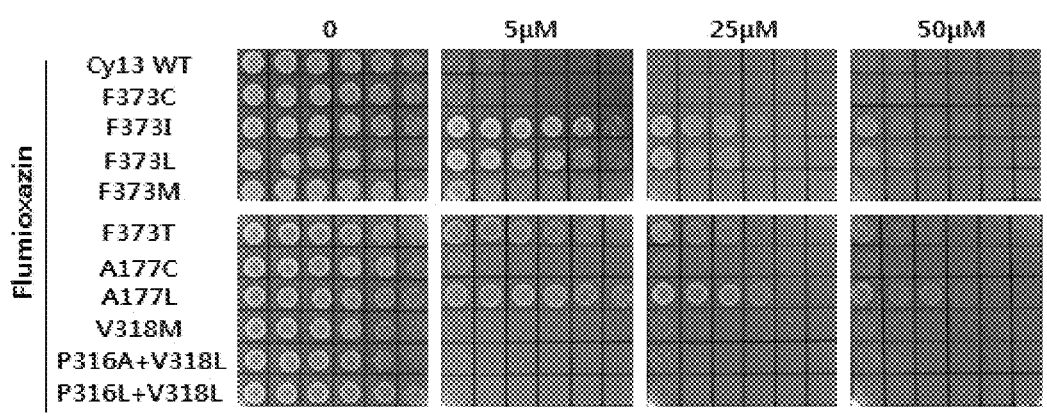

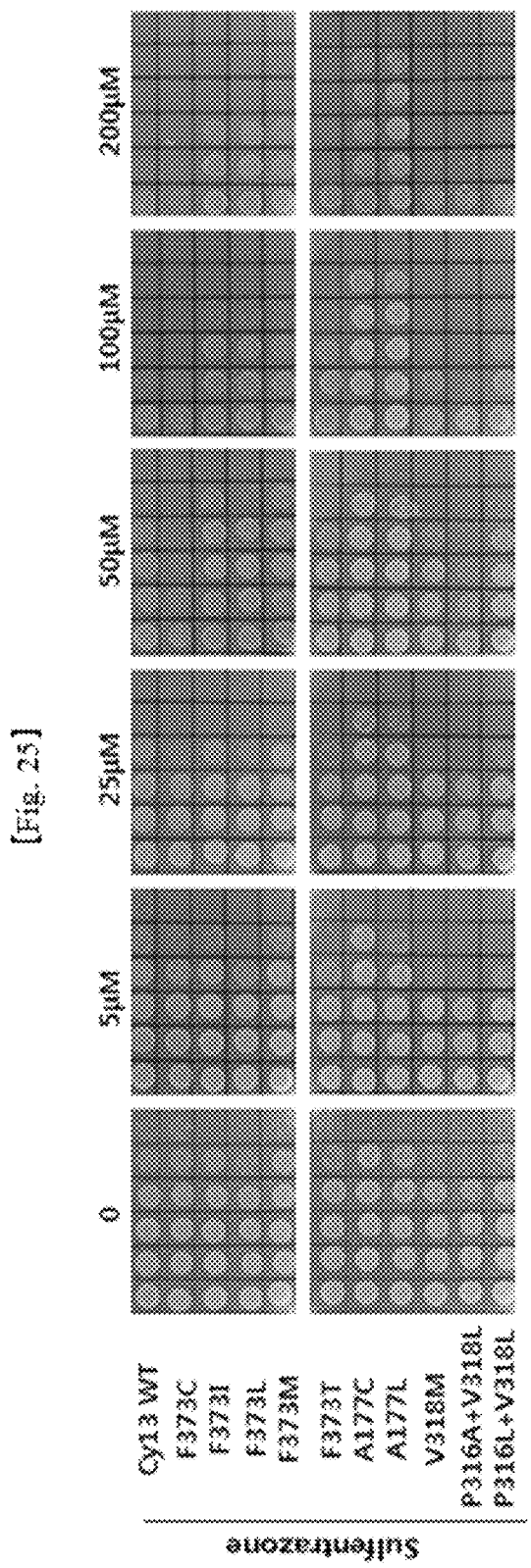
[Fig. 25]

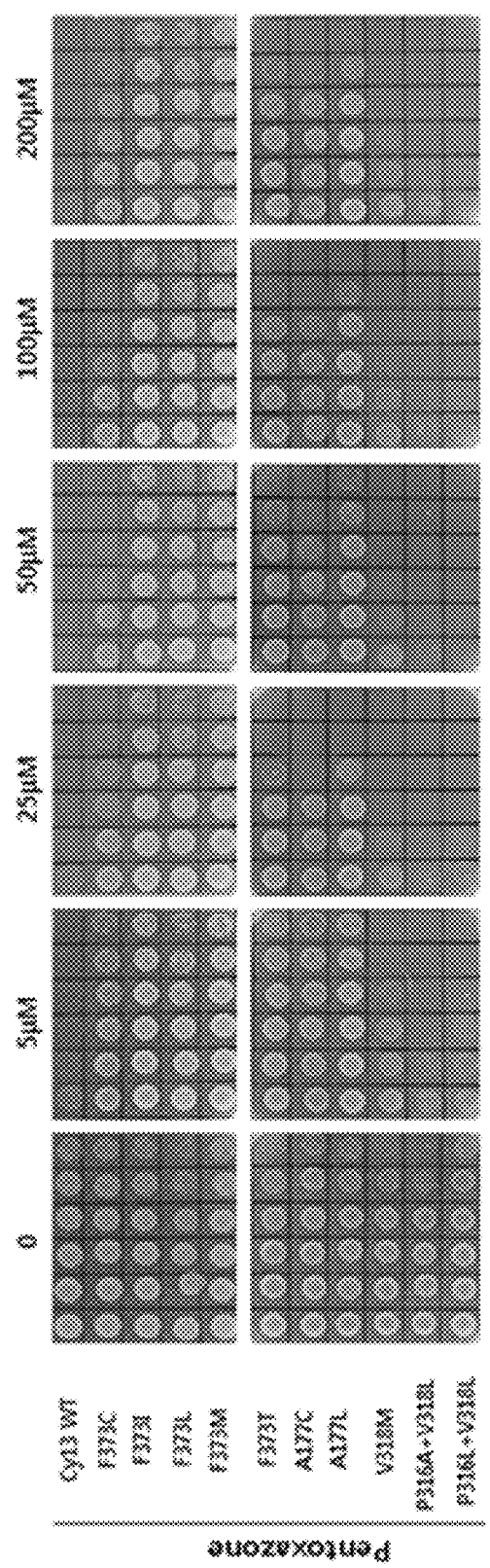

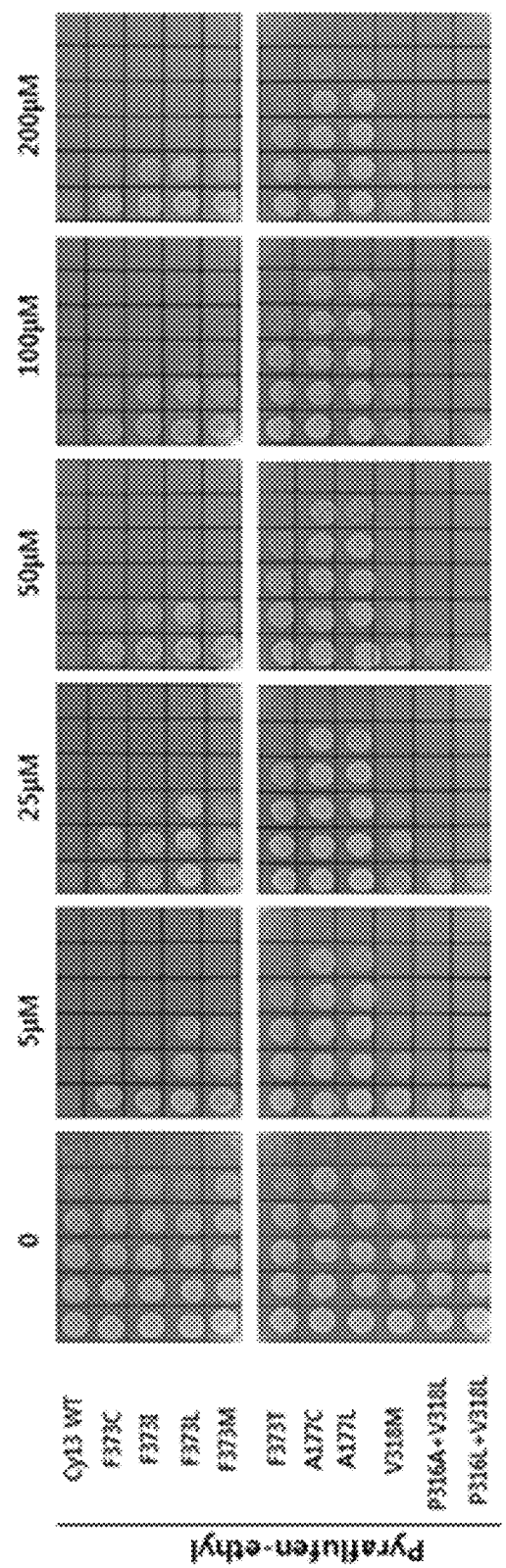
[Fig. 27]

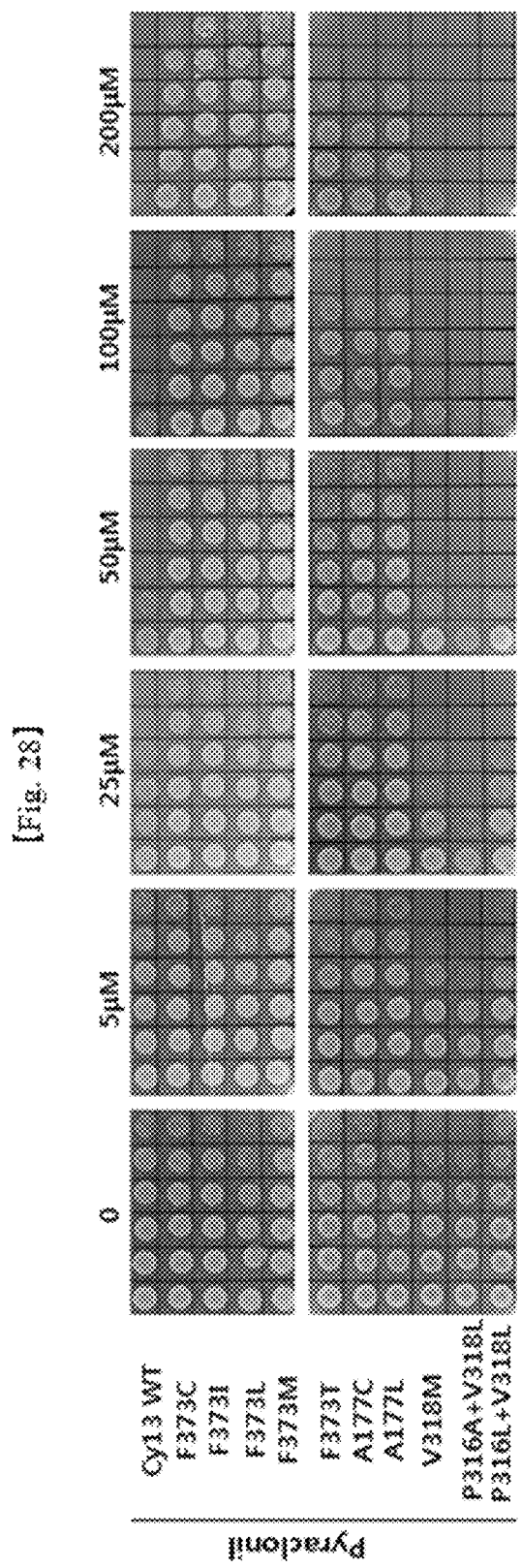
[Fig. 28]

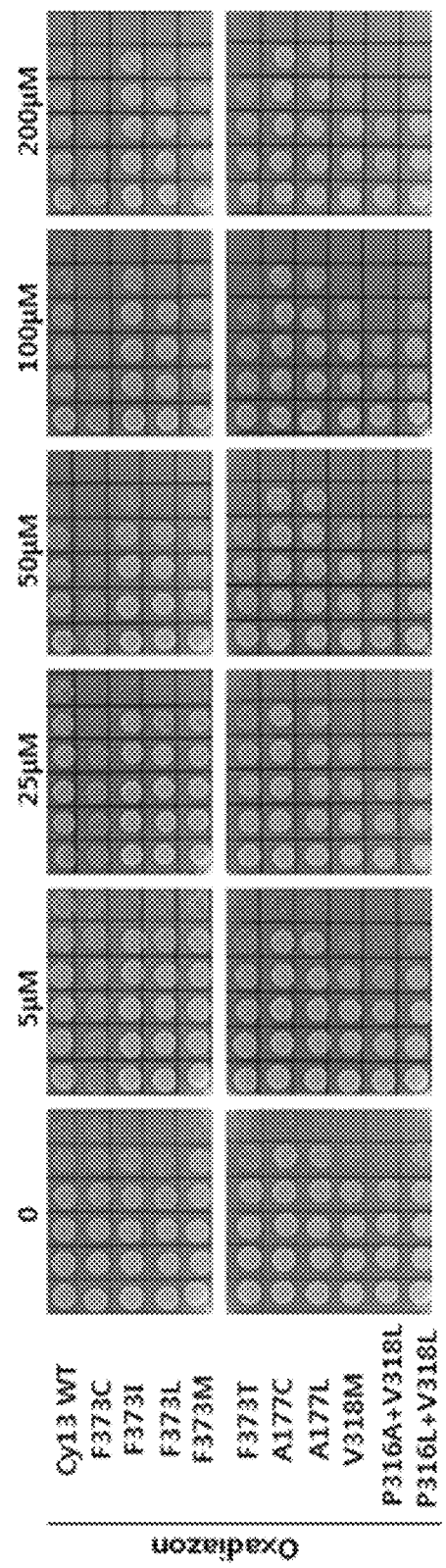

[Fig. 30]
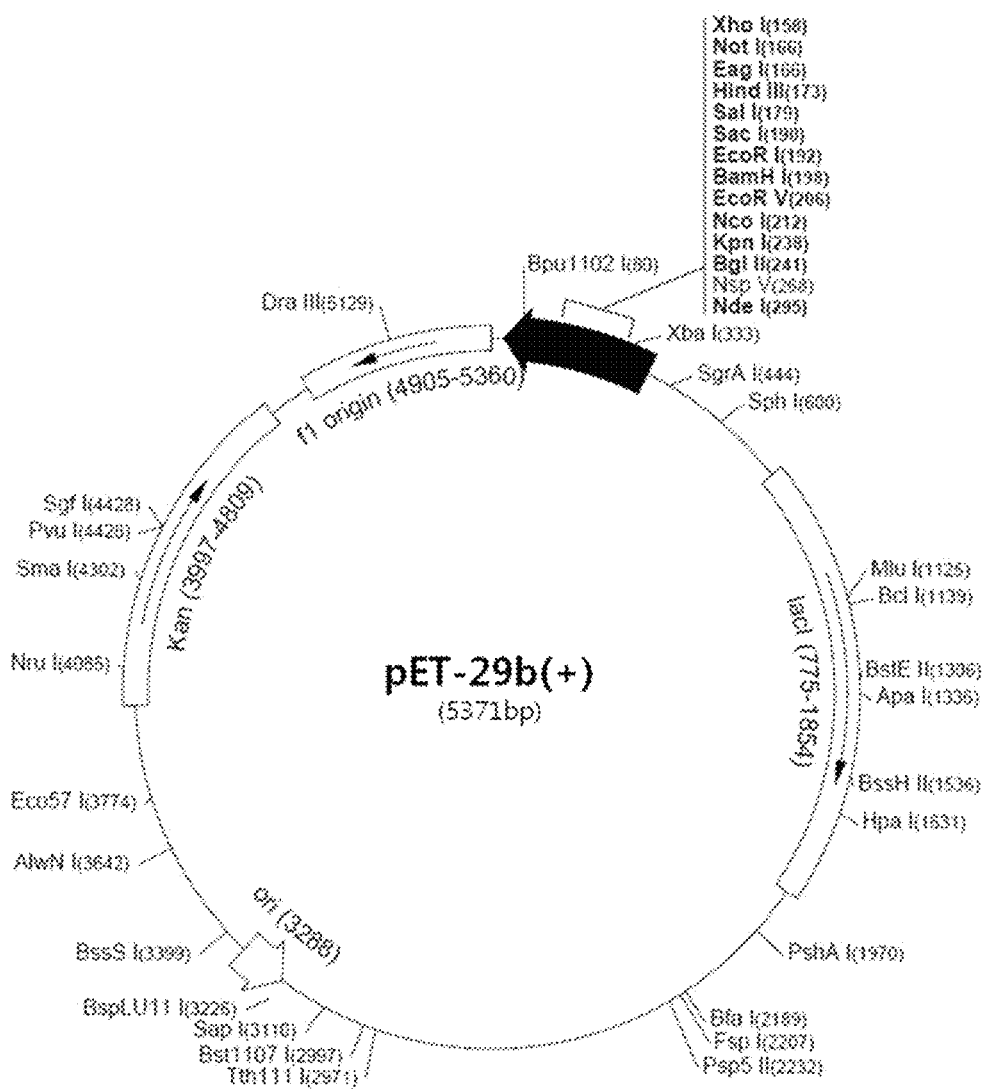

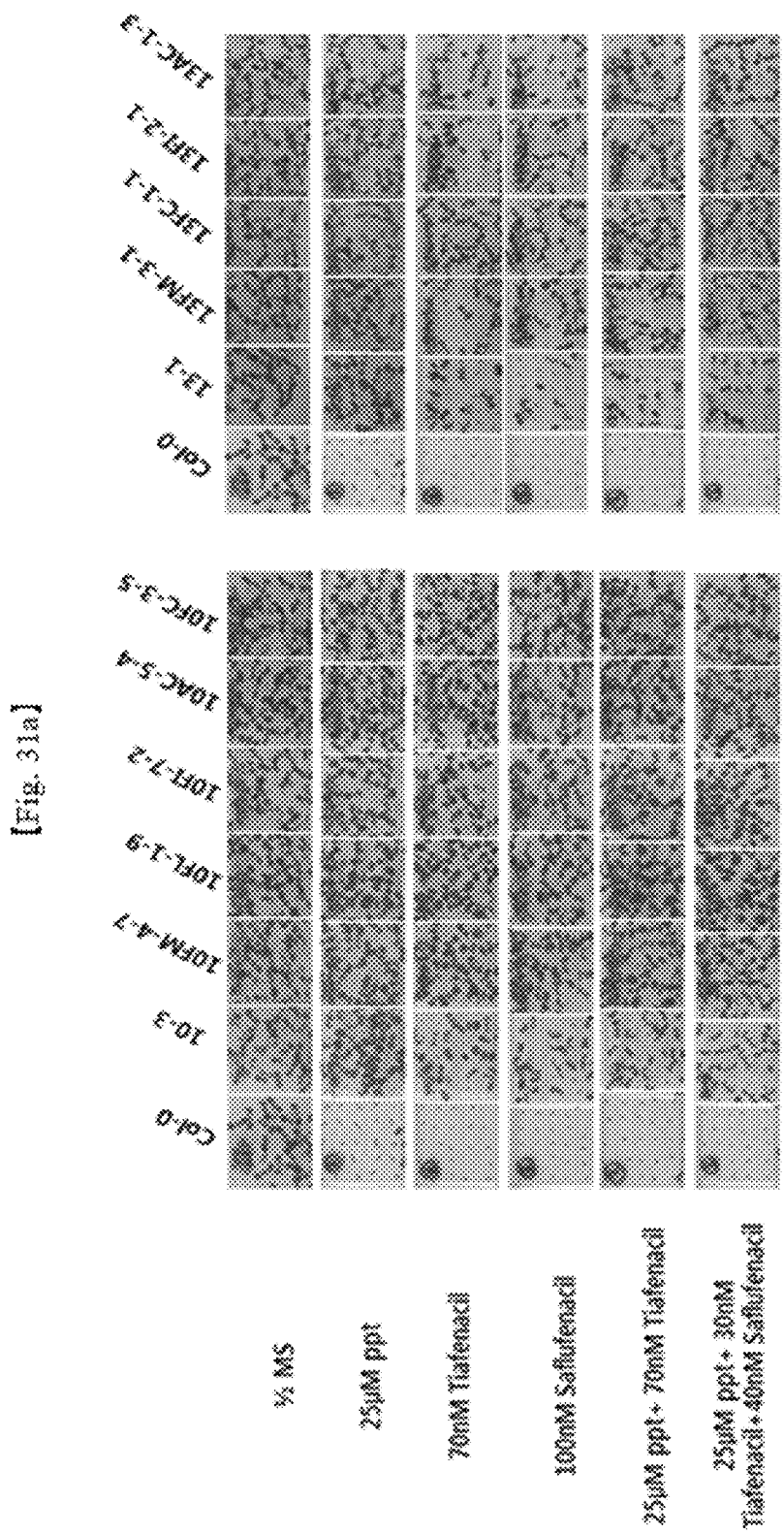

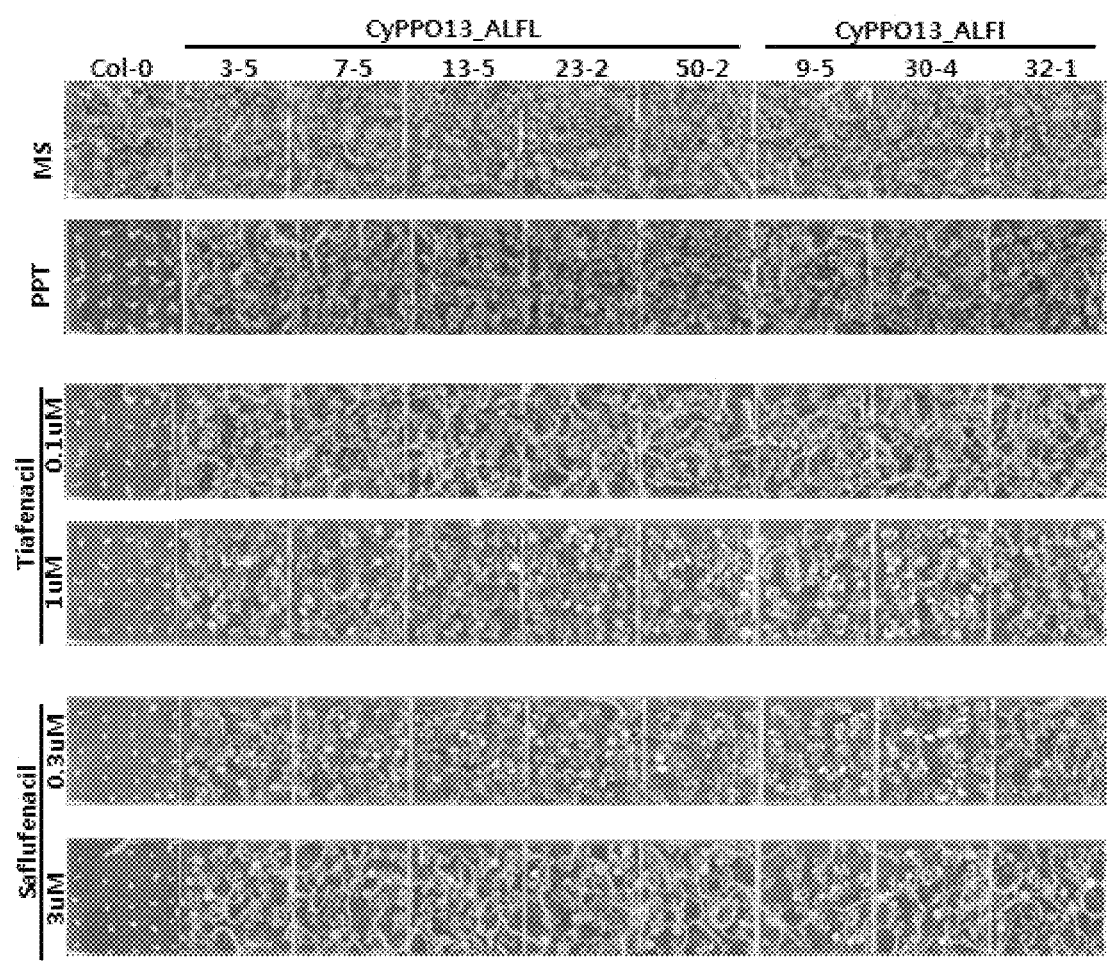
[Fig. 31b]

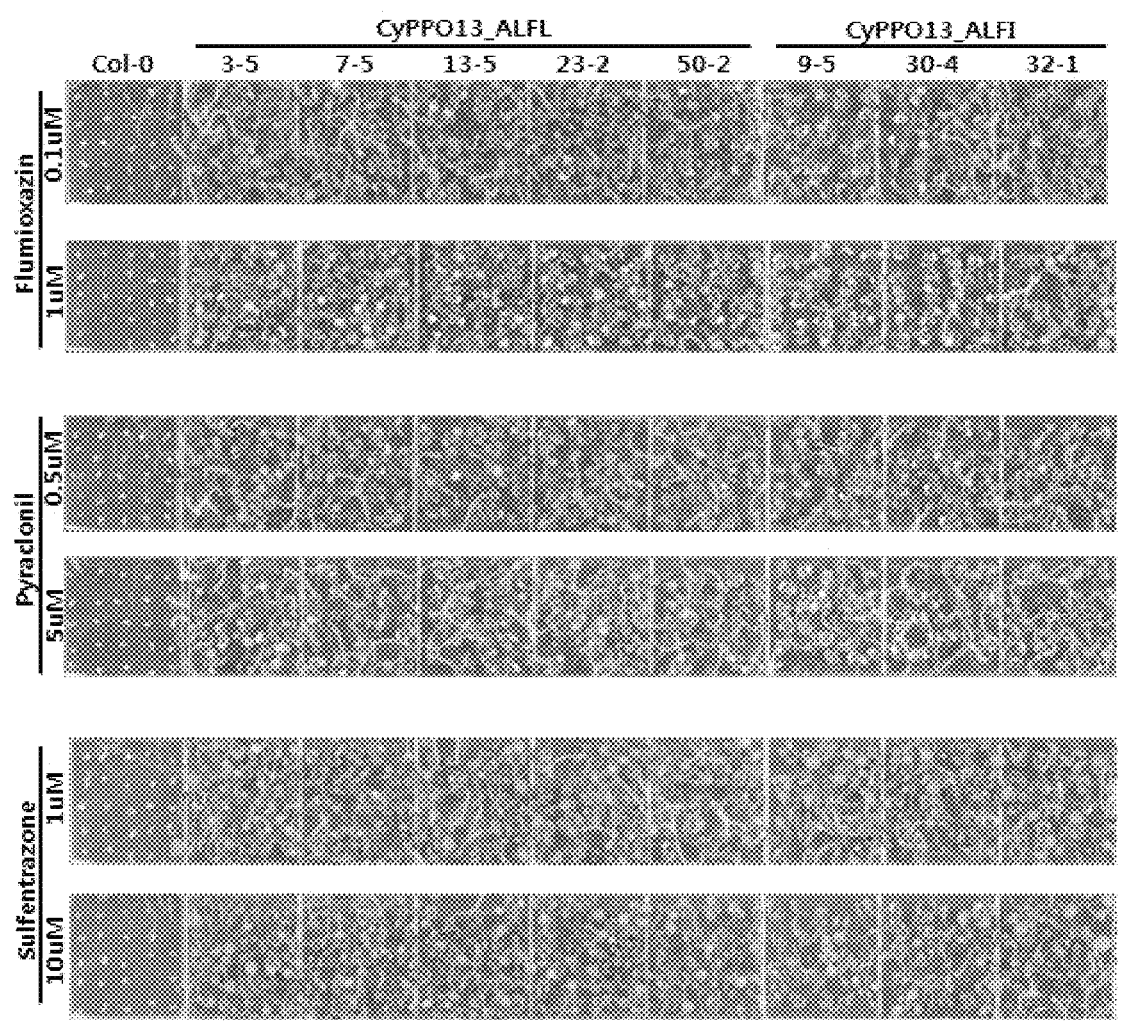
[Fig. 31c]

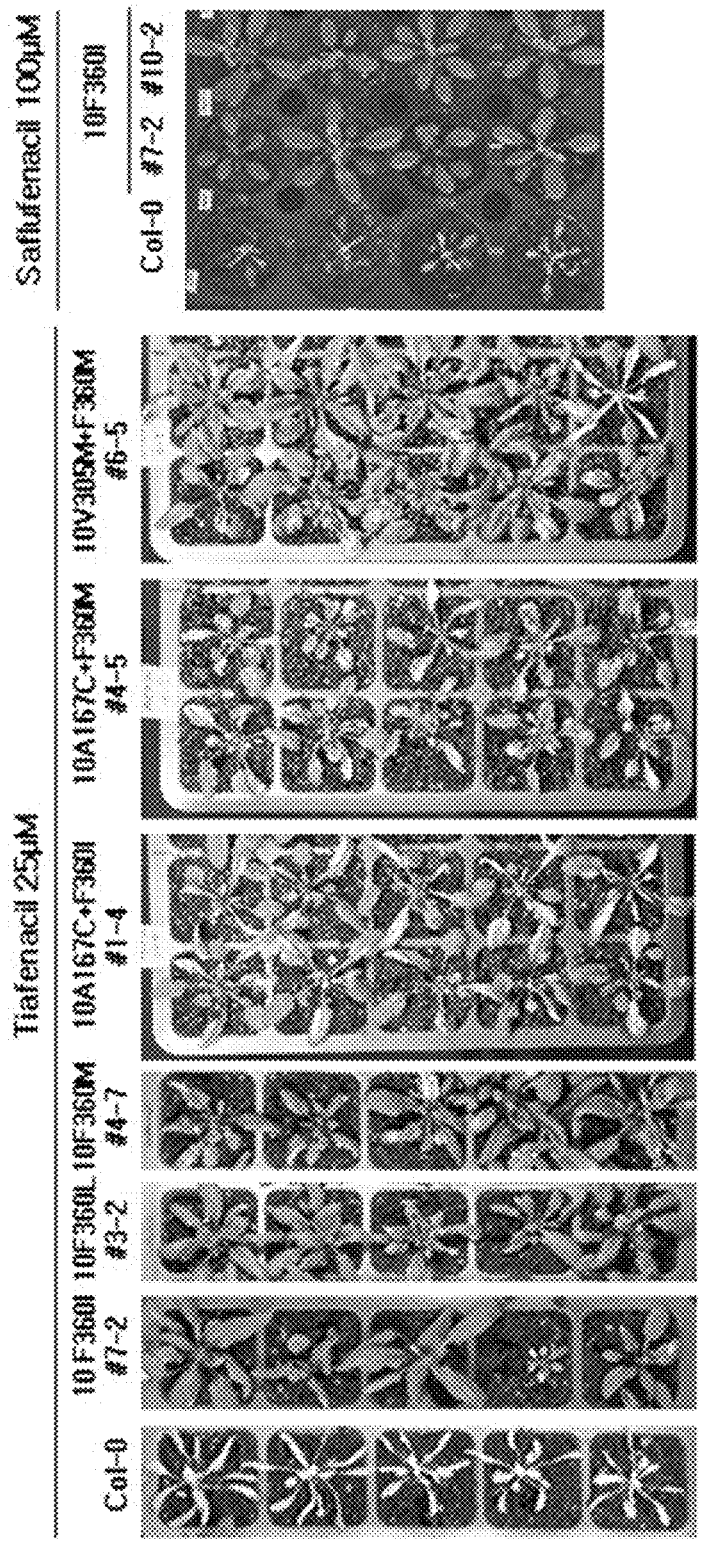
[Fig. 32]

[Fig. 33a]
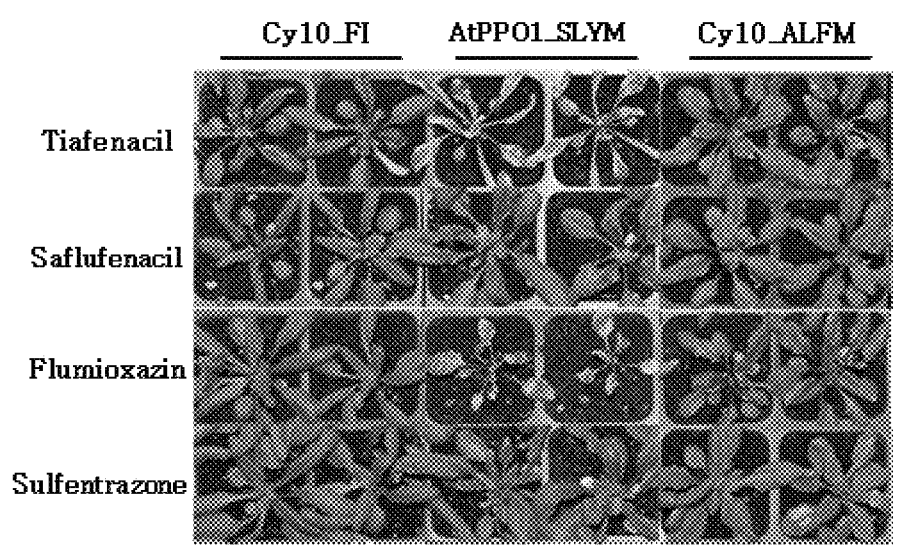

[Fig. 33b]
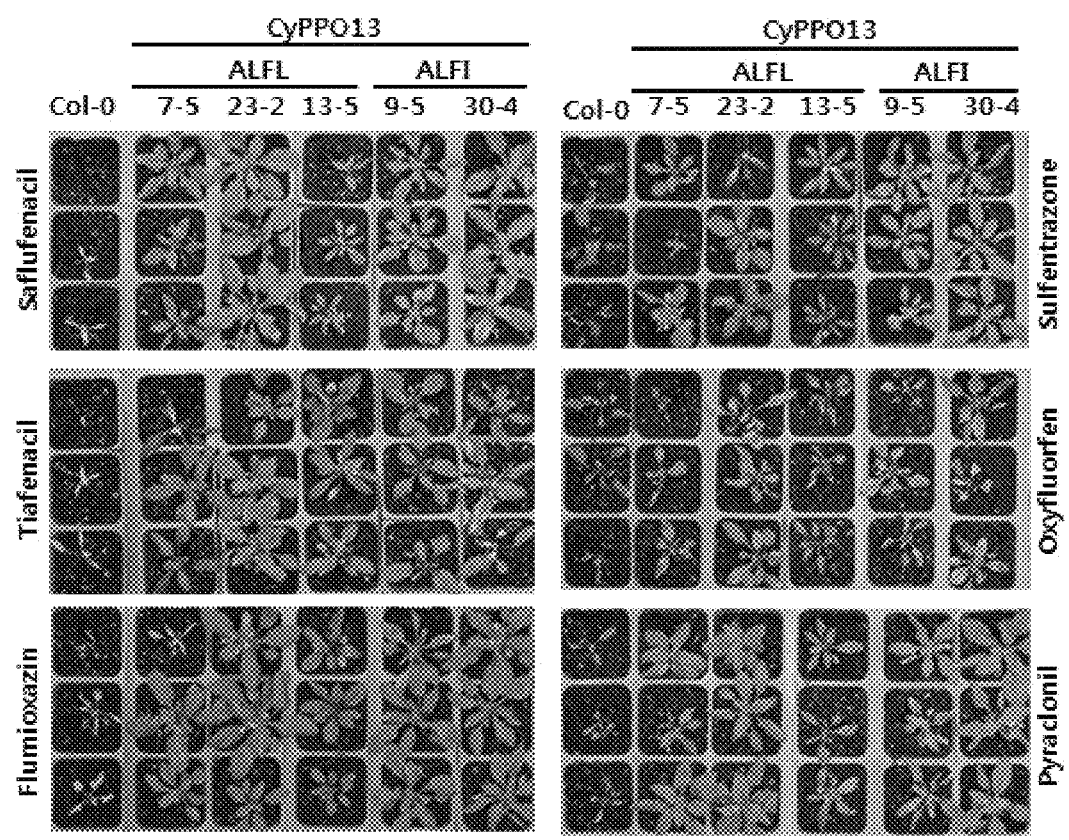

[Fig. 34]
CyPPO10 F360I(T₄)
Tiafenacil 15μM
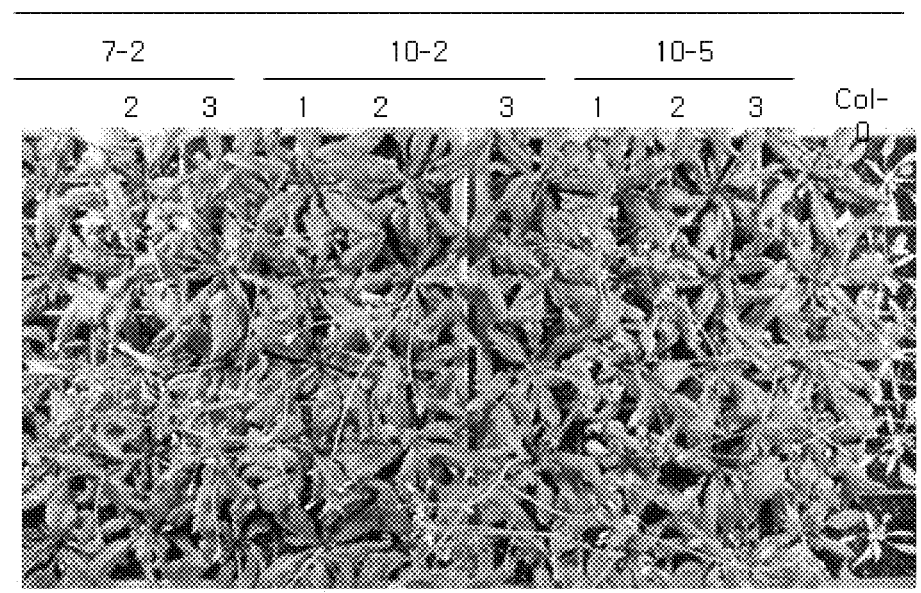
Saflufenacil 150μM
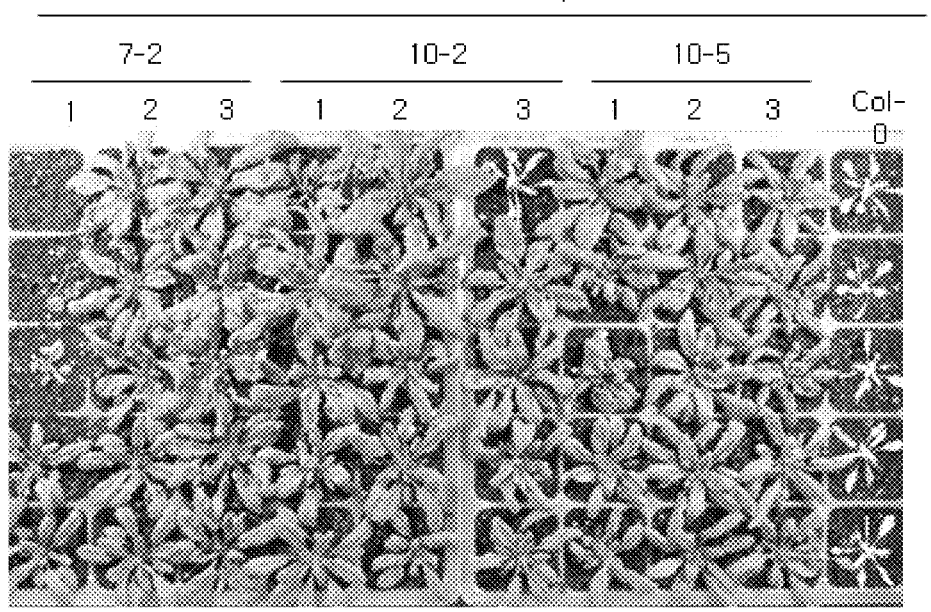

[Fig. 35]
CyPPO10 F360I(T5)
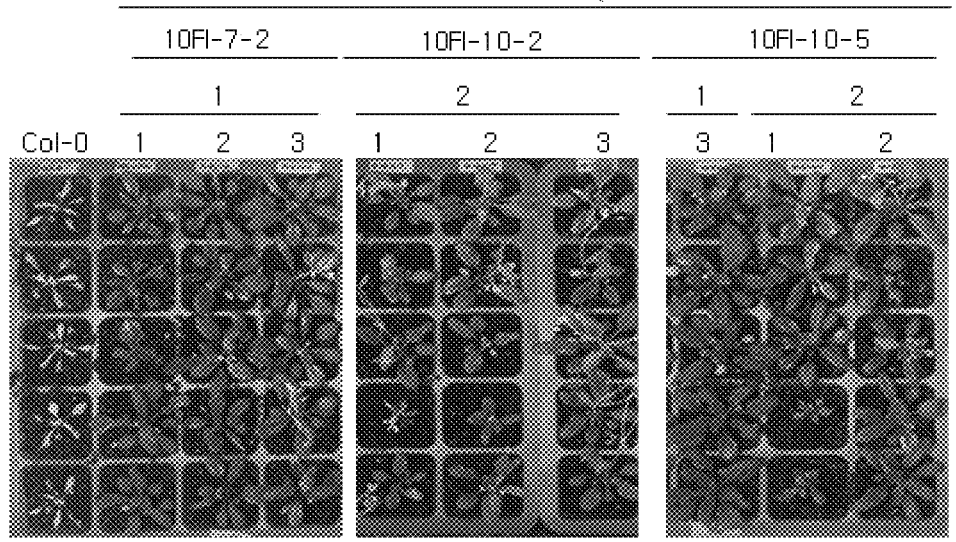
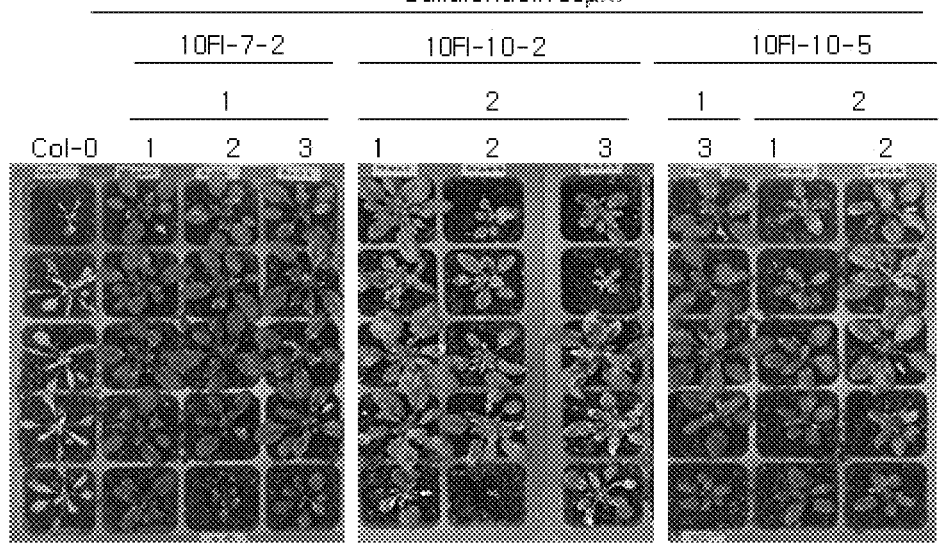

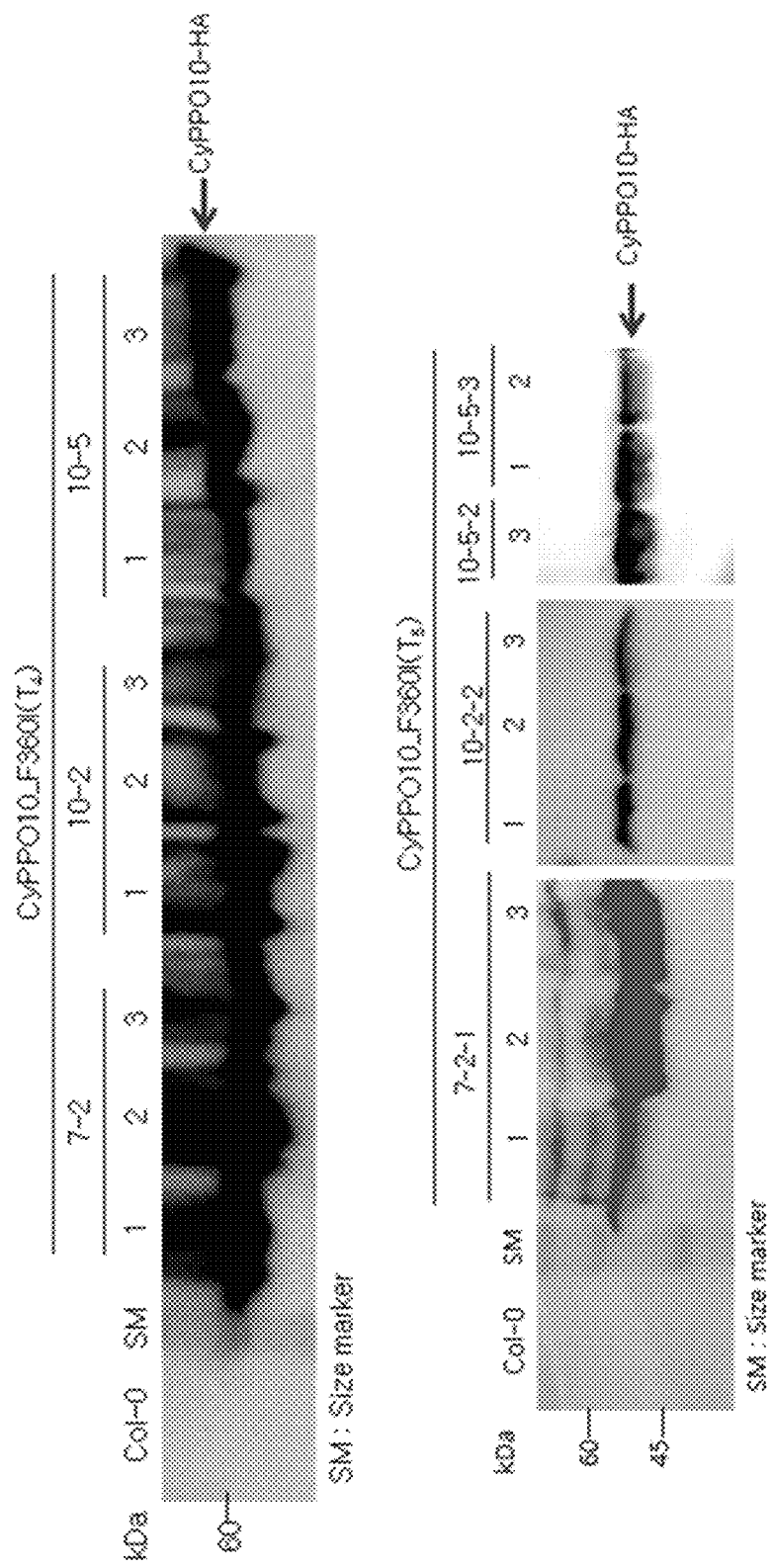
[Fig. 36]

[Fig. 37]
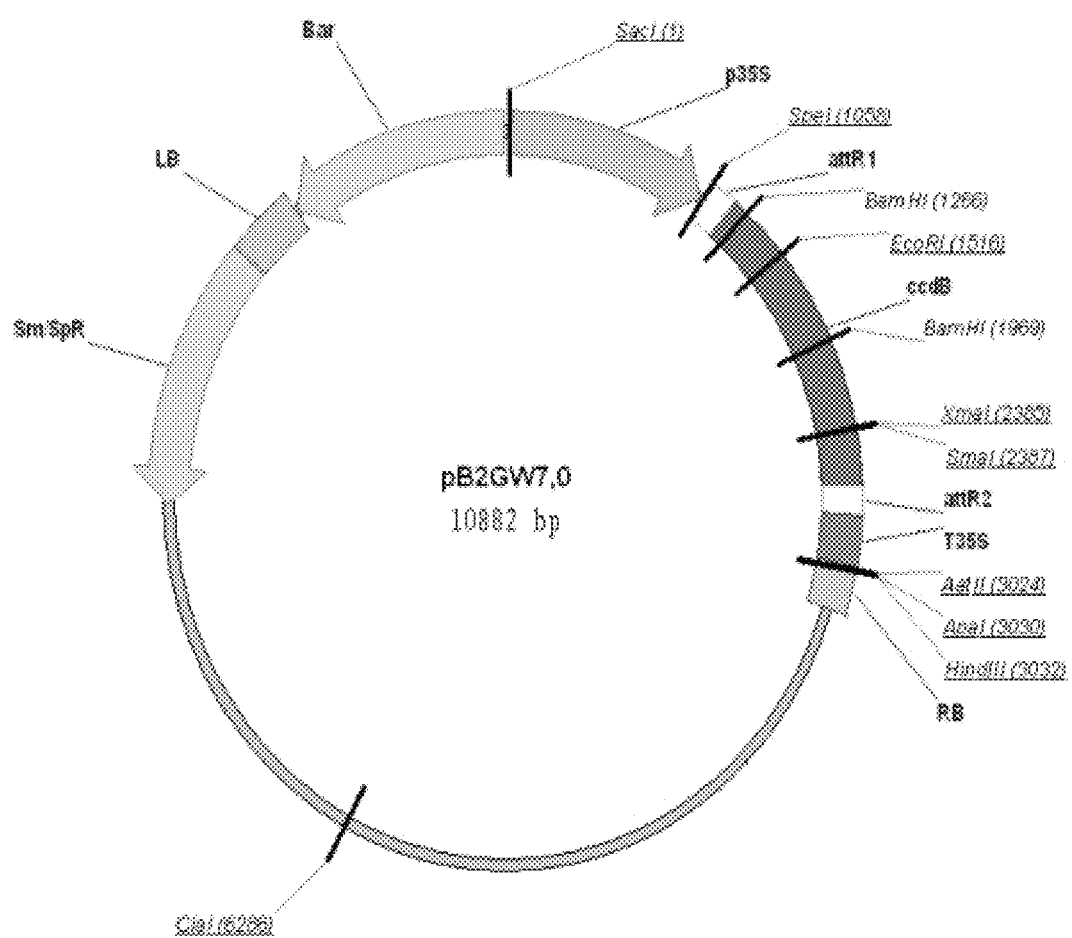

[Fig. 38]
Kwangan soybean
(Wild type)
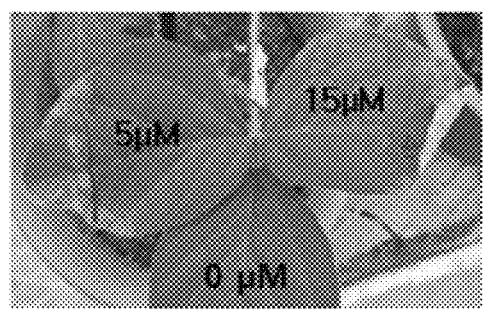
CyPPO10 A167L+F360M #2
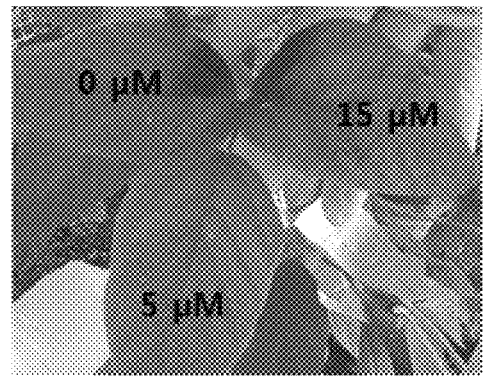

[Fig. 39]
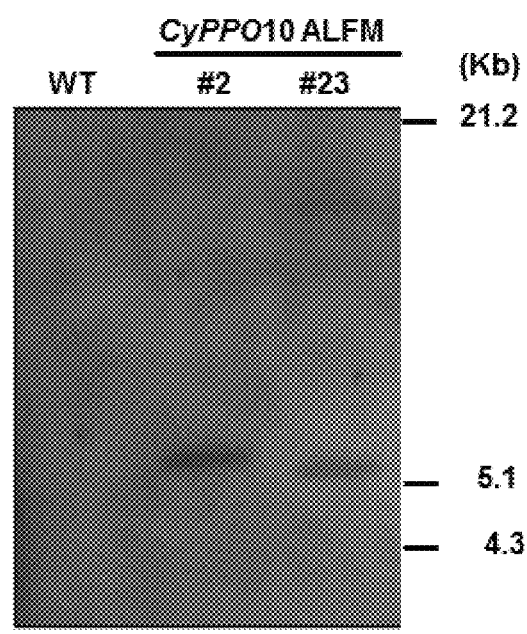

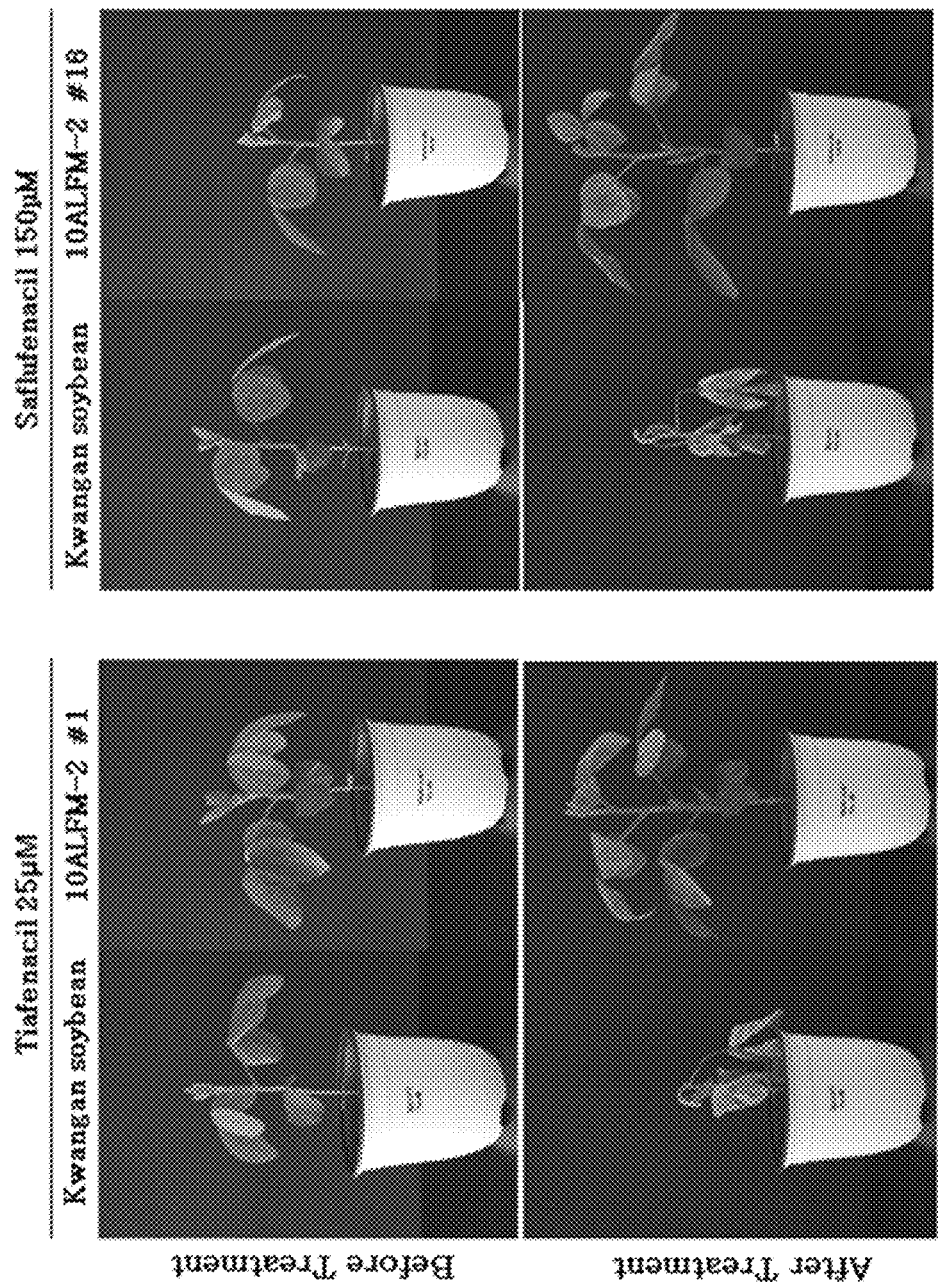
[Fig. 40]

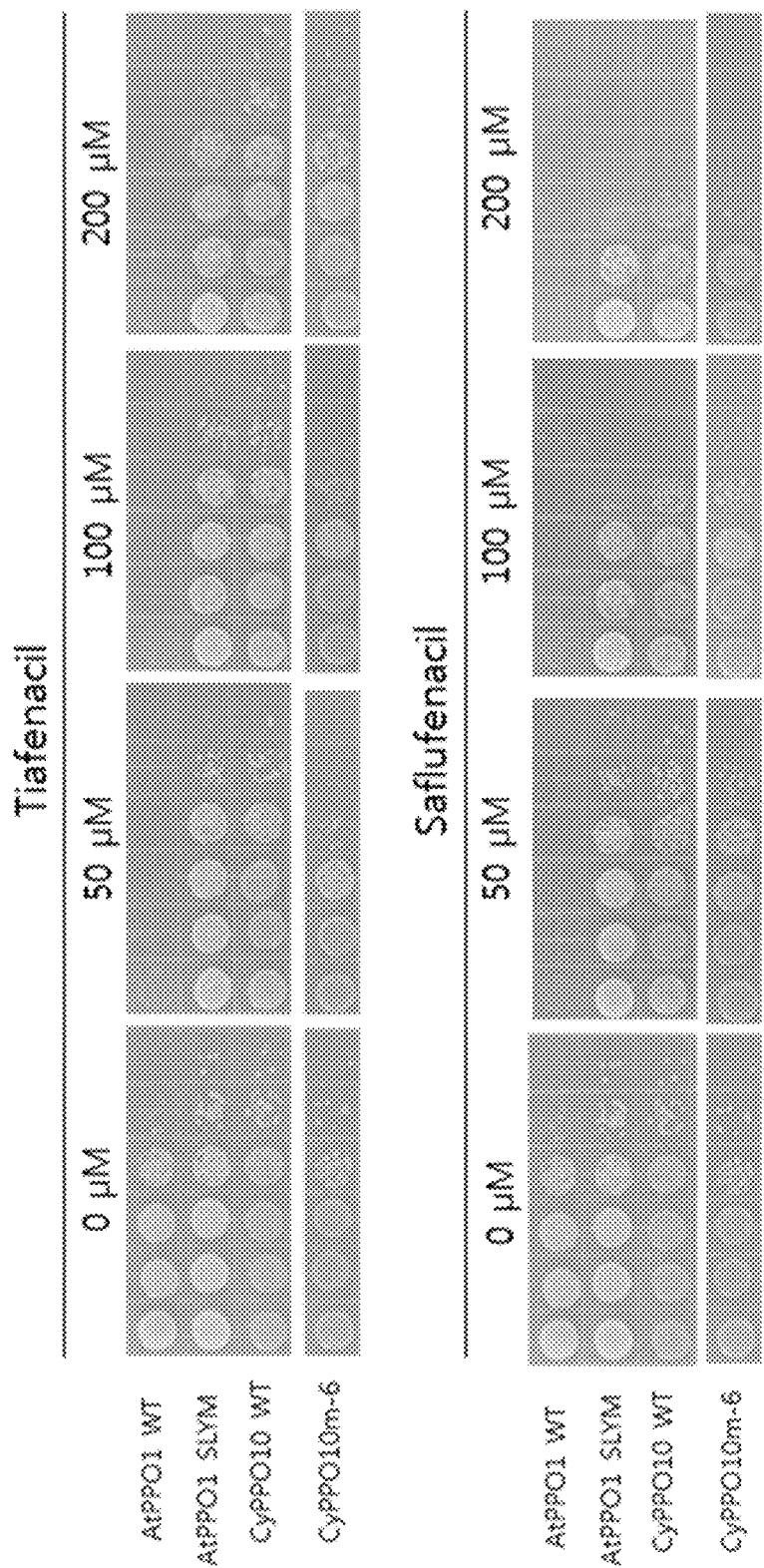

METHODS AND COMPOSITIONS FOR CONFERRING AND/OR ENHANCING HERBICIDE TOLERANCE USING PROTOPORPHYRINOGEN OXIDASE OR VARIANT THEREOF

CROSS-REFERENCES TO RELATED APPLICATION

This application is a Divisional Application of U.S. patent application Ser. No. 16/307,680 which was filed on Dec. 6, 2018, which is a National Stage application of PCT/KR2017/006275 filed on Jun. 15, 2017, which claims priority to Korean Patent Application No. 10-2016-0075358 filed on Jun. 16, 2016, the contents of which are incorporated herein by reference.

TECHNICAL FIELD

Provided are protoporphyrinogen oxidases derived from prokaryotes or its variants, and technology for conferring and/or enhancing herbicide tolerance of plants and/or algae using the same.

BACKGROUND ART

A porphyrin biosynthetic pathway serves for the synthesis of chlorophyll and heme which play vital roles in plant metabolism, and it takes place in the chloroplast. In this pathway, protoporphyrinogen IX oxidase (hereinafter, referred to as PPO; EC:1.3.3.4) catalyzes the oxidation of protoporphyrinogen IX to protoporphyrin IX. After the oxidation of protoporphyrinogen IX to protoporphyrin IX, protoporphyrin IX binds with magnesium by Mg-chelatase to synthesize chlorophyll, or it binds with iron by Fe-chelatase to synthesize heme.

Therefore, when PPO activity is inhibited, synthesis of chlorophylls and heme is inhibited and the substrate protoporphyrinogen IX leaves the normal porphyrin biosynthetic pathway, resulting in the rapid export of protoporphyrinogen IX from the chloroplast to the cytoplasm, and cytoplasmic protoporphyrin IX accumulation caused by the oxidation. Accumulated protoporphyrin IX generates highly reactive singlet oxygen ($^1O_2$) in the presence of light and oxygen molecules which destroy cell membrane and rapidly lead to plant cell death. Based on this principle, herbicides inhibiting PPO activity have been developed. Until now, there have been 9 families of PPO inhibiting herbicides, including pyrimidinediones, diphenyl-ethers, phenylpyrazoles, N-phenylphthalimides, thiadiazoles, oxadiazoles, triazolinones, oxazolidinediones, and others herbicides, which are classified according to their chemical structures.

Further, in order to prevent effects of these herbicides on the growth of crops while using the herbicides, there is a need to provide herbicide tolerance for the crops.

Meanwhile, algae are photosynthetic organisms that can convert light energy into chemical energy which can be used to synthesize various useful compounds. For example, algae can fix carbon by photosynthesis and convert carbon dioxide into sugar, starch, lipids, fats, or other biomolecules, thereby removing greenhouse gases from the atmosphere. In addition, large-scale cultivation of algae can produce a variety of substances such as industrial enzymes, therapeutic compounds and proteins, nutrients, commercial materials and fuel materials.

However, in case of large-scale cultivation of algae in a bioreactor or in an open or enclosed pond, contamination may occur by undesired competitive organisms, for example, undesired algae, fungi, rotifer, or zooplankton.

Thus, a technology is needed to harvest desired plants and/or algae on a large scale by treating herbicides at a concentration that would inhibits the growth of competitive organisms without herbicide tolerance, after conferring herbicide tolerance to desired plants and/or algae.

REFERENCES (Patent document 1) U.S. Pat. No. 6,308,458 (2001 Oct. 30)
(Patent document 2) U.S. Pat. No. 6,808,904 (2004 Oct. 26)
(Patent document 3) U.S. Pat. No. 7,563,950 (2009 Jul. 21)
(Patent document 4) International patent application laid-open publication WO2011/085221 (2011 Jul. 14)
(Non-patent document 1) Li X, Volrath S L, Chilcott C E, Johnson M A, Ward E R, Law M D, Development of protoporphyrinogen oxidase as an efficient selection marker for *Agrobacterium tumefaciens*-mediated transformation of maize. Plant physiology 133:736-747, 2003

DISCLOSURE

Technical Problem

In this specification, it is found that hemY-type PPO genes derived from prokaryotes and mutants thereof show a wide herbicide tolerance to protoporphyrinogen oxidase (PPO)-inhibiting herbicides, and thereby it is proposed if providing plants and/or algae with the same, herbicide tolerance can be conferred and/or enhanced.

One embodiment provides a polypeptide variant comprising, consisting essentially of, or consisting of:

(1) an amino acid sequence wherein one or more selected from the group consisting of amino acids affecting to the interaction between a PPO inhibiting herbicide and the polypeptide of PPO, SEQ ID NO: 2 (e.g., amino acids positioned on binding sites of SEQ ID NO: 2 interacting with PPO inhibiting herbicide) are respectively and independently deleted or substituted with an amino acid which is different from original amino acid in the corresponding position, or (2) an amino acid sequence having 95% or higher, 98% or higher, or 99% or higher sequence homology with the amino acid sequence (1).

The one or more selected from the group consisting of amino acids affecting to the interaction between PPO inhibiting herbicides and the polypeptide of PPO, SEQ ID NO: 2, may be one or more selected from the group consisting of N59, S60, R89, F161, V165, A167, Q184, P303, V305, F324, L327, I340, F360, and I408, of the amino acid sequence of SEQ ID NO: 2.

Another embodiment provides a polypeptide variant comprising, consisting essentially of, or consisting of:

(1) an amino acid sequence wherein one or more selected from the group consisting of amino acids affecting to the interaction between PPO inhibiting herbicides and the polypeptide of PPO, SEQ ID NO: 4 (e.g., amino acids positioned on binding sites of SEQ ID NO: 4 interacting with PPO inhibiting herbicide) are respectively and independently deleted or substituted with an amino acid which is different from original amino acid in the corresponding position, or (2) an amino acid sequence having 95% or higher, 98% or higher, or 99% or higher sequence homology with the amino acid sequence (1).

The one or more selected from the group consisting of amino acids affecting to the interaction between PPO inhibiting herbicides and the polypeptide of PPO, SEQ ID NO: 4, may be one or more selected from the group consisting of R101, F171, V175, A177, G194, P316, V318, F337, L340, I353, and F373, of the amino acid sequence of SEQ ID NO: 4.

Other embodiment provides a polynucleotide encoding the polypeptide or the polypeptide variant.

Other embodiment provides a recombinant vector comprising the polynucleotide.

Other embodiment provides a recombinant cell comprising the recombinant vector.

Other embodiment provides a composition for conferring or enhancing herbicide tolerance of plants or algae, comprising one or more selected from the group consisting of:

the polypeptide of SEQ ID NO: 2, the polypeptide of SEQ ID NO: 4, a polypeptide variant thereof as described above, and a polypeptide with an amino acid sequence having 95% or higher, 98% or higher, or 99% or higher sequence homology with the polypeptide or polypeptide variants;

a polynucleotide encoding the polypeptide, the polypeptide variants, and a polypeptide with an amino acid sequence having 95% or higher, 98% or higher, or 99% or higher sequence homology with the polypeptide or variants;

a recombinant vector comprising the polynucleotide; and a recombinant cell comprising the recombinant vector.

For example, the polynucleotide encoding the polypeptide of SEQ ID NO: 2 may comprise the polynucleotide sequence of SEQ ID NO: 1, and the polypeptide of SEQ ID NO: 4 may comprise the polynucleotide sequence of SEQ ID NO: 3, but not limited thereto.

The herbicide may be an herbicide inhibiting protoporphyrinogen oxidase.

As a specific embodiment, the herbicide may be one or more selected from the group consisting of pyrimidinediones, diphenyl-ethers, phenylpyrazoles, N-phenylphthalimides, phenylesters, thiadiazoles, oxadiazoles, triazolinones, oxazolidinediones and other herbicides, but not limited thereto.

As a specific embodiment, the herbicide may be one or more selected from the group consisting of butafenacil, saflufenacil, benzfendizone, tiafenacil, fomesafen, oxyfluorfen, aclonifen, acifluorfen, bifenox, ethoxyfen, lactofen, chlomethoxyfen, chlorintrofen, fluoroglycofen-ethyl, halosafen, pyraflufen-ethyl, fluazolate, flumioxazin, cinidon-ethyl, flumiclorac-pentyl, fluthiacet, thidiazimin, oxadiargyl, oxadiazon, carfentrazone, sulfentrazone, azafenidin, pentoxazone, pyraclonil, flufenpyr-ethyl, profluazol, phenopylate (2,4-dichlorophenyl 1-pyrrolidinecarboxylate), carbamate analogues of phenopylate (for example, O-phenylpyrrolidino- and piperidinocarbamate analoges (refer to"Ujjana B. Nandihalli, Mary V. Duke, Stephen O. Duke, Relationships between molecular properties and biological activities of O-phenyl pyrrolidino- and piperidinocarbamate herbicides, J. Agric. Food Chem., 1992, 40(10) 1993-2000")), agriculturally acceptable salts thereof, and combinations thereof, but not limited thereto.

The plant means a multicellular eukaryote having photosynthetic capability, which may be a monocotyledonous plant or a dicotyledonous plant, and may be an herbaceous plant or a woody plant. The algae mean unicellular organism having photosynthetic capability, which may be a prokaryotic alga or a eukaryotic alga.

In one embodiment, the plants and algae are genetically manipulated in order to further comprise a second herbicide tolerance polypeptide or a gene encoding thereof, and broader range of herbicide tolerance to the second herbicide may be conferred and/or enhanced. The plants and algae genetically manipulated in order to comprise the second herbicide tolerance polypeptide or a gene encoding thereof more may be prepared using a composition for conferring and/or enhancing tolerance to the herbicide wherein the second herbicide tolerance polypeptide or a gene encoding thereof is further comprised. Thus, a composition for conferring and/or enhancing tolerance to the herbicide may further comprise the second herbicide tolerance polypeptide or a gene encoding thereof.

As a specific embodiment, the second herbicide may include cell division-inhibiting herbicides, photosynthesis-inhibiting herbicides, amino acid synthesis-inhibiting herbicides, plastid-inhibiting herbicides, and cell membrane-inhibiting herbicides, but not limited thereto.

As a specific embodiment, the second herbicide may be exemplified by glyphosate, glufosinate, dicamba, 2,4-D(2, 4-dichlorophenoxyacetic acid), isoxaflutole, ALS (acetolactate synthase)-inhibiting herbicide, photosystem II-inhibiting herbicide, phenylurea-based herbicide, bromoxynil-based herbicide, and combinations thereof, but not limited thereto.

As a specific embodiment, the second herbicide may be exemplified by one or more selected from the group consisting of glyphosate herbicide-tolerant EPSPS (glyphosate tolerant-enolpyruvylshikimate-3-phosphate synthase), GOX (glyphosate oxidase), GAT (glyphosate-N-acetyltransferase) or glyphosate decarboxylase); glufosinate herbicide-tolerant PAT (phosphinothricin-N-acetyltransferase); dicamba herbicide-tolerant DMO (dicamba monooxygenase); 2,4-D herbicide-tolerant 2,4-D monooxygenase or AAD (aryloxyalkanoate dioxygenase); ALS-inhibiting sulfonylurea-based herbicide-tolerant ALS (acetolactate Synthase), AHAS (acetohydroxyacid synthase), or Athahasl (acetohydroxyacid synthase Large Subunit); photosystem II-inhibiting herbicide-tolerant photosystem II protein D1; phenylurea-based herbicide-tolerant cytochrome P450; plastid-inhibiting herbicide-tolerant HPPD (hydorxylphenylpyruvate dioxygenase); bromoxynil herbicide-tolerant nitrilase; and combinations thereof, but not limited thereto.

Further, the gene encoding the second herbicide-tolerant polypeptide may be exemplified by one or more selected from the group consisting of glyphosate herbicide-tolerant cp4 epsps, epsps (AG), mepsps, 2mepsps, goxv247, gat4601 or gat4621 gene; glufosinate herbicide-tolerant bar, pat or pat (SYN) gene; dicamba herbicide-tolerant dmo gene; 2,4-D herbicide-tolerant AAD-1, AAD-12 gene; ALS-inhibiting sulfonylurea-based herbicide-tolerant ALS, GM-HRA, S4-HRA, ZM-HRA, Csr1, Csr1-1, Csr1-2, SurA or SurB; photosystem II-inhibiting herbicide-tolerant psbA gene; phenylurea herbicide-tolerant CYP76B1 gene; isoxaflutole herbicide-tolerant HPPDPF W336 gene and bromoxynil herbicide-tolerant bxn gene; and combinations thereof, but not limited thereto.

Other embodiment provides a transformant of a plant and/or algae having herbicide tolerance, which are transformed with the polynucleotide, or a clone or progeny thereof.

Other embodiment provides a method of preparing plants or algae having herbicide tolerance, comprising a step of transforming plants and/or algae with the polynucleotide.

Other embodiment provides a method of conferring or enhancing herbicide tolerance of plants and/or algae, comprising a step of transforming plants and/or algae with the polynucleotide.

The transformation may be performed on algae, and/or plant cell, protoplast, callus, hypocotyl, seed, cotyledon, shoot, or whole plant.

The transformant may be algae, and/or plant cell, protoplast, callus, hypocotyl, seed, cotyledon, shoot, or whole plant.

Other embodiment provides a method of controlling weeds in a cropland comprising:

a step of providing the cropland with a plant comprising one or more selected from the group comprising of the polypeptide of SEQ ID NO: 2 or 4, the polypeptide variant, a polynucleotide encoding thereof, a recombinant vector comprising the polynucleotide, and a recombinant cell comprising the recombinant vector; and a step of applying an effective dosage of a protoporphyrinogen oxidase-inhibiting herbicide to the cropland (or to the plant).

As a specific embodiment, the step of applying an effective dosage of protoporphyrinogen oxidase-inhibiting herbicide to the cropland may be performed by applying an effective dosage of two or more protoporphyrinogen oxidase-inhibiting herbicides sequentially or simultaneously.

As other embodiment, the plant may be genetically manipulated in order to further comprise a second herbicide-tolerant polypeptide or a gene encoding the same, and an effective dosage of the protoporphyrinogen oxidase-inhibiting herbicide and the second herbicide may be applied sequentially or simultaneously.

Other embodiment provides a method of removing an undesired aquatic organism from a culture medium, comprising a step of providing a culture medium with algae comprising one or more selected from the group consisting of the polypeptide, the polypeptide variant, a polynucleotide encoding the polypeptide or the polypeptide variant, a recombinant vector comprising the polynucleotide, and a recombinant cell comprising the recombinant vector, and a step of applying an effective dosage of protoporphyrinogen oxidase-inhibiting herbicide to the culture medium.

Technical Solution

Provided is a technology of conferring and/or enhancing herbicide tolerance of plants or algae.

Herein, 'conferring and/or enhancing herbicide tolerance of plants or algae' or 'enhancing herbicide tolerance of plants or algae' is interpreted as conferring tolerance on plants or algae which do not have herbicide tolerance, or enhancing tolerance of plants or algae which have herbicide tolerance, or broad meaning of covering both.

As used herein, 'consisting of a sequence,' 'consisting essentially of a sequence,' or 'comprising a sequence' is used in order to mean both cases of comprising described sequence, or necessarily comprising the sequence, and may be interpreted as meaning of comprising a sequence other than described sequence and/or comprising mutation (addition, deletion, and/or substitution of an amino acid or nucleic acid), as long as maintaining an intrinsic activity of protein, polypeptide, or nucleic acid molecule and exhibiting intended function.

In one embodiment, provided are one or more polypeptide variants selected from the group consisting of:

a polypeptide variant comprising, consisting essentially of, or consisting of an amino acid sequence wherein one or more selected from the group consisting of amino acids affecting to the interaction between PPO inhibiting herbicides and polypeptide of PPO, SEQ ID NO: 2 (e.g., amino acids positioned on binding sites of SEQ ID NO: 2 interacting with PPO inhibiting herbicide), are respectively and independently deleted or substituted with other amino acid which is different from the original amino acid, or an amino acid sequence having 95% or higher, 98% or higher, or 99% or higher homology thereto; and a polypeptide variant comprising, consisting essentially of, or consisting of amino acids affecting to the interaction between PPO inhibiting herbicides and polypeptide of PPO, SEQ ID NO: 4 (e.g., amino acids positioned on binding sites of SEQ ID NO: 4 interacting with PPO inhibiting herbicide), are respectively and independently deleted or substituted with other amino acid which is different from original amino acid in the corresponding position, or an amino acid sequence having 95% or higher, 98% or higher, or 99% or higher homology thereto.

In other embodiment, provided is a polynucleotide encoding the polypeptide or the polypeptide variant, a recombinant vector comprising the polynucleotide, and a recombinant cell comprising the recombinant vector. The polynucleotide may be designed in order that an optimized codon is comprised in a cell to be transformed among codons encoding each amino acid. The optimized codon may be easily known to a person skilled in the art (for example, refer to "http://www.genscript.com/codon-opt.html", "http://sg.idtdna.com/CodonOpt" etc.).

In other embodiment, provided a composition for conferring or enhancing herbicide tolerance of plants or algae, comprising one or more selected from the group consisting of:

the polypeptide of SEQ ID NO: 2, the polypeptide of SEQ ID NO: 4, the polypeptide variants thereof, and a polypeptide with an amino acid sequence having 95% or higher, 98% or higher, or 99% or higher sequence homology thereto;

a polynucleotide encoding the polypeptide or the polypeptide variants;

a recombinant vector comprising the polynucleotide; and a recombinant cell comprising the recombinant vector.

For example, the polynucleotide encoding the polypeptide of SEQ ID NO: 2 may comprise the polynucleotide sequence of SEQ ID NO: 1, and the polypeptide of SEQ ID NO: 4 may comprise the polynucleotide sequence of SEQ ID NO: 3, but not limited thereto.

Another embodiment provides a transformant of a plant or algae having herbicide tolerance, which is transformed with the polynucleotide encoding the polypeptide or the polypeptide variant. The polynucleotide may be designed in order that an optimized codon is comprised in a cell to be transformed among codons encoding each amino acid. The optimized codon may be easily known to a person skilled in the art (for example, refer to "http://www.genscript.com/codon-opt.html", "http://sg.idtdna.com/CodonOpt" etc.).

In other embodiment, provided is a method of preparing plants or algae having herbicide tolerance, comprising a step of transforming algae, or plant cell, protoplast, callus, hypocotyl, seed, cotyledon, shoot, or whole plant with the polynucleotide.

In other embodiment, provided is a method of conferring or enhancing herbicide tolerance of plants or algae, comprising a step of transforming algae, or plant cell, protoplast, callus, hypocotyl, seed, cotyledon, shoot, or whole plant with the polynucleotide.

Hereinafter, the present invention will be described in more detail.

The polypeptide having amino acid sequences of SEQ ID NO: 2 or 4, or an amino acid sequence having 95% or higher, 98% or higher, or 99% or higher sequence homology with thereof and its variant provided herein is a PPO protein derived from a prokaryote (for example, cyanobacteria), and is an herbicide-tolerant PPO protein having tolerance to PPO inhibiting herbicides. Specifically, a PPO protein which is derived from *Thermosynechococcus elongatus* BP-1 is provided, and it is designated as CyPPO10, and its amino acid sequence is represented by SEQ ID NO: 2, and a nucleotide sequence of a gene encoding thereof is represented by SEQ ID NO: 1. In addition, a PPO derived from *Synechococcus* sp. JA-3-3Ab strain is provided, and it is designated as CyPPO13, and its amino acid sequence is represented by SEQ ID NO: 4, and a nucleotide sequence of a gene encoding thereof is represented by SEQ ID NO: 3.

Herein, the polypeptide and variants of the polypeptide described above may be expressed respectively as herbicide-tolerant PPO protein or herbicide-tolerant PPO protein variant having tolerance to PPO inhibiting herbicides. In addition, as used herein, "herbicide-tolerant PPO or its variant" may be used in order to mean the above herbicide-tolerant PPO protein or herbicide-tolerant PPO protein variant, herbicide-tolerant PPO protein-encoding gene or herbicide-tolerant PPO protein variant-encoding gene, or all of them.

Cyanobacteria-derived PPO proteins have more excellent enzyme activity themselves than plant PPOs, and these PPO proteins can confer tolerance to PPO-inhibiting herbicides and intensify herbicide tolerance by comprising amino acid mutation in a range of overall maintaining intrinsic enzyme activity than wild type PPO proteins. Such amino acid mutation may be comprise substitution, deletion, addition and/or introduction of one or more of amino acids selected from amino acid residues of interaction sites between PPO proteins and herbicides.

The PPO protein variant will be described in more detail as follows.

One embodiment provides a polypeptide variant comprising, consisting essentially of, or consisting of:

an amino acid sequence wherein one or more selected from the group consisting of amino acids affecting to the interaction between PPO inhibiting herbicides and the polypeptide of PPO, SEQ ID NO: 2 (CyPPO10) (e.g., amino acids positioned on binding sites to PPO inhibiting herbicides of polypeptide of SEQ ID NO: 2), are respectively and independently deleted or substituted with other amino acid which is different from the original amino acid (namely, an amino acid in the corresponding position of the wild type) or an amino acid sequence having 95% or higher, 98% or higher, or 99% or higher homology thereto.

The amino acid residue of polypeptide of SEQ ID NO: 2 which is deleted or substituted with other amino acid that is different from the original amino acid (namely, one or more selected from the group consisting of amino acids positioned in binding sites to PPO inhibiting herbicides of polypeptide of SEQ ID NO: 2) may be one or more selected from the group consisting of N59 (meaning of "N(Asn) in the 59$^{th}$ position"; the expression of the following amino acid residues is interpreted in the same manner), S60, R89, F161, V165, A167, Q184, P303, V305, F324, L327, I340, F360, and I408 of the amino acid sequence of SEQ ID NO: 2.

In one specific embodiment, the variant of polypeptide may comprise, consist essentially of, or consist of:

an amino acid sequence wherein one or more selected from the group consisting of N59, S60, R89, F161, V165, A167, Q184, P303, V305, F324, L327, I340, F360, and I408 of the amino acid sequence of SEQ ID NO: 2 are respectively and independently deleted or substituted with an amino acid which is selected from the group consisting of M (Met), V (Val), I (Ile), T (Thr), L (Leu), C (Cys), A (Ala), S (Ser), F (Phe), P (Pro), W (Trp), N (Asn), Q (Gln), G (Gly), Y (Tyr), D (Asp), E (Glu), R (Arg), H (His), K (Lys), etc. and is different from the original amino acid at the corresponding position (for example, substituted with an amino acid which is selected from the group consisting of M (Met), V (Val), I (Ile), T (Thr), L (Leu), C (Cys), A (Ala), S (Ser), R (Arg), W (Trp), G (Gly) etc. and is different from the original amino acid at the corresponding position in the wild type), or an amino acid sequence having 95% or higher, 98% or higher, or 99% or higher homology thereto.

For example, the variant of polypeptide may comprise, consist essentially of, or consist of:

an amino acid sequence comprising one or more amino acid mutations selected from the group consisting of F360M (meaning of "the amino acid residue in the 360th position is substituted from F (Phe) to M (Met)"; the expression of the following amino acid mutations is interpreted in the same manner), F360V, F360I, F360T, F360L, F360C, A167C, A167L, A167I, P303L, V305L, V305M, V305T, N59T, S60T, R89A, R89L, R89V, F161A, V165S, V165C, Q184G, F324V, L327T, I340T, I408R, and I408W, in the amino acid sequence of SEQ ID NO: 2 or an amino acid sequence having 95% or higher, 98% or higher, or 99% or higher homology thereto.

More specifically, the variant of polypeptide may comprise, consist essentially of, or consist of:

an amino acid sequence comprising one or more amino acid mutations selected from the group consisting of amino acid mutations of F360M, F360V, F360I, F360T, F360L, F360C, A167C, A167L, A167I, P303L, N59T, S60T, R89A, R89L, R89V, F161A, V165S, V165C, Q184G, V305L, V305M, V305T, F324V, L327T, I340T, I408R, I408W, P303L+V305L (meaning of a mutant or mutation comprising all of substitution of the 303$^{rd}$ residue from P to L and substitution of the 305$^{th}$ residue from V to L; the expression of the following two or more amino acid mutations is interpreted in the same manner), N59T+F360V, S60T+V165S+F360M, S60T+V165S+F360I, S60T+I340T+F360I, R89A+F360M, R89A+F360I, R89A+F360L, R89L+F360I, R89V+F360I, R89A+A167L+F360M, R89A+V305T+F360M, V165S+F360M, V165S+F360I, V165S+F360L, V165S+F360V, V165C+F360M, V165C+A167C+F360M, V165C+A167I+F360M, V165C+A167L+F360M, A167L+F360M, A167L+F360I, A167C+F360M, A167C+F360I, A167I+F360M, V305M+F360M, V305T+F360I, V305L+F360M, I408R+F360M, or I408W+F360M, in the amino acid sequence of SEQ ID NO: 2 or an amino acid sequence having 95% or higher, 98% or higher, or 99% or higher homology thereto.

Other embodiment provides a polypeptide variant comprise, consist essentially of, or consist of:

an amino acid sequence wherein one or more selected from the group consisting of amino acids affecting to the interaction between PPO inhibiting herbicides and the polypeptide of PPO, SEQ ID NO: 4 (CyPPO13) (e.g., amino acids positioned on binding sites to PPO inhibiting herbicides of polypeptide of SEQ ID NO: 4), are respectively and independently deleted or substituted with other amino acid which is different from the original amino acid at the corresponding position (namely, an amino acid in the corresponding position of the wild type), or an amino acid sequence having 95% or higher, 98% or higher, or 99% or higher homology thereto.

The amino acid residue of polypeptide of SEQ ID NO: 4 which is deleted or substituted with other amino acid that is different from the original amino acid at the corresponding position (e.g., one or more selected from the group consisting of amino acids positioned in binding sites to PPO inhibiting herbicides of polypeptide of SEQ ID NO: 3) may be one or more selected from the group consisting of R101, F171, V175, A177, G194, P316, V318, F337, L340, I353, and F373, of the amino acid sequence of SEQ ID NO: 4.

In one specific embodiment, the variant of polypeptide may comprise, consist essentially of, or consist of:

an amino acid sequence wherein one or more selected from the group consisting of R101, F171, V175, A177, G194, P316, V318, F337, L340, I353, and F373, of the amino acid sequence of SEQ ID NO: 4 are respectively and independently deleted or substituted with an amino acid which is selected from the group consisting of M (Met), V (Val), I (Ile), T (Thr), L (Leu), C (Cys), A (Ala), S (Ser), F (Phe), P (Pro), W (Trp), N (Asn), Q (Gln), G (Gly), Y (Tyr), D (Asp), E (Glu), R (Arg), H (His), K (Lys), etc. and is different from the original amino acid at the corresponding position in the wild type (for example, substituted with an amino acid which is selected from the group consisting of M (Met), V (Val), I (Ile), T (Thr), L (Leu), C (Cys), A (Ala), E (Glu), Q (Gln), K (Lys), R (Arg), H (His), N (Asn), etc. and is different from the amino acid at the corresponding position in the wild type), or an amino acid sequence having 95% or higher, 98% or higher, or 99% or higher homology thereto.

For example, the variant of polypeptide may comprise, consist essentially of, or consist of:

an amino acid sequence comprising one or more amino acid mutations selected from the group consisting of F373M, F373V, F373I, F373T, F373L, F373C, F373N, F373H, A177C, A177L, A177I, P316A, P316L, V318L, V318M, R101A, F171A, V175C, V175L, G194E, G194Q, G194M, G194K, G194R, F337V, L340T, and I353T, in the amino acid sequence of SEQ ID NO: 4 or an amino acid sequence having 95% or higher, 98% or higher, or 99% or higher homology thereto. More specifically, the variant of polypeptide may comprise an amino acid sequence comprising one or more amino acid mutations selected from the group consisting of amino acid mutations of F373M, F373V, F373I, F373T, F373L, F373C, F373N, F373H, A177C, A177L, A177I, P316A, P316L, V318L, V318M, R101A, F171A, V175C, V175L, G194E, G194Q, G194M, G194K, G194R, F337V, L340T, I353T, P316L+V318L, P316A+V318L, R101A+F373M, A177C+F373M, A177I+F373M, A177L+F373M, A177L+F373I, A177L+F373L, A177L+F373T, A177L+F373V, A177C+F373T, A177C+F373V, V175L+F373M, G194E+F373M, G194Q+F373M, G194M+F373M, G194K+F373M, G194R+F373M, or V318M+F373M, in the amino acid sequence of SEQ ID NO: 4 or an amino acid sequence having 95% or higher, 98% or higher, or 99% or higher homology thereto.

The polypeptide variant comprising an amino acid sequence having sequence homology (for example, 95% or higher, 98% or higher, or 99% or higher sequence homology) described herein may maintain enzyme activity equivalent to that of a polypeptide having an amino acid sequence which is a standard of identification of sequence homology (for example, the PPO protein having amino acid mutation described above), for example, 5% or higher, 10% or higher, 20% or higher, 30% or higher, 40% or higher, 50% or higher, 60% or higher, 70% or higher, 80% or higher, 90% or higher, or 95% or higher enzyme activity to a polypeptide having an amino acid sequence which is a standard in plants (in a whole plant, in a plant cell or cell culture, in a plant tissue, etc.), in algae, and/or in vitro, and having function to confer herbicide tolerance. The sequence homology description is used in order to clarify that the herbicide-tolerance PPO protein variant or polypeptide variant described herein may comprise all sequence mutations in the range of satisfying the above condition (maintain enzyme activity and having function to confer herbicide tolerance).

The names of amino acids used in the description are arranged as follows:

| Amino acid | 3-letter code | 1-letter code |
|---|---|---|
| Alanine | Ala | A |
| Isoleucine | Ile | I |
| Leucine | Leu | L |
| Methionine | Met | M |
| Phenylalanine | Phe | F |
| Proline | Pro | P |
| Tryptophan | Trp | W |
| Valine | Val | V |
| Aspargine | Asn | N |
| Cysteine | Cys | C |
| Glutamine | Gln | Q |
| Glycine | Gly | G |
| Serine | Ser | S |
| Threonine | Thr | T |
| Tyrosine | Tyr | Y |
| Aspartic acid | Asp | D |
| Glutamic acid | Glu | E |
| Arginine | Arg | R |
| Histidine | His | H |
| Lysine | Lys | K |

The herbicide-tolerant PPO protein variant may maintain enzyme activity of PPO protein, and exhibit enhanced herbicide tolerance compared to the wild type.

In addition, the herbicide-tolerant PPO protein variant may comprise further mutation exhibiting biologically equal activity to a polypeptide consisting of SEQ ID NO: 2 or SEQ ID NO: 4, or an amino acid sequence having amino acid mutation described above. For example, the additional mutation may be amino acid substitution which does not overall alter molecular activity, and such amino acid substitution is publicly known in the art. In one example, the additional substitution may be substitution of amino acid residues Ala/Ser, Val/Ile, Asp/Glu, Thr/Ser, Ala/Gly, Ala/Thr, Ser/Asn, Ala/Val, Ser/Gly, Thr/Phe, Ala/Pro, Lys/Arg, Asp/Asn, Leu/Ile, Leu/Val, Ala/Glu, or Asp/Gly, but not limited thereto. In some cases, the herbicide-tolerant PPO protein variant may be under modification by one or more selected from the group consisting of phosphorylation, sulfation, acylation, glycosylation, methylation, farnesylation, etc. In addition, the herbicide-tolerant PPO protein variant may comprise a protein variant wherein structural stability to heat, pH, etc. of the protein is increased or protein activity is increased by amino acid mutation and/or modification.

The term "sequence homology" refers to the degree of similarity to the wild type or reference amino acid sequence or nucleotide sequence, and any protein may be included in the scope of the present invention, as long as it includes amino acid residues having 60% or higher, 65% or higher, 70% or higher, 75% or higher, 80% or higher, 85% or higher, 90% or higher, 95% or higher, 98% or higher, or 99% or higher identity to the amino acid sequence of the herbicide-tolerant PPO protein and retains a biological activity equivalent to the herbicide-tolerant PPO protein variant. Such protein homologues may comprise an active site equivalent to that of a targeted protein. Such homology comparison may be conducted or with the aid of readily available comparison programs. The homology between two or more sequences can be calculated as a percentage (%) using an online available analysis program. The sequence alignment for sequence comparison may be conducted by any conventional method known in the relevant art, and for example, the conventional method may include, but not be limited thereto, GAP, BESTFIT, BLAST, and Clustal Omega.

The herbicide-tolerant PPO protein or its variant may be obtained by extracting from nature and purifying by methods well known in the art. Otherwise, it may be obtained as a recombinant protein using a gene recombination technology. In case of using a gene recombination technology, it may be obtained by a process of collecting herbicide-tolerant PPO protein or its variant from a host cell, after introducing a nucleic acid encoding the herbicide-tolerant PPO protein or its variant into an appropriate expression vector, and transforming a host cell with the vector in order to express a targeted protein. After the protein is expressed in a selected host cell, general biochemical separation techniques, for example, treatment with a protein precipitating agent (salting out), centrifugation, ultrasonic disruption, ultrafiltration, dialysis, chromatography such as molecular sieve chromatography (gel filtration), adsorption chromatography, ion exchange chromatography, affinity chromatography and the like may be used for the isolation and purification thereof, and in order to separate the protein with a high purity, these methods may be used in combination.

The herbicide-tolerant PPO nucleic acid molecule (polynucleotide encoding the PPO protein or its variant) may be isolated or prepared using standard molecular biological techniques, for example, a chemical synthesis or recombination method, or commercially available one may be used.

In a specific embodiment, the PPO proteins were found to exhibit a broad herbicide tolerance against representative 9 families of PPO inhibiting herbicides classified according to their chemical structures in an herbicide tolerance test system using PPO-deficient *E. coli* BT3($\Delta$PPO). It was also found that they may be also expressed in the chloroplast of a plant by using a transit peptide (TP). Further, it was found that the PPO proteins may be also expressed in *A. thaliana* ecotype Columbia by a plant expression vector. Even though the transformed plants are treated with PPO inhibiting herbicides, germination and growth of the plants are observed. Furthermore, inheritance of the above herbicide-tolerant traits to the next generation was confirmed by an inheritance study.

Therefore, the PPO protein and its variants provided herein may be introduced into a plant or an alga, thereby being used for enhancement of the herbicide tolerance of the plant or an alga.

The herbicide herein refers to an active ingredient that kills, controls, or otherwise adversely modifies the growth of plants or algae. In addition, the herbicide tolerance or herbicide tolerance means that even after treatment of a herbicide which normally kills a normal or wild-type plant or normally inhibits growth thereof, inhibition of the plant growth is weakened or eliminated, compared to that of the normal or wild-type plant, and therefore, the plant continues to grow. The herbicide includes a herbicide inhibiting protoporphyrinogen oxidase (PPO) of a plant or an alga. Such PPO inhibiting herbicide may be classified into pyrimidinediones, diphenyl-ethers, phenylpyrazoles, N-phenylphthalimides, thiadiazoles, oxadiazoles, triazolinones, oxazolidinediones, and other herbicides according to their chemical structures.

As a specific embodiment, the pyrimidinediones herbicide includes butafenacil, saflufenacil, benzfendizone, and tiafenacil, but is not limited thereto.

The diphenyl-ethers herbicide includes fomesafen, oxyfluorfen, aclonifen, acifluorfen, bifenox, ethoxyfen, lactofen, chlomethoxyfen, chlorintrofen, fluoroglycofen-ethyl and halosafen, but not limited thereto.

The phenylpyrazoles herbicide includes pyraflufen-ethyl and fluazolate, but not limited thereto.

The phenylphthalimides herbicide includes flumioxazin, cinidon-ethyl and flumiclorac-pentyl, but not limited thereto.

The phenylesters herbicide includes phenopylate (2,4-dichlorophenyl 1-pyrrolidinecarboxylate) and carbamate analogues of phenopylate (for example, O-phenylpyrrolidino- and piperidinocarbamate analoges (refer to "Ujjana B. Nandihalli, Mary V. Duke, Stephen O. Duke, Relationships between molecular properties and biological activities of O-phenyl pyrrolidino- and piperidinocarbamate herbicides, J. Agric. Food Chem., 1992, 40(10):1993-2000")), etc., but not limited thereto. In one embodiment, the carbamate analogue of phenopylate may be one or more selected from the group consisting of pyrrolidine-1-carboxylic acid phenyl ester (CAS No. 55379-71-0), 1-pyrrolidinecarboxylicacid, 2-chlorophenyl ester (CAS No. 143121-06-6), 4-chlorophenyl pyrrolidine-1-carboxylate (CAS No. 1759-02-0), carbamic acid, diethyl-, 2,4-dichloro-5-(2-propynyloxy)phenyl ester (9CI) (CAS No. 143121-07-7), 1-pyrrolidinecarboxylic acid, 2,4-dichloro-5-hydroxyphenyl ester (CAS No. 143121-08-8), 2,4-dichloro-5-(methoxycarbonyl)phenyl pyrrolidine-1-carboxylate (CAS No. 133636-94-9), 2,4-dichloro-5-[(propan-2-yloxy)carbonyl]phenyl pyrrolidine-1-carboxylate (CAS No. 133636-96-1), 1-piperidinecarboxylic acid, 2,4-dichloro-5-(2-propynyloxy)phenyl ester (CAS No. 87374-78-5), 2,4-dichloro-5-(prop-2-yn-1-yloxy)phenyl pyrrolidine-1-carboxylate (CAS No. 87365-63-7), 2,4-dichloro-5-(prop-2-yn-1-yloxy)phenyl 4,4-difluoropiperidine-1-carboxylate (CAS No. 138926-22-4), 1-pyrrolidinecarboxylic acid, 3,3-difluoro-, 2,4-dichloro-5-(2-propyn-1-yloxy)phenyl ester (CAS No. 143121-10-2), 4-chloro-2-fluoro-5-[(propan-2-yloxy)carbonyl]phenyl pyrrolidine-1-carboxylate (CAS No. 133636-98-3), etc.

The thiadiazoles herbicide includes fluthiacet and thidiazimin, but not limited thereto.

The oxadiazoles herbicide includes oxadiargyl and oxadiazon, but not limited thereto.

The triazolinones herbicide includes carfentrazone, sulfentrazone and azafenidin, but not limited thereto.

The oxazolidinediones herbicide includes pentoxazone, but not limited thereto.

The other herbicide includes pyraclonil, flufenpyr-ethyl and profluazol, but not limited thereto.

The herbicide-tolerant PPO gene provided herein may be introduced into a plant or an alga by various methods known in the art, and preferably, by using an expression vector for plant or alga transformation.

In case of plant transformation, an appropriate promoter which may be included in the vector may be any promoter generally used in the art for introduction of the gene into the plant. For example, the promoter may include an SP6 promoter, a T7 promoter, a T3 promoter, a PM promoter, a maize ubiquitin promoter, a cauliflower mosaic virus (CaMV) 35S promoter, a nopaline synthase (nos) promoter, a figwort mosaic virus 35S promoter, a sugarcane bacilliform virus promoter, a Commelina yellow mottle virus promoter, a light-inducible promoter from the small subunit of ribulose-1,5-bisphosphate carboxylase (ssRuBisCO), a rice cytosolic triosephosphate isomerase (TPI) promoter, an adenine phosphoribosyltransferae (APRT) promoter of *Arabidopsis*, an octopine synthase promoter, and a BCB (blue copper binding protein) promoter, but is not limited thereto.

Further, the vector may include a poly A signal sequence causing polyadenylation of 3'-terminus, and for example, it may include NOS 3'-end derived from a nopaline synthase gene of *Agrobacterium tumefaciens*, an octopine synthase terminator derived from an octopine synthase gene of *Agrobacterium tumefaciens*, 3'-end of protease inhibitor I or II gene of tomato or potato, a CaMV 35S terminator, a rice α-amylase terminator RAmy1 A, and a phaseoline terminator, but is not limited thereto.

In addition, chloroplast-specific promoter, nucleus promoter, constitutive promoter, or inducible promoter may be used for introduction of the gene into the algae as a promoter. The herbicide-tolerant PPO gene or its variant provided herein may be designed in order to operationally link to 5' UTR or 3' UTR, thereby expressing function in nucleus of algae. In addition, the vector may further comprise a transcriptional regulatory sequence which is appropriate to transformation of algae. A recombinant gene conferring herbicide tolerance may be integrated to genome of nucleus or genome of chloroplast in a host alga, but not limited thereto.

In addition, in the vector, a transit peptide required for targeting to chloroplasts may be linked to 5'-end of the PPO gene in order to express the herbicide-tolerant PPO gene in the chloroplasts.

In addition, optionally, the vector may further include a gene encoding selectable marker as a reporter molecule, and example of the selectable marker may include antibiotics (e.g., neomycin, carbenicillin, kanamycin, spectinomycin, hygromycin, bleomycin, chloramphenicol, etc.) or herbicide (glyphosate, glufosinate, phosphinothricin, etc.)-tolerant genes, but is not limited thereto.

Further, the recombinant vector for plant expression may include an *Agrobacterium* binary vector, a cointegration vector, or a general vector which has no T-DNA region but is designed to be expressed in the plant. Of them, the binary vector refers to a vector containing two separate vector systems harboring one plasmid responsible for migration consisting of left border (LB) and right border (RB) in Ti (tumor inducible) plasmid, and the other plasmid for target gene-transferring, and the vector may include a promoter region and a polyadenylation signal sequence for expression in plants.

When the binary vector or cointegration vector is used, a strain for transformation of the recombinant vector into the plant is preferably *Agrobacterium* (*Agrobacterium*-mediated transformation). In this regard, *Agrobacterium tumefaciens* or *Agrobacterium rhizogenes* may be used. In addition, when the vector having no T-DNA region is used, electroporation, particle bombardment, polyethylene glycol-mediated uptake, etc. may be used for introduction of the recombinant plasmid into the plant.

The plant transformed with the gene by the above method may be re-differentiated into a plant through callus induction, rhizogenesis, and soil acclimatization using a standard technique known in the art.

The plant subjected to transformation herein is understood by a meaning including a plant cell (containing a suspension-cultured cell), a protoplast, a callus, a hypocotyl, a seed, a cotyledon, a shoot as well as a mature plant.

Further, the scope of the transformant includes a transformant introduced with the gene as well as a clone or progeny thereof ($T_1$ generation, $T_2$ generation, $T_3$ generation, $T_4$ generation, $T_5$ generation, or any subsequent generations). For example, the transformed plant also includes a plant having the inherited herbicide tolerance traits as sexual and asexual progeny of the plant transformed with the gene provided herein. The scope of the present invention also includes all mutants and variants showing the characteristics of the initial transformed plant, together with all hybridization and fusion products of the plant transformed with the gene provided herein. Furthermore, the scope of the present invention also includes a part of the plant, such as a seed, a flower, a stem, a fruit, a leaf, a root, a tuber, and/or a tuberous root, which is originated from a transformed plant which is transformed in advance by the method of the present invention, or a progeny thereof, and is composed of at least a part of the transformed cells.

The plant, to which the present invention is applied, is not particularly limited to, but includes monocotyledonous or dicotyledonous plants. Further, the plant includes herbaceous plants or woody plants. The monocotyledonous plant may include plants belonging to the family Alismataceae, Hydrocharitaceae, Juncaginaceae, Scheuchzeriaceae, Potamogetonaceae, Najadaceae, Zosteraceae, Liliaceae, Haemodoraceae, Agavaceae, Amaryllidaceae, Dioscoreaceae, Pontederiaceae, Iridaceae, Burmanniaceae, Juncaceae, Commelinaceae, Eriocaulaceae, Gramineae (Poaceae), Araceae, Lemnaceae, Sparganiaceae, Typhaceae, Cyperaceae, Musaceae, Zingiberaceae, Cannaceae, Orchidaceae, but not limited thereto.

The dicotyledonous plant may include plants belonging to the family Diapensiaceae, Clethraceae, Pyrolaceae, Ericaceae, Myrsinaceae, Primulaceae, Plumbaginaceae, Ebenaceae, Styracaceae, Symplocaceae, Symplocaceae, Oleaceae, Loganiaceae, Gentianaceae, Menyanthaceae, Apocynaceae, Asclepiadaceae, Rubiaceae, Polemoniaceae, Convolvulaceae, Boraginaceae, Verbenaceae, Labiatae, Solanaceae, Scrophulariaceae, Bignoniaceae, Acanthaceae, Pedaliaceae, Orobanchaceae, Gesneriaceae, Lentibulariaceae, Phrymaceae, Plantaginaceae, Caprifoliaceae, Adoxaceae, Valerianaceae, Dipsacaceae, Campanulaceae, Compositae, Myricaceae, Juglandaceae, Salicaceae, Betulaceae, Fagaceae, Ulmaceae, Moraceae, Urticaceae, Santalaceae, Loranthaceae, Polygonaceae, Phytolaccaceae, Nyctaginaceae, Aizoaceae, Portulacaceae, Caryophyllaceae, Chenopodiaceae, Amaranthaceae, Cactaceae, Magnoliaceae, Illiciaceae, Lauraceae, Cercidiphyllaceae, Ranunculaceae, Berberidaceae, Lardizabalaceae, Menispermaceae, Nymphaeaceae, Ceratophyllaceae, Cabombaceae, Saururaceae, Piperaceae, Chloranthaceae, Aristolochiaceae, Actinidiaceae, Theaceae, Guttiferae, Droseraceae, Papaveraceae, Capparidaceae, Cruciferae, Platanaceae, Hamamelidaceae, Crassulaceae, Saxifragaceae, Eucommiaceae, Pittosporaceae, Rosaceae, Leguminosae, Oxalidaceae, Geraniaceae, Tropaeolaceae, Zygophyllaceae, Linaceae, Euphorbiaceae, Callitrichaceae, Rutaceae, Simaroubaceae, Meliaceae, Polygalaceae, Anacardiaceae, Aceraceae, Sapindaceae, Hippocastanaceae, Sabiaceae, Balsaminaceae, Aquifoliaceae, Celastraceae, Staphyleaceae, Buxaceae, Empetraceae, Rhamnaceae, Vitaceae, Elaeocarpaceae, Tiliaceae, Malvaceae, Sterculiaceae, Thymelaeaceae, Elaeagnaceae, Flacourtiaceae, Violaceae, Passifloraceae, Tamaricaceae, Elatinaceae, Begoniaceae, Cucurbitaceae, Lythraceae, Punicaceae, Onagraceae, Haloragaceae, Alangiaceae, Cornaceae, Araliaceae, Umbelliferae (Apiaceae), but not limited thereto.

In a specific embodiment, the plant may be one or more selected from the group consisting of food crops such as rice, wheat, barley, corn, soybean, potato, red bean, oat, and sorghum; vegetable crops such as Chinese cabbage, radish, red pepper, strawberry, tomato, watermelon, cucumber, cabbage, oriental melon, pumpkin, welsh onion, onion, and carrot; crops for special use such as Ginseng, tobacco, cotton, soilage, forage, sesame, sugar cane, sugar beet, *Perilla* sp., peanut, rape, grass, and castor-oil plant; fruit trees such as apple tree, pear tree, jujube tree, peach tree, kiwi fruit tree, grape tree, citrus fruit tree, persimmon tree, plum tree, apricot tree and banana tree; woody plants such as pine, palm oil, and Eucalyptus; flowering crops such as rose, Gladiolus, Gerbera, carnation, Chrysanthemum, lily and tulip; and fodder crops such as ryegrass, red clover, orchardgrass, alfalfa, tall fescue and perennial ryegrass, but is not limited thereto. As a specific embodiment, the plant may be one or more selected from the group consisting of dicotyledonous plants such as *Arabidopsis thaliana*, potato, eggplant, tobacco, red pepper, tomato, burdock, crown daisy, lettuce, balloon flower, spinach, chard, sweet potato, celery, carrot, water dropwort, parsley, Chinese cabbage, cabbage, radish, watermelon, oriental melon, cucumber, pumpkin, gourd, strawberry, soybean, mung bean, kidney bean, and pea; and monocotyledonous plants such as rice, wheat, barley, corn, sorghum, etc., but are not limited thereto.

The alga, to which the present invention is applied, is not particularly limited to, but includes Prokaryotic algae or Eukaryotic algae. For example, the alga may be cyanobacteria, green algae, red algae, brown algae, macroalgae, or microalgae.

The cyanobacteria includes Chroococcales phylum (for example, *Aphanocapsa*, Aphanothece, Chamaesiphon, Chondrocystis, Chroococcus, Chroogloeocystis, Crocosphaera, Cyanobacterium, Cyanobium, Cyanodictyon, Cyanosarcina, Cyanothece, Dactylococcopsis, Gloeocapsa, Gloeothece, Halothece, Johannesbaptistia, Merismopedia, Microcystis, Radiocystis, Rhabdoderma, Snowella, *Synechococcus, Synechocystis, Thermosynechococcus*, Woronichinia), Gloeobacteria phylum, Nostocales phylum (for example, Microchaetaceae, Nostocaceae, Rivulariaceae, Scytonemataceae), Oscillatoriales phylum (for example, Arthronema, Arthrospira, Blennothrix, Crinalium, Geitlerinema, Halomicronema, Halospirulina, Hydrocoleum, Jaaginema, Katagnymene, Komvophoron, Leptolyngbya, Limnothrix, Lyngbya, Microcoleus, Oscillatoria, Phormidium, Planktothricoides, Planktothrix, Plectonema, Pseudanabaena, Pseudophormidium, Schizothrix, *Spirulina*, Starria, Symploca, *Trichodesmium*, Tychonema), Pleurocapsales phylum (for example, Chroococcidiopsis, Dermocarpa, Dermocarpella, Myxosarcina, Pleurocapsa, Solentia, Stanieria, Xenococcus), Prochlorales phylum, or Stigonematales phylum (for exmaple, Capsosira, Chlorogloeopsis, Fischerella, Hapalosiphon, Mastigocladopsis, Mastigocladus, Nostochopsis, Stigonema, Symphyonema, Symphonemopsis, Umezakia, Westiellopsis), etc.

As another example of algae, Chlorophyta, *Chlamydomonas, Volvacales, Dunaliella, Scenedesmus, Chlorella*, or Hematococcm may be exemplified.

As other example of algae, *Phaeodactylum tricornutum, Amphiprora hyaline, Amphora* spp., *Chaetoceros muelleri, Navicula saprophila, Nitzschia communis, Scenedesmus dimorphus, Scenedesmus obliquus, Tetraselmis suecica, Chlamydomonas reinhardtii, Chlorella vulgaris, Haematococcus pluvialis, Neochloris oleoabundans, Synechococcus elongatus, Botryococcus braunii, Gloeobacter violaceus, Synechocystis, Thermosynechococcus elongatus, Nannochloropsis oculata, Nannochloropsis salina, Nannochloropsis gaditana, Isochrysis galbana, Botryococcus sudeticus, Euglena gracilis, Neochloris oleoabundans, Nitzschia palea, Pleurochrysis carterae, Tetraselmis chuii, Pavlova* spp., *Aphanocapsa* spp., *Synechocystis* spp., *Nannochloris* spp., etc. may be exemplified. However, it is not limited to kinds listed above, and algae belonging to other various genus and family may be comprised.

The plant or alga introduced with the herbicide-tolerant PPO or its variant provided herein may exhibit tolerance against two or more of PPO inhibiting herbicides.

Therefore, the technology provided herein may be used to control weeds or remove undesired aquatic organisms by using two or more kinds of PPO inhibiting herbicides sequentially or simultaneously.

One embodiment provides a method of controlling weeds in a cropland, comprising a step of providing the cropland with a plant comprising the herbicide-tolerant PPO protein, its variant, or a gene encoding thereof described above, and a step of applying an effective dosage of protoporphyrinogen oxidase-inhibiting herbicide to the cropland.

Another embodiment provides a method of removing an undesired aquatic organism from a culture medium, comprising a step of providing a culture medium with algae comprising the herbicide-tolerant PPO protein, its variant, or a gene encoding thereof described above, and a step of applying an effective dosage of protoporphyrinogen oxidase-inhibiting herbicide to the culture medium.

In addition, the herbicide-tolerant PPO protein, its variant, or a gene encoding thereof provided herein may be used in combination of a second herbicide-tolerant polypeptide or a gene encoding thereof.

Therefore, the plant or alga introduced with the herbicide-tolerant PPO provided herein may exhibit tolerance against two or more of herbicides which are different from each other in mechanism of action. In the present invention, two or more of different herbicides including the PPO inhibiting herbicide, which are different from each other in mechanism of action, may be used sequentially or simultaneously, thereby controlling weeds and/or removing undesired aquatic organisms. Hereinafter, the herbicide which is different from the PPO inhibiting herbicide in the mechanism of action is called "second herbicide".

One embodiment provides a composition for conferring or enhancing herbicide tolerance of plants or algae, comprising the above-described herbicide-tolerant PPO protein, its variant, or a gene encoding thereof; and the second herbicide-tolerant polypeptide or a gene encoding thereof.

Another embodiment provides a transformant having herbicide tolerance of plants or algae, or a clone or progeny thereof, comprising the above-described herbicide-tolerant PPO protein, its variant, or a gene encoding thereof; and the second herbicide-tolerant polypeptide or a gene encoding thereof.

Other embodiment provides a method of preparing plants or algae having herbicide tolerance, comprising a step of transforming algae, or plant cell, protoplast, callus, hypocotyl, seed, cotyledon, shoot, or whole plant with the above-described herbicide-tolerant PPO protein, its variant, or a gene encoding thereof; and the second herbicide-tolerant polypeptide or a gene encoding thereof.

Other embodiment provides a method of controlling weeds in a cropland, comprising a step of providing the cropland with a plant comprising the above-described herbicide-tolerant PPO protein, its variant, or a gene encoding thereof; and the second herbicide-tolerant polypeptide or a gene encoding thereof, and a step of applying an effective dosage of protoporphyrinogen oxidase-inhibiting herbicide to the cropland.

Other embodiment provides a method of removing an undesired aquatic organism from a culture medium, comprising a step of providing a culture medium with algae comprising the herbicide-tolerant PPO protein, its variant, or a gene encoding thereof; and the second herbicide-tolerant polypeptide or a gene encoding thereof, and a step of applying an effective dosage of protoporphyrinogen oxidase-inhibiting herbicide to the culture medium.

For example, the plant or alga further includes the second herbicide-tolerant polypeptide or a gene encoding thereof, thereby having novel and/or enhanced tolerance against the second herbicide.

For example, the second herbicide may include cell division-inhibiting herbicides, photosynthesis-inhibiting herbicides, amino acid synthesis-inhibiting herbicides, plastid-inhibiting herbicides, cell membrane-inhibiting herbicides, and/or any combinations thereof, but is not limited thereto. The second herbicide may be exemplified by glyphosate, glufosinate, dicamba, 2,4-D (2,4-dichlorophenoxyacetic acid), ALS (acetolactate synthase)-inhibiting herbicides (for example, imidazolidinone, sulfonylurea, triazole pyrimidine, sulphonanilide, pyrimidine thiobenzoate, etc.), photosystem II-inhibiting herbicides, phenylurea-based herbicides, plastid-inhibiting herbicides, bromoxynil-based herbicides, and/or any combinations thereof, but is not limited thereto.

For example, the second herbicide-tolerant polypeptide may be exemplified as one or more selected from the group consisting of glyphosate herbicide-tolerant EPSPS (glyphosate tolerant 5-enolpyruvylshikimate-3-phosphate synthase), GOX (glyphosate oxidase), GAT (glyphosate-N-acetyltransferase) or glyphosate decarboxylase; glufosinate herbicide-tolerant PAT (phosphinothricin-N-acetyltransferase); dicamba herbicide-tolerant DMO (dicamba monooxygenase); 2,4-D herbicide-tolerant 2,4-D monooxygenase or AAD (aryloxyalkanoate Dioxygenase); ALS-inhibiting sulfonylurea-based herbicide-tolerant ALS (acetolactate Synthase), AHAS (acetohydroxyacid synthase), or AtAHASL (acetohydroxyacid synthase Large Subunit); photosystem II-inhibiting herbicide-tolerant photosystem II protein D1; phenylurea-based herbicide-tolerant cytochrome P450; plastid-inhibiting herbicide-tolerant HPPD (hydroxylphenylpyruvate dioxygenase); bromoxynil herbicide-tolerant nitrilase; and any combinations thereof, but is not limited thereto.

Further, the gene encoding the second herbicide-tolerant polypeptide may be exemplified as one or more selected from the group consisting of glyphosate herbicide-tolerant cp4 epsps, epsps (AG), mepsps, 2mepsps, goxv247, gat4601 or gat4621 gene; glufosinate herbicide-tolerant bar, pat or pat (SYN) gene; dicamba herbicide-tolerant dmo gene; 2,4-D herbicide-tolerant AAD-1 or AAD-12 gene; ALS-inhibiting sulfonylurea-based herbicide-tolerant ALS, GM-HRA, S4-HRA, ZM-HRA, Csr1, Csr1-1, Csr1-2, SurA or SurB; photosystem II-inhibiting herbicide-tolerant psba gene; phenylurea herbicide-tolerant CYP76B1 gene; isoxaflutole herbicide-tolerant HPPDPF W336 gene; bromoxynil herbicide-tolerant bxn gene; and any combinations thereof, but is not limited thereto.

Advantageous Effects

A variant of herbicide-tolerant PPO protein or a gene encoding thereof provided herein is applied to plants or algae, thereby conferring and/or enhancing more excellent herbicide tolerance traits, and the selective control is performed using herbicides, thereby economically controlling weeds or removing aquatic organisms.

DESCRIPTION OF DRAWINGS

FIG. 1 is the map of pACBB vector.

FIG. 2 shows cell growth level after tiafenacil treatment at a concentration of 0 (micromole), 100 µM, or 400 µM, of PPO-deficient BT3 E. coli transformed with pACBB-eGFP vector control (V), PPO-susceptible Arabidopsis thaliana (A. thaliana) PPO1 gene (AtPPO1 WT), PPO-tolerant A. thaliana PPO1 mutant gene (AtPPO1 SLYM), CyPPO10 gene (Cy10 WT), and CyPPO13 gene (Cy13 WT), respectively.

FIG. 3 is the map of pET303-CT-His vector.

FIG. 4 shows the schematic diagram of a recombinant vector for a fusion protein wherein MBP (maltose binding protein) and PPO protein are fused.

FIG. 5 is the map of pMAL-c2X vector.

FIG. 6 is a schematic diagram exemplarily showing the structure of binary vector for plant transformation of CyPPO genes.

FIG. 7 is the result of western blotting showing the expression level of CyPPO variant proteins in $T_2$ A. thaliana transformed with CyPPO10 variant (F360I variant or F360M variant) or CyPPO13 variant (F373M variant) gene.

FIG. 8 shows the injury level of A. thaliana transformant ($T_3$) transformed with CyPPO10 or CyPPO13 wild type gene when treated with 1 µM of tiafenacil. Col-O means non-transgenic A. thaliana.

FIG. 9 shows the injury level of A. thaliana transformant ($T_2$) transformed with a genes encoding a CyPPO10 variant (F360C, F360I, F360L, F360M, F360V, F360T, A167C, A167L, A167L+F360M, or A167C+F360I) when treated with tiafenacil at a concentration of 1 µM, 5 µM, or 25 µM.

FIG. 10 shows the injury level of A. thaliana transformant ($T_2$) transformed with a gene encoding a CyPPO13 variant (A177C, F373C, F373I, F373M, A177L+F373L, or A177L+F373I) when treated with tiafenacil at a concentration of 1 µM or 10 µM.

FIG. 11 shows cell growth level of PPO-deficient BT3 E. coli (ΔPPO) transformants transformed with CyPPO10 wild type gene (indicated as Cy10 WT), or various CyPPO10 mutant genes, when treated with tiafenacil at a concentration of 0 µM, 5 µM, 25 µM, 50 µM, 100 µM, and 200 µM, respectively.

FIG. 12 shows cell growth level of PPO-deficient BT3 (ΔPPO) transformants transformed with Cy10 WT or various CyPPO10 mutant genes, when treated with saflufenacil at a concentration of 0 µM, 5 µM, 25 µM, 50 µM, 100 µM, and 200 µM, respectively.

FIG. 13 shows cell growth level of PPO-deficient BT3 (ΔPPO) transformants transformed with Cy10 WT or various CyPPO10 mutant genes, when treated with fomesafen at a concentration of 0 µM, 5 µM, 25 µM, 50 µM, 100 µM and 200 µM, respectively.

FIG. 14 shows cell growth level of PPO-deficient BT3 (ΔPPO) transformants transformed with Cy10 WT or various CyPPO10 mutant genes, when treated with acifluorfen at a concentration of 0 µM, 5 µM, 25 µM, 50 µM, 100 µM and 200 µM, respectively.

FIG. 15 shows cell growth level of PPO-deficient BT3 (ΔPPO) transformants transformed with Cy10 WT or various CyPPO10 mutant genes, when treated with flumioxazin at a concentration of 0 µM, 5 µM, 25 µM, 50 µM, 100 µM and 200 µM, respectively.

FIG. 16 shows cell growth level of PPO-deficient BT3 (ΔPPO) transformants transformed with Cy10 WT or various CyPPO10 mutant genes, when treated with sulfentrazone at a concentration of 0 µM, 5 µM, 25 µM, 50 µM, 100 µM and 200 µM, respectively.

FIG. 17 shows cell growth level of PPO-deficient BT3 (ΔPPO) transformants transformed with Cy10 WT or various CyPPO10 mutant genes, when treated with pentoxazone at a concentration of 0 µM, 5 µM, 25 µM, 50 µM, 100 µM and 200 µM, respectively.

FIG. 18 shows cell growth level of PPO-deficient BT3 (ΔPPO) transformants transformed with Cy10 WT or various CyPPO10 mutant genes, when treated with pyraflufen-ethyl at a concentration of 0 µM, 5 µM, 25 µM, 50 µM, 100 µM and 200 µM, respectively.

FIG. 19 shows cell growth level of PPO-deficient BT3 (ΔPPO) transformants transformed with Cy10 WT or various CyPPO10 mutant genes, when treated with pyraclonil at a concentration of 0 µM, 5 µM, 25 µM, 50 µM, 100 µM and 200 µM, respectively.

FIG. 20 shows cell growth level of PPO-deficient BT3 (ΔPPO) transformants transformed with CyPPO13 wild type gene (indicated as Cy13 WT), or various CyPPO13 mutant genes, when treated with tiafenacil at a concentration of 0 µM, 5 µM, 25 µM, and 50 µM, respectively.

FIG. 21 shows cell growth level of PPO-deficient BT3 (ΔPPO) transformants transformed with Cy13 WT or various CyPPO13 mutant genes, when treated with saflufenacil at a concentration of 0 µM, 5 µM, 25 µM, and 50 µM, respectively.

FIG. 22 shows cell growth level of PPO-deficient BT3 (ΔPPO) transformants transformed with Cy13 WT or various CyPPO13 mutant genes, when treated with fomesafen at a concentration of 0 µM, 5 µM, 25 µM, 50 µM, 100 µM and 200 µM, respectively.

FIG. 23 shows cell growth level of PPO-deficient BT3 (ΔPPO) transformants transformed with Cy13 WT or various CyPPO13 mutant genes, when treated with acifluorfen at a concentration of 0 µM, 5 µM, 25 µM, 50 µM, 100 µM and 200 µM, respectively.

FIG. 24 shows cell growth level of PPO-deficient BT3 (ΔPPO) transformants transformed with Cy13 WT or various CyPPO13 mutant genes, when treated with flumioxazin at a concentration of 0 µM, 5 µM, 25 µM, and 50 µM, respectively.

FIG. 25 shows cell growth level of PPO-deficient BT3 (ΔPPO) transformants transformed with Cy13 WT or various CyPPO13 mutant genes, when treated with sulfentrazone at a concentration of 0 µM, 5 µM, 25 µM, 50 µM, 100 µM and 200 µM, respectively.

FIG. 26 shows cell growth level of PPO-deficient BT3 (ΔPPO) transformants transformed with Cy13 WT or various CyPPO13 mutant genes, when treated with pentoxazone at a concentration of 0 µM, 5 µM, 25 µM, 50 µM, 100 µM and 200 µM, respectively.

FIG. 27 shows cell growth level of PPO-deficient BT3 (ΔPPO) transformants transformed with Cy13 WT or various CyPPO13 mutant genes, when treated with pyraflufen-ethyl at a concentration of 0 µM, 5 µM, 25 µM, 50 µM, 100 µM and 200 µM, respectively.

FIG. 28 shows cell growth level of PPO-deficient BT3 (ΔPPO) transformants transformed with Cy13 WT or various CyPPO13 mutant genes, when treated with pyraclonil at a concentration of 0 µM, 5 µM, 25 µM, 50 µM, 100 µM and 200 µM, respectively.

FIG. 29 shows cell growth level of PPO-deficient BT3 (ΔPPO) transformants transformed with Cy13 WT or various CyPPO13 mutant genes, when treated with oxadiazon at a concentration of 0 µM, 5 µM, 25 µM, 50 µM, 100 µM and 200 µM, respectively.

FIG. 30 is the map of pET29b vector.

FIGS. 31a to 31c show the results of seed germination of *A. thaliana* transformant transformed with CyPPO10 or CyPPO13 wild type gene or a mutant gene thereof, at $7^{th}$ days after sowing on ½ MS medium containing various herbicides. Col-0 means non-transgenic *A. thaliana*.

FIG. 32 shows the injury level of *A. thaliana* transformants ($T_3$) transformed with a gene encoding a CyPPO10 variant (F360I, F360L, F360M, A167C+F360I, A167C+F360M, or V305M+F360M) when treated with 25 µM of tiafenacil or 100 µM of saflufenacil. Col-0 means non-transgenic *A. thaliana*.

FIG. 33a shows the injury level of *A. thaliana* transformants ($T_3$) transformed with a gene encoding a CyPPO10 variant (F360I or A167L+F360M), when treated with tiafenacil, saflufenacil, flumioxazin, or sulfentrazone at a concentration of 50 µM, respectively.

FIG. 33b shows the injury level of *A. thaliana* transformants ($T_3$) transformed with a gene encoding a CyPPO13 variant (A177L+F373L or A177L+F373I) when treated with saflufenacil, tiafenacil, flumioxazin, sulfentrazone, oxyfluorfen, or pyraclonil at a concentration of 50 µM, respectively. Col-0 means non-transgenic *A. thaliana*.

FIG. 34 shows the injury level of *A. thaliana* transformants ($T_4$) transformed with CyPPO10 F360I when treated with 15 µM of tiafenacil or 150 µM of saflufenacil.

FIG. 35 shows the injury level of *A. thaliana* transformants ($T_5$) transformed with CyPPO10 F360I when treated with 15 µM of tiafenacil or 150 µM of saflufenacil. Col-0 means non-transgenic *A. thaliana*.

FIG. 36 is a western blot result showing expression of CyPPO10 F360I protein in *A. thaliana* transformants ($T_4$ or $T_5$) transformed with CyPPO10 F360I.

FIG. 37 is the map of pB2GW7.0 binary vector.

FIG. 38 shows the injury level in leaves of $T_0$ soybean transformed with CyPPO10 A167L+F360M mutant gene when treated with 5 µM or 15 µM of tiafenacil. Kwangan soybean means non-transgenic soybean (cultivar).

FIG. 39 provides southern blotting results showing the presence of transgene in CyPPO10 A167L+F360M transformed soybean.

FIG. 40 shows herbicide tolerance of the T1 transgenic soybeans (CyPPO10 A167L+F360M) 5 days after spray treatment with 25 µM tiafenacil or 150 µM saflufenacil. Kwangan soybean means non-transgenic soybean (cultivar).

FIG. 41 shows cell growth level of BT3 (ΔPPO) *E. coli* transformed with a mutant gene of CyPPO10 when cultured in herbicide-containing media.

MODE FOR INVENTION

Hereinafter, the present invention will be described in detail by Examples. However, the following Examples are for illustrative purposes only, and the invention is not intended to be limited by the following Examples.

Example 1. Isolation of PPO Gene from Prokaryote

PPO genes were collected using Genbank data base of *Thermosynechococcus elongatus* BP-1 and *Synechococcus* sp. JA-3-3Ab, and the PPO genes were synthesized with codon-optimized information for efficient herbicide resistance screening in BT3 *E. coli*. The synthesized PPO genes were amplified under the following conditions using primers of Table 1 to clone on pACBB vector.

Fifty microliters (50 µl) of PCR reaction mixture was prepared by mixing 1 µl of template (synthetic DNA of each gene), 5 μl of 10× buffer, 1 μl of dNTP mixture (each 10 mM), 1 μl of a forward primer (refer to Table 1; 10 μM), 1 μl of a reverse primer (refer to Table 1; 10 μM), 40 μl of DDW, and 1 μl of Pfu-X (Solgent, 2.5 unit/μl), and amplification was performed under conditions of at 1 cycle of 94° C. for 4 minutes, 25 cycles of 94° C. for 30 seconds, 56° C. for 30 seconds and 72° C. for 1.5 minutes, and 1 cycle of 72° C. for 5 minutes.

PPO isolated from *Thermosynechococcus elongatus* BP-1 was designated as CyPPO10, and PPO isolated from *Synechococcus* sp. JA-3-3Ab strain was designated as CyPPO13, respectively.

TABLE 1

| Strain | Primer | Sequence | SEQ ID NO: |
|---|---|---|---|
| *Thermosynechococcus elongatus* | CyPPO10_BamHI F | CCCCGGATCCATGATTGAAGTGGATGTGGC | 8 |
| | CyPPO10_XhoI R | CCCCCTCGAGTGATTGTCCACCAGCGAGGT | 9 |
| *Synechococcus* sp. JA-3-3Ab | CyPPO13_BamHI F | CCCCGGATCCATGAACCCTGCTACCCCTGA | 10 |
| | CyPPO13_XhoI R | CCCCCTCGAG CACCTGTGAT AACAACTGCT | 11 |

Example 2. Herbicide Tolerance by CyPPO10 and CyPPO13

The herbicide tolerance by CyPPO10 and CyPPO13 was tested using PPO-deficient *E. coli*.

After transforming PPO-deficient BT3 *E. coli* (ΔPPO) with CyPPO10 or CyPPO13, the transformed BT3 (ΔPPO) was cultured on LB agar plates containing PPO-inhibiting herbicide to examine the growth level of the transformed BT3 (ΔPPO). BT3 (ΔPPO) strain was obtained from Hokkaido University (Japan). The BT3 (ΔPPO) strain is deficient in hemG-type PPO and has kanamycin tolerance (refer to "Watanabe et al., Dual targeting of spinach protoporphyrinogen oxidase II to mitochondria and chloroplasts by alternative use of two in-frame inhibition codons, JBC 2001 276(23):20474-20481; Che et al., Molecular Characterization and Subcellular Localization of Protoporphyrinogen Oxidase in Spinach Chloroplasts, Plant Physiol. 2000 September; 124(1):59-70").

The specific test process was as follows:

CyPPO10 and CyPPO13 genes were cloned in pACBB vector (Plasmid #32551; Addgene; refer to FIG. 1).

Specifically, PCR products amplified in the Example 1 were treated with BamHI and XhoI restriction enzymes (New England Biolabs), and ligated with pACBB-eGFP vector which was treated with the same restriction enzymes.

The treatment of restriction enzymes was conducted under the following conditions:

30 μl (microliter) of PCR product, 0.5 μl of BamHI and XhoI (New England Biolabs) respectively, 4 μl of 10× buffer, and 5.5 μl of water; Restriction enzyme reaction 37° C., 1 hr Ligation reaction was conducted under the following conditions:

0.5 μl of T4 DNA ligase (RBC), 1 μl of A buffer, 1 μl of B buffer, PCR products and vector which were treated with the restriction enzymes, total 10 μl; 22° C., 30 min.

The cloned plasmid was added to 100 μl of BT3 competent cell (Hokkaido University; Japan) respectively, thereby transforming by a heat shock method. The transformed *E. coli* with each PPO gene was cultured in LB (Luria-Bertani) agar media comprising Chloramphenicol (Duchefa).

For seed culture of *E. coli* transformed with respective genes, each single colony of *E. coli* transformant as provided above was cultured in 3 ml of LB broth containing chloramphenicol overnight (220 rpm, 37° C.), and 50 to 100 μl were subcultured in a new 3 ml of LB broth, and they were cultured until absorbance ($OD_{600}$) became 0.5 to 1, and they were diluted with LB broth to absorbance ($OD_{600}$) of 0.5.

The diluted solution was serially diluted again 5 times by a factor of one tenth with LB broth. Thereafter, on the LB agar media (petri dish) containing tiafenacil at the concentration of 0 μM, 100 μM, and 400 μM, 10 μl of each diluted solution was dropped. The LB Agar media were incubated at 37° C., under light condition, and level of inhibiting growth was observed after 16 to 20 hours of incubation.

For comparison, the same test was conducted using BT3 *E. coli* transformant transformed with pACBB-eGFP vector (Plasmid #32551; Addgene; refer to FIG. 1) (V; pACBB-eGFP vector); BT3 *E. coli* transformant transformed with the wild type *Arabidopsis thaliana* (*A. thaliana*) PPO1 gene (AtPPO1 WT, Wild type AtPPO1; PPO susceptible) (SEQ ID NO: 6); and BT3 *E. coli* transformant transformed with a *A. thaliana* mutant PPO1 gene encoding mutated AtPPO1 (AtPPO1 SLYM, SEQ ID NO: 7) amino acid substitutions of Y426M (the 426$^{th}$ amino acid residue, tyrosine, was substituted with methionine) and S305L (the 305$^{th}$ amino acid residue, serine, was substituted with leucine), based on the amino acid sequence of wild type AtPPO1 (SEQ ID NO: 5) (Li et al. Development of protoporphyrinogen oxidase as an efficient selection marker for *Agrobacterium tumefaciens*-mediated transformation of maize. Plant physiol. 2003 133: 736-747).

The obtained result was shown in FIG. 2. As shown in FIG. 2, on a medium containing no herbicide (tiafenacil 0 μM), the growth of BT3 transformant (V) transformed with pACBB-eGFP in which PPO gene was not introduced was not recovered, and the growth of BT3 transformants transformed with PPO susceptible *A. thaliana* PPO1 wild type gene (AtPPO1 WT), PPO tolerant *A. thaliana* PPO1 mutant gene (AtPPO1 SLYM), CyPPO10 gene (Cy10 WT), or CyPPO13 gene (Cy13 WT) was recovered, as each introduced gene functioned as the PPO enzyme in BT3. Such results demonstrate that both of CyPPO10 and CyPPO13 exerted normal PPO function.

BT3 transformant (AtPPO1 WT) transformed with *A. thaliana* PPO1 wild type gene that is susceptible to tiafenacil, normally grew in a medium containing no herbicide (0 µM), but did not grow in a medium containing 100 µM of tiafenacil. BT3 transformant (AtPPO1 SLYM) transformed with *A. thaliana* PPO1 mutant gene that is tolerant to tiafenacil, gradually started to exhibit growth inhibition from 100 µM of tiafenacil and hardly grew at 400 µM. BT3 transformant transformed with CyPPO10 or CyPPO13 gene grew in the medium containing tiafenacil 100 µM at the similar level to that of the medium containing no tiafenacil, and also grew well even in the medium containing tiafenacil 400 µM. From such results, it was demonstrated that CyPPO10 and CyPPO13 gene can exhibit significantly higher tiafenacil tolerance compared to *A. thaliana* PPO1 wild type that is susceptible to tiafenacil, and similar or high level of tiafenacil tolerance compared to *A. thaliana* PPO1 mutant type having tiafenacil tolerance.

Example 3. Determination of PPO Amino Acid Residues Interacting with PPO-Inhibiting Herbicides from PPO and PPO-Inhibiting Herbicide Complex In order to investigate the binding structure information of PPO protein and herbicide, tiafenacil, saflufenacil, flumioxazin, or sulfentrazone were used for test as representative examples of PPO-inhibiting herbicides. A gene encoding CyPPO10 protein was cloned into the pET29b vector (Catalog Number: 69872-3; EMD Biosciences; refer to FIG. 30) and expressed as a CyPPO10 protein using *E. coli* system. The expressed CyPPO10 protein was purified through nickel affinity chromatography, and crystallized with PPO-inhibiting herbicides. Then, using a synchrotron radiation accelerator, X-ray diffraction data of the 2.4 Å resolution of complexes of CyPPO10 and tiafenacil, saflufenacil, flumioxazin, or sulfentrazone were obtained, to identify the three-dimensional structure of the complex. Through such process, information for amino acid mutation position in CyPPO10 proteins conferring herbicide tolerance was collected.

As a result of analysis of structure of CyPPO10 and tiafenacil complex, it was concluded that amino acids of N59, S60, R89, F161, V165, A167, Q184, P303, V305, F324, L327, I340, F360, and I408 of CyPPO10 protein (SEQ ID NO: 2) were interacted with tiafenacil.

Using the binding information derived from the structure of CyPPO10-tiafenacil complex, amino acid residues that interact with tiafenacil in CyPPO13 (SEQ ID NO: 4) protein were identified by sequence homology analysis (NCBI BLAST, http://blast.ncbi.nlm.nih.gov/Blast.cgi?PROGRAM=blastp&PAGE_TYPE=BlastSearch&LINK_LOC=blasthome) between amino acids of CyPPO10 (SEQ ID NO: 2) and CyPPO13.

As a result, it was comprehended that amino acids of R101, F171, V175, A177, G194, P316, V318, F337, L340, I353, and F373 positions of CyPPO13 protein (SEQ ID NO: 4) interacted with tiafenacil.

Example 4. Preparation of PPO Variants

In order to enhance PPO-inhibiting herbicide tolerance of CyPPO10 and CyPPO13, both genes were mutated at the positions of amino acids interacting with herbicides, as identified in the Example 3, thereby preparing the mutated genes for increasing PPO-inhibiting herbicide tolerance.

Mutant PPO genes were isolated and amplified by PCR under the following conditions using primers of Table 3:
Materials
Template (synthetic DNA of CyPPO10 or CyPPO13) 1 µl
10× buffer 5 µl
dNTP mixture (10 mM each) 1 µl
forward primer (10 µM) 1 µl
reverse primer (10 µM) 1 µl
DDW 40 µl
Pfu-X (Solgent, 2.5 unit/μl) 1 μl
Total 50 μl

TABLE 2

| PCR conditions | | |
|---|---|---|
| 94° C. | 4 min | |
| 94° C. | 30 sec | 25 cycles |
| 56° C. | 30 sec | |
| 72° C. | 1.5 min | |
| 72° C. | 5 min | |
| 4° C. | 5 min | |

TABLE 3

| Strain | Primer | Sequence | SEQ ID NO: |
|---|---|---|---|
| *Thermosynechococcus elongatus* BP-1 | CyPPO10_XbaI F | CCCCTCTAGAATGATTGAAGTGGATG TGGC | 12 |
| | CyPPO10_XhoI R | CCCCCTCGAG TGATTGTCCA CCAGCGAGGT | 13 |
| *Synechococcus* sp. JA-3-3Ab | CyPPO13_XbaI F | CCC TCTAGAATG AAC CCT GCT ACC CCT GA | 14 |
| | CyPPO13_XhoI R | CCCCCTCGAG CACCTGTGAT AACAACTGCT | 15 |

The amplified gene products and pET303-CT His vector (VT0163; Novagen; refer to FIG. 3) were cleaved with XbaI and XhoI, and then, pET303-CyPPO10 and pET303-CyPPO13 plasmids were prepared respectively using T4 DNA ligase (RBC, 3 unit/μl).

Mutant genes of CyPPO10 and CyPPO13 were prepared by conducting PCR under the following conditions using primers of following Tables 5 and 6, and using the CyPPO10 and CyPPO13 which were cloned to the pET303-CT His vector as a template.

Materials
Template 1 μl
10× buffer 5 μl
dNTP mixture (10 mM each) 1 μl
forward primer (10 μM) 1 μl
reverse primer (10 μM) 1 μl DDW 40 μl
Pfu-X (Solgent, 2.5 unit/μl) 1 μl
Total 50 μl

TABLE 4

| PCR conditions | |
|---|---|
| 94° C. | 4 min |
| 94° C. | 30 sec |

TABLE 4-continued

| PCR conditions | |
|---|---|
| 56~60° C. | 30 sec |
| 72° C. | 3 min |
| 72° C. | 5 min |
| 4° C. | 5 min |

17~25 cycles

TABLE 5

List of primers for constructing CyPPO13 mutant gene

| Amino acid mutation of CyPPO10 | Primer sequence (5'→ 3') |
|---|---|
| F360M | F: GTT TTT ACC TCT ATG ATA GGA GGT GCT ACT (SEQ ID NO: 16)<br>R: AGC ACC TCC TAT CAT AGA GGT AAA AAC CTG (SEQ ID NO: 17) |
| F360V | F: GTT TTT ACC TCT GTT ATA GGA GGT GCT ACT (SEQ ID NO: 18)<br>R: AGC ACC TCC TAT AAC AGA GGT AAA AAC CTG (SEQ ID NO: 19) |
| F360I | F: GTT TTT ACC TCT ATT ATA GGA GGT GCT ACT (SEQ ID NO: 20)<br>R: AGC ACC TCC TAT AAT AGA GGT AAA AAC CTG (SEQ ID NO: 21) |
| F360T | F: GTT TTT ACC TCT ACT ATA GGA GGT GCT ACT (SEQ ID NO: 22)<br>R: AGC TCC ACC AAT AGT AGA GGT AAA AAC CTG (SEQ ID NO: 23) |
| F360L | F: GTT TTT ACC TCT CTT ATA GGA GGT GCT ACT (SEQ ID NO: 24)<br>R: AGC TCC ACC AAT AAG AGA GGT AAA AAC CTG (SEQ ID NO: 25) |
| F360C | F: GTT TTT ACC TCT TGT ATA GGA GGT GCT ACT (SEQ ID NO: 26)<br>R: AGC TCC ACC AAT ACA AGA GGT AAA AAC CTG (SEQ ID NO: 27) |
| A167C | F: TCAGGAGTGTAC TGT GGAGATCCTCAACAG (SEQ ID NO: 28)<br>R: TTGAGGATCTCC ACA GTACACTCCTGAAAC (SEQ ID NO: 29) |
| A167L | F: TCAGGAGTGTAC CTT GGAGATCCTCAACAG (SEQ ID NO: 30)<br>R: TTGAGGATCTCC AAG GTACACTCCTGAAAC (SEQ ID NO: 31) |
| P303L + V305L | F: ATACCTTAT CTT ACT CTT GCT TGT GTT GTG (SEQ ID NO: 32)<br>R: AACACAAGC AAG AGT AAG ATA AGG TAT (SEQ ID NO: 33) |
| V305M | F: CCTTATCCAACT ATG GCTTGTGTTGTGCTT (SEQ ID NO: 34)<br>R: CACAACACAAGC CAT AGTTGGATAAGGTAT (SEQ ID NO: 35) |
| N59T | F: GAG CTT GGT CCA ACT AGT TTC GCT C (SEQ ID NO: 36)<br>R: AGCGAAACT AGT TGGACCAAGCTCCCA (SEQ ID NO: 37) |
| R89A | F: CAC CTT CCA GCT TAT ATA TAC TGG AGG GGA (SEQ ID NO: 38)<br>R: GTA TAT ATA AGC TGG AAG GTG CCT ATC TCC (SEQ ID NO: 39) |
| V165S | F: GTT TCA GGA TCA TAC GCT GGA GAT CCT CAA CAG (SEQ ID NO: 40)<br>R: TCC AGC GTA TGA TCC TGA AAC AAA TGG TGC CAC (SEQ ID NO: 41) |
| V305T | F: CCTTATCCAACT ACT GCTTGTGTTGTGCTT (SEQ ID NO: 42)<br>R: CACAACACAAGC AGT AGTTGGATAAGGTAT (SEQ ID NO: 43) |
| S60T | F: GGT CCA AAC ACT TTC GCT CCT ACT CCA GCA CTC (SEQ ID NO:44)<br>R: AGG AGC GAA AGT GTT TGG ACC AAG CTC CCA CAC (SEQ ID NO: 45) |
| I340T | F: CTC GGA ACC ACC TGG TCT TCA GCT TTA TTC CCA (SEQ ID NO: 46)<br>R: TGA AGA CCA GGT GGT TCC GAG TGT CCT TAT ACC (SEQ ID NO: 47) |
| R89L | F: CAC CTT CCA CTT TAT ATA TAC TGG AGG GGA (SEQ ID NO: 48)<br>R: GTA TAT ATA AAG TGG AAG GTG CCT ATC TCC (SEQ ID NO: 49) |
| R89V | F: CAC CTT CCA GTT TAT ATA TAC TGG AGG GGA (SEQ ID NO: 50)<br>R: GTA TAT ATA AAC TGG AAG GTG CCT ATC TCC (SEQ ID NO: 51) |
| F161A | F: AGATTGGTGGCACCAGCAGTTTCAGGAGTGTAC (SEQ ID NO: 52)<br>R: GTACACTCCTGAAACTGCTGGTGCCACCAATCT (SEQ ID NO: 53) |
| V165C | F: CCATTTGTTTCAGGA TGCTACGCTGGAGATCCT (SEQ ID NO: 54)<br>R: AGGATCTCCAGCGTAGCATCCTGAAACAAATGG (SEQ ID NO: 55) |

TABLE 5-continued

List of primers for constructing CyPPO13 mutant gene

| Amino acid mutation of CyPPO10 | Primer sequence (5'→ 3') |
|---|---|
| Q184G | F: TTTAGAAGGATTGCTGGACTTGAGAAGTTGGGA (SEQ ID NO: 56)<br>R: TCCCAACTTCTCAAGTCCAGCAATCCTTCTAAA (SEQ ID NO: 57) |
| F324V | F: TCAGTTAGACCTGGAGTTGGTGTTTTGGTGCCT (SEQ ID NO: 58)<br>R: AGGCACCAAAACACCAACTCCAGGTCTAACTGA (SEQ ID NO: 59) |
| L327T | F: CCTGGATTTGGTGTTACCGTGCCTAGAGGACAA (SEQ ID NO: 60)<br>R: TTGTCCTCTAGGCACGGTAACACCAAATCCAGG (SEQ ID NO: 61) |
| A167I | F: TCAGGAGTGTACATTGGAGATCCTCAACAG (SEQ ID NO: 62)<br>R: TTGAGGATCTCCAATGTACACTCCTGAAAC (SEQ ID NO: 63) |
| I408R | F: AGAAGGGCTCGTCCACAATATATCGTTGGTTAC (SEQ ID NO: 64)<br>R: TATTGTGGACGAGCCCTTCTCCAAACCTTC (SEQ ID NO: 65) |
| I408W | F: GGTTTGGAGAAGGGCTTGGCCACAATATATCGTTGG (SEQ ID NO: 66)<br>R: CCAACGATATATTGTGGCCAAGCCCTTCTCCAAACC (SEQ ID NO: 67) |

TABLE 6

List of primers for constructing CyPPO13 mutant gene

| Amino acid mutation of CyPPO13 | Primer sequence (5'→ 3') |
|---|---|
| F373M | F: TCATTTCTCAGT ATG TTAGGAGGTGCTACA (SEQ ID NO: 68)<br>R: AGCACCTCCTAA CAT ACTGAGAAATGAGTG (SEQ ID NO: 69) |
| F373V | F: TCATTTCTCAGT GTT TTAGGAGGTGCTACA (SEQ ID NO: 70)<br>R: AGCACCTCCTAA AAC ACTGAGAAATGAGTG (SEQ ID NO: 71) |
| F373I | F: TCATTTCTCAGT ATT TTAGGAGGTGCTACA (SEQ ID NO: 72)<br>R: AGCACCTCCTAA AAT ACTGAGAAATGAGTG (SEQ ID NO: 73) |
| F373T | F: TCATTTCTCAGT ACT TTAGGAGGTGCTACA (SEQ ID NO: 74)<br>R: AGCACCTCCTAA AGT ACTGAGAAATGAGTG (SEQ ID NO: 75) |
| F373L | F: TCATTTCTCAGT CTT TTAGGAGGTGCTACA (SEQ ID NO: 76)<br>R: AGCACCTCCTAA AAG ACTGAGAAATGAGTG (SEQ ID NO: 77) |
| F373C | F: TCATTTCTCAGT TGT TTAGGAGGTGCTACA (SEQ ID NO: 78)<br>R: AGCACCTCCTAA ACA ACTGAGAAATGAGTG (SEQ ID NO: 79) |
| R101A | F: AAGTTGCCAGCATATATCTACTGGGAGGGTGC (SEQ ID NO: 80)<br>R: AGTAGATATATGCTGGCAACTTTGCATCAGCC (SEQ ID NO: 81) |
| A177C | F: TCA GGA GTT TAT TGT GGA GAT CCT GAT CAA (SEQ ID NO: 82)<br>R: ATC AGG ATC TCC ACA ATA AAC TCC TGA TGT (SEQ ID NO: 83) |
| A177L | F: TCAGGAGTTTAT CTT GGAGATCCTGATCAA (SEQ ID NO: 84)<br>R: ATCAGGATCTCC AAG ATAAACTCCTGATGT (SEQ ID NO: 85) |
| A177I | F: GGAGTTTATATTGGAGATCCTGATCAACTTAG (SEQ ID NO: 86)<br>R: AGGATCTCCAATATAAACTCCTGATGTGAAAG (SEQ ID NO: 87) |
| P316L + V318L | F: ATA CTC TAT CTT CCT CTT GCT GTT GTG GCT (SEQ ID NO: 88)<br>R: CAC AAC AGC AAG AGG AAG ATA GAG TAT TTC (SEQ ID NO: 89) |
| V318L | F: TATCCACCTCTTGCTGTTGTGGCTCTTGCATAC (SEQ ID NO: 90)<br>R: CAACAGCAAGAGGTGGATAGAGTATTTCTGCC (SEQ ID NO: 91) |
| V318M | F: CTC TAT CCA CCT ATG GCT GTT GTG GCT CTT (SEQ ID NO: 92)<br>R: AGC CAC AAC AGC CAT AGG TGG ATA GAG TAT (SEQ ID NO: 93) |
| P316A + V318L | F: ATA CTC TAT GCT CCT CTT GCT GTT GTG GCT (SEQ ID NO: 94)<br>R: CAC AAC AGC AAG AGG AGC ATA GAG TAT TTC (SEQ ID NO: 95) |

TABLE 6-continued

List of primers for constructing CyPPO13 mutant gene

| Amino acid mutation of CyPPO13 | Primer sequence (5'→ 3') |
|---|---|
| F373N | F: TTTCTCAGTAACTTAGGAGGTGCTACAGATGC (SEQ ID NO: 96)<br>R: CCTCCTAAGTTACTGAGAAATGAGTGATAAC (SEQ ID NO: 97) |
| F373H | F: TTTCTCAGTCACTTAGGAGGTGCTACAGATGC (SEQ ID NO: 98)<br>R: CCTCCTAAGTGACTGAGAAATGAGTGATAAC (SEQ ID NO: 99) |
| G194Q | F: GCTTTTCCTAGGGTGGCTCAGCTCGAAGAGAGATACGG (SEQ ID NO: 100)<br>R: CCGTATCTCTCTTCGAGCTGAGCCACCCTAGGAAAAGC (SEQ ID NO: 101) |
| G194K | F: GCTTTTCCTAGGGTGGCTAAACTCGAAGAGAGATACGG (SEQ ID NO: 102)<br>R: CCGTATCTCTCTTCGAGTTTAGCCACCCTAGGAAAAGC (SEQ ID NO: 103) |
| G194R | F: GCTTTTCCTAGGGTGGCTCGTCTCGAAGAGAGATACGG (SEQ ID NO: 104)<br>R: CCGTATCTCTCTTCGAGACGAGCCACCCTAGGAAAAGC (SEQ ID NO: 105) |
| G194E | F: GCTTTTCCTAGGGTGGCTGAACTCGAAGAGAGATACGG (SEQ ID NO: 106)<br>R: CCGTATCTCTCTTCGAGTTCAGCCACCCTAGGAAAAGC (SEQ ID NO: 107) |
| G194M | F: GCTTTTCCTAGGGTGGCTATGCTCGAAGAGAGATACGG (SEQ ID NO: 108)<br>R: CCGTATCTCTCTTCGAGCATAGCCACCCTAGGAAAAGC (SEQ ID NO: 109) |
| F337V | F: CAGCCATTAAGAGGAGTGGGTCATCTCATCCC (SEQ ID NO: 110)<br>R: GGGATGAGATGACCCACTCCTCTTAATGGCTG (SEQ ID NO: 111) |
| L340T | F: GAGGATTTGGTCATACCATCCCTAGGTCTCAAG (SEQ ID NO: 112)<br>R: CTTGAGACCTAGGGATGGTATGACCAAATCCTC (SEQ ID NO: 113) |
| I353T | F: GAACCTTGGGTACTACCTGGGCTTCATGTTTG (SEQ ID NO: 114)<br>R: CAAACATGAAGCCCAGGTAGTACCCAAGGTTC (SEQ ID NO: 115) |
| F171A | F: AGATTGGTGGAGCCTGCTACATCAGGAGTTTAT (SEQ ID NO: 116)<br>R: ATAAACTCCTGATGTAGCAGGCTCCACCAATCT (SEQ ID NO: 117) |
| R101A | F: GATGCAAAGTTGCCAGCTTATATCTACTGGGAG (SEQ ID NO: 118)<br>R: CTCCCAGTAGATATAAGCTGGCAACTTTGCATC (SEQ ID NO: 119) |
| V175C | F: CCTTTCACATCAGGATGTTATGCTGGAGATCCT (SEQ ID NO: 120)<br>R: AGGATCTCCAGCATAACATCCTGATGTGAAAGG (SEQ ID NO: 121) |
| V175L | F: ACATCAGGATTGTATGCTGGAGATCCTGATC (SEQ ID NO: 122)<br>R: TCCAGCATACAATCCTGATGTGAAAGGCTCCAC (SEQ ID NO: 123) |

Example 5. PPO-Inhibiting Herbicide Tolerance of PPO and its Variants

In order to enhance PPO-inhibiting herbicide tolerance of CyPPO10 and CyPPO13, the amino acids interacting with herbicide, as identified in the Example 3, were mutated. After PPO-deficient BT3 E. coli (ΔPPO) was transformed with a PPO gene having such mutation, and then cultured with PPO-inhibiting herbicide, to observe the growth of transformed E. coli, as follows:

The pET303-CyPPO10 or pET303-CyPPO13 plasmids prepared in the Example 4, and plasmids containing each mutant gene, were transformed into BT3 competent cell by a heat shock method, and cultured in a LB agar medium containing ampicillin (100 μg/ml).

For seed culture of BT3 transformants, a single colony thereof was cultured in 3 ml of LB broth (LPSS) containing ampicillin for 12 hours or more, and 50~100 μl of the cultured solution was further cultured until absorbance (OD$_{600}$) reaches 0.5 to 1. Then, the obtained cultured solution was diluted with LB broth to adjust absorbance (OD$_{600}$) to 0.5, and was diluted again 5 times by a factor of one tenth with LB broth.

LB (25 g/L), Bacto agar (12 g/L), ampicillin (100 μg/ml) and various herbicides (0~200 μM) were mixed, to prepare herbicide-containing media.

Ten microliters of the diluted solution were dropped on the herbicide-containing media, and the media were incubated with light for 16-20 hours at 37° C. The growth level and PPO-inhibiting herbicide tolerance of BT3 transformed with each gene were evaluated.

Herbicides used in the test were listed in following Table 7:

TABLE 7

| Family | Herbicide |
|---|---|
| Pyrimidinedione-based herbicides | Tiafenacil |
|  | Saflufenacil |
| Diphenyl ether-based herbicides | Fomesafen |
|  | Acifluorfen |
| N-phenylphthalimides-based herbicides | Flumioxazin |
| Triazolinones-based herbicides | Sulfentrazone |
| Oxazolidinediones-based herbicides | Pentoxazone |
| Phenylpyrazoles-based herbicides | Pyraflufen-ethyl |
| Other herbicides | Pyraclonil |

The herbicide tolerance was evaluated relatively compared to CyPPO wild type, and shown in following Tables 8 to 11 and FIGS. 11 to 29:

TABLE 8

| CyPPO10 mutation | Tiafenacil (up to 200 μM) | Saflufenacil (up to 200 μM) | Acifluorfen (up to 200 μM) | Fomesafen (up to 200 μM) |
|---|---|---|---|---|
| CyPPO10 (wild type) | − | − | − | − |
| F360C | ++++ | ++++ | ++++ | ++++ |
| F360I | ++++ | ++++ | ++++ | ++++ |
| F360L | ++++ | ++++ | ++++ | ++++ |
| F360M | ++++ | ++++ | ++++ | ++++ |
| F360V | ++++ | ++++ | ++++ | ++++ |
| A167C | +++ | + | ++++ | ++++ |
| A167L | ++++ | +++ | ++++ | ++++ |
| P303L + V305L | NT | NT | ++ | + |
| V305M | ++ | + | +++ | ++++ |

NT(Not tested)

TABLE 9

| CyPPO10 mutation | Pentoxazone (up to 200 μM) | Pyraflufen-ethyl (up to 200 μM) | Pyraclonil (up to 200 μM) | Flumioxazin (up to 200 μM) | Sulfentrazone (up to 200 μM) |
|---|---|---|---|---|---|
| CyPPO10 (wild type) | − | − | − | − | − |
| F360C | ++++ | ++++ | ++++ | ++++ | ++++ |
| F360I | ++++ | ++++ | ++++ | ++++ | ++++ |
| F360L | ++++ | ++++ | ++++ | ++++ | ++++ |
| F360M | ++++ | ++++ | ++++ | ++++ | ++++ |
| F360V | ++++ | ++++ | ++++ | NT | ++++ |
| A167C | ++++ | ++++ | ++++ | + | ++ |
| A167L | ++++ | ++++ | ++++ | ++++ | +++ |
| P303L + V305L | ++++ | + | +++ | NT | NT |
| V305M | ++++ | + | +++ | NT | NT |

NT(Not tested)

TABLE 10

| CyPPO13 mutation | Tiafenacil (up to 50 μM) | Saflufenacil (up to 50 μM) | Acifluorfen (up to 200 μM) | Fomesafen (up to 200 μM) | Pentoxazone (up to 200 μM) |
|---|---|---|---|---|---|
| CyPPO13 (wild type) | − | − | − | − | − |
| F373C | +++++ | +++ | +++ | +++ | ++++ |
| F373I | +++++ | +++++ | +++ | +++ | +++++ |
| F373L | +++++ | +++++ | +++ | ++++ | +++++ |
| F373M | +++++ | +++ | +++ | ++++ | +++++ |
| F373T | +++++ | ++++ | ++++ | ++++ | ++++ |
| A177C | NT | + | ++++ | ++++ | ++++ |
| A177L | ++ | + | ++++ | ++++ | ++++ |
| V318M | NT | NT | +++ | ++ | + |
| P316A + V318L | NT | NT | +++ | − | NT |
| P316L + V318L | NT | NT | +++ | ++ | NT |

NT(Not tested)

TABLE 11

| CyPPO13 mutation | Pyraflufen-ethyl (up to 200 μM) | Pyraclonil (up to 200 μM) | Sulfentrazone (up to 200 μM) | Flumioxazin (up to 50 μM) |
|---|---|---|---|---|
| CyPPO13 | − | − | − | − |
| F373C | ++ | +++++ | − | − |
| F373I | ++ | +++++ | ++++ | ++++ |

TABLE 11-continued

| CyPPO13 mutation | Pyraflufen-ethyl (up to 200 μM) | Pyraclonil (up to 200 μM) | Sulfentrazone (up to 200 μM) | Flumioxazin (up to 50 μM) |
|---|---|---|---|---|
| F373L | ++ | +++++ | ++++ | ++++ |
| F373M | ++ | +++++ | ++++ | +++ |
| F373T | ++++ | ++++ | + | ++++ |
| A177C | +++++ | ++++ | ++++ | − |
| A177L | +++++ | +++ | ++++ | ++++ |
| V318M | ++ | − | + | NT |
| P316A + V318L | + | − | − | NT |
| P316L + V318L | + | − | + | NT |

NT(Not tested)

In the Tables 8 to 11, the level of herbicide tolerance of the wild type was represented by "−", and the level of herbicide tolerance was graduated by representing the equal level of tolerance by "−", and if higher, adding "+" to the max "+++++".

FIGS. 11 to 19 (wild type and variants of CyPPO10) and FIGS. 20 to 29 (wild type and variants of CyPPO13) show the results of culturing E. coli transformed with CyPPO genes (wild type and variant type), and the concentration described on the top is concentration of herbicide treated. Six columns of each concentration were sequentially diluted 5 times by a factor of one tenth with the E. coli culture solution to the right, and the most left column is the result of E. coli culture solution OD600=0.5.

As shown in Tables 8 to 11 and FIGS. 11 to 29, it was demonstrated that all the transformants transformed with mutant genes of CyPPO10 and CyPPO13 exhibited equal level or increased level of herbicide tolerance to various kinds of herbicides, compared to the transformant with wild type gene.

Example 6: Measurement of Enzyme Activity and IC$_{50}$ Value by Herbicides of PPO The enzyme activities of PPO protein and PPO protein variants were examined, and inhibition assay by PPO-inhibiting herbicides was conducted. It was confirmed that the PPO protein has low water-solubility, but in case of being expressed as a fusion protein with MBP (maltose binding protein) (MBP-PPO), the PPO protein is able to be stably expressed as water-soluble form. Therefore, the wild type and variant proteins which were expressed in the form of fusion protein with MBP were used in the present test (refer to FIG. 4).

In order to express wild type genes and mutant genes of CyPPO10 and CyPPO13 (refer to Example 1 and Example 4), those genes were introduced to pMAL-c2X vector (refer to FIG. 5) respectively, and then cloned to BL21 (DE3) E. coli (CodonPlus).

The transformed E. coli were cultured under the following conditions to express introduced PPO genes:

Induction: OD$_{600}$=0.2, addition of IPTG to 0.3 mM final concentration;

Expression temperature: 23° C., 200 rpm shaking culture;

Expression time: 16 hrs;

Culture scale: 200 ml/1,000 ml flask.

Cell lysis and protein extraction were performed by the following process to the cultured E. coli cells:

Extraction buffer: Column buffer (50 mM Tris-Cl, pH8.0, 200 mM NaCl) 5 ml buffer/g cell;

Sonication: SONICS&MATERIALS VCX130 (130 watts);

15 sec ON, 10 sec OFF for 5 min on ice;

Centrifugation under the condition of 4° C. for 20 minutes (20,000×g); and the supernatant obtained by the centrifugation was diluted at the ratio of 1:6 using column buffer.

The following process for purification of PPO protein was performed in a 4° C. cold room. Amylose resin (New England Biolabs) was packed to 1.5×15 cm column (Bio-Rad Econo Columns 1.5×10 cm, glass chromatography column, max. vol), and the obtained protein extracts were loaded to the column at a flow rate of 0.2 ml/min. The column was washed with 3 column volumes of buffer, and the amount of protein in the washing solution was checked. When the protein was no longer detected, the washing was terminated. Then, the MBP-PPO protein was eluted with approximately 2 column volumes of buffer containing 20 mM maltose. The protein concentration of each eluent was determined and the elution was stopped when the protein was no longer detected. Ten microliter of each fraction was investigated for protein quantification and SDS-PAGE analysis. The highly pure fractions with PPO proteins were taken for enzyme activity assay.

The enzyme activity of the purified wild type protein and variant proteins of CyPPO10 and CyPPO13 was measured by the following process.

At first, a substrate of PPO protein, Protoporphyrinogen IX was synthesized. This process was performed in the space where nitrogen gas is streamed. 6 mg of protoporphyrin IX was dissolved in 20% (v/v) EtOH 20 ml, and stirred under dark condition for 30 minutes. The obtained protoporphyrinogen IX solution was put into a 15 ml screw tube in an amount of 800 and flushed with nitrogen gas for 5 minutes. To this, 1 g of sodium amalgam was added and vigorous shaking was performed for 2 minutes. The lid was open to exhaust hydrogen gas in the tube. Thereafter, the lid was closed and incubated for 3 minutes. The protoporphyrin IX solution was filtered using syringe and cellulose membrane filter. To 600 μl of the obtained protoporphyrin IX solution, 2M MOPS [3-(N-morpholino)propanesulfonic acid] was added in an amount of approximately 300 thereby adjusting pH to 8.0. To determine the enzyme activity of PPO protein, a reaction mixture was prepared with the following composition (based on 10 ml): 50 mM Tris-Cl (pH 8.0); 50 mM NaCl; 0.04% (v/v) Tween 20; 40 mM glucose (0.072 g); 5 units glucose oxidase (16.6 mg); and 10 units catalase (1 μl).

Two hundred microliters (200 μl) of reaction mixture containing a purified PPO protein were placed in 96 well plates, and preincubated for 30 min at room temperature to reduce the oxygen concentration by the reaction of glucose oxidase-catalase. The mineral oil was layered and then the reaction was initiated by adding the substrate, protoporphyrin IX solution, to a final concentration of 50 μM. The reaction proceeded at room temperature for 30 min and the fluorescence of protoporphyrin IX was measured using Microplate reader (Sense, Hidex) (excitation: 405 nm; emission: 633 nm). To calculate the PPO enzyme activity, protoporphyrinogen IX solution was kept open in the air to oxidize the solution (overnight). To this, 2.7N HCl was added, and the absorbance at 408 nm was measured. A standard curve was generated using standard protoporphyrin IX, and the PPO activity was measured by calibration of protoporphyrin IX using the standard curve of protoporphyrin IX.

The enzyme activity of the obtained PPO wildtype and variants was shown in Table 12.

Meanwhile, Michaelis-Menten constant (Km) and the maximal velocity (Vmax) values of each enzyme were calculated in order to evaluate the kinetic parameters of PPO proteins (CyPPO10 and CyPPO13). The initial reaction velocity was measured where the reaction velocity was proportional to substrate concentration, and the amount of produced protoporphyrin IX which is an enzymatic reaction product was measured by time course at room temperature for 20 minutes. Km and Vmax values were calculated with the enzyme kinetics analysis program by Michaelis-Menten equation, and the plant PPO was used as a control group. The obtained result was shown in Table 12:

TABLE 12

| Classification | CyPPO10 | CyPPO13 | AtPPO1 | *Amaranthus* PPO1 |
|---|---|---|---|---|
| Vmax (μM mg protein$^{-1}$ min$^{-1}$) | 949.1 ± 64 | 341.4 ± 14 | 134.4 ± 19 | 57 ± 7 |

As shown in Table 12, CyPPO10 and CyPPO13 have superior ability as a PPO enzyme than *A. thaliana* PPO1 (AtPPO1) and *Amaranthus* PPO1.

The concentration of the PPO-inhibiting herbicides that inhibits the PPO enzyme activity by 50% ($IC_{50}$) was measured for each herbicide. The final concentration of each herbicide was as follows:

0, 10, 50, 100, 250, 500, 1,000, 2,500, 5,000 nM

The $IC_{50}$ value was calculated as the concentration of the herbicide inhibiting the PPO enzyme activity to 50% before adding the herbicide at the above concentration to the above enzyme activity measurement process.

The $IC_{50}$ values of different herbicides were shown in the following Table 13.

TABLE 13

| | | | $IC_{50}$(nM) | | | | | |
|---|---|---|---|---|---|---|---|---|
| No. | Mutation | Activity (%) | Tiafenacil | Saflufenacil | Fomesafen | Butafenacil | Flumioxazin | Sulfentrazone |
| | | | CyPPO10 | | | | | |
| 1 | WT | 100 | 21 | 9 | 15 | 8 | NT | NT |
| 2 | F360M | 93 | 115 | 1,500 | 114 | 24 | NT | NT |
| 3 | F360I | 67 | 799 | 3,916 | 191 | 268 | 3,323 | NT |
| 4 | F360L | 59 | 172 | NT | NT | NT | NT | NT |
| 5 | F360V | 56 | 307 | NT | NT | NT | NT | NT |
| 6 | N59T + F360V | 62 | 543 | NT | NT | NT | NT | NT |
| 7 | R89A + F360M | 67 | 931 | 5,000 | 5,000 | 674 | 1,216 | 5,000 |
| 8 | R89A + F360I | 38 | 2,153 | 5,000 | 5,000 | 1,323 | 5,000 | 5,000 |
| 9 | R89A + F360L | 30 | 1,000 | NT | NT | NT | 1,025 | NT |
| 10 | V165S + F360M | 78 | 435 | NT | NT | NT | 119 | NT |
| 11 | V165S + F360I | 63 | 818 | NT | NT | NT | NT | NT |
| 12 | V165S + F360L | 59 | 470 | NT | NT | NT | NT | NT |
| 13 | V165S + F360V | 52 | 929 | NT | NT | NT | NT | NT |
| 14 | A167L + F360M | 80 | 5,000 | 5,000 | 3,000 | 4,000 | 5,000 | 5,000 |
| 15 | A167L + F360I | 32 | 5,000 | NT | NT | NT | NT | NT |
| 16 | A167C + F360M | 90 | 4,500 | 5,000 | 1,900 | 2,500 | 4,000 | 5,000 |
| 17 | A167C + F360I | 48 | 4,500 | NT | NT | NT | NT | NT |
| 18 | V305M + F360M | 87 | 356 | 5,000 | 675 | 121 | 544 | 2,057 |
| 19 | V305T + F360I | 10 | 276 | NT | NT | NT | NT | NT |
| 20 | R89A + V305T + F360M | 5 | 741 | NT | NT | NT | NT | NT |
| 21 | S60T + V165S + F360M | 17 | 2,720 | NT | NT | NT | NT | NT |
| 22 | S60T + V165S + F360I | 12 | 3,580 | NT | NT | NT | NT | NT |
| 23 | S60T + I340T + F360I | 5 | 2,000 | NT | NT | NT | NT | NT |
| 24 | R89V + F360I | 57 | 242 | NT | NT | NT | NT | NT |

TABLE 13-continued

| | | | IC$_{50}$(nM) | | | | | |
|---|---|---|---|---|---|---|---|---|
| No. | Mutation | Activity (%) | Tiafenacil | Saflufenacil | Fomesafen | Butafenacil | Flumioxazin | Sulfentrazone |
| 25 | R89L + F360I | 51 | 184 | NT | NT | NT | NT | NT |
| 26 | A167I + F360M | 85 | 5,000 | 5,000 | 5,000 | 5,000 | 5,000 | 5,000 |
| 27 | V165C + F360M | 93 | 2,169 | NT | NT | NT | NT | NT |
| 28 | V305L + F360M | 82 | 262 | NT | NT | NT | NT | NT |
| 29 | V165C + A167C + F360M | 91 | 5,000 | 5,000 | 3,034 | 2,810 | 5,000 | 5,000 |
| 30 | V165C + A167I + F360M | 75 | 5,000 | 5,000 | 3,741 | 5,000 | 5,000 | 5,000 |
| 31 | V165C + A167L + F360M | 83 | 5,000 | 5,000 | 4,277 | 4,820 | 5,000 | 5,000 |
| 32 | R89A + A167L + F360M | 7 | 5,000 | NT | NT | NT | NT | NT |
| 33 | I408R + F360M | 5 | 5,000 | NT | NT | NT | NT | NT |
| 34 | I408W + F360M | 5 | 5,000 | NT | NT | NT | NT | NT |
| 35 | R89A | 83 | 104 | NT | NT | NT | NT | NT |
| 36 | F161A | 92 | 203 | NT | NT | NT | NT | NT |
| 37 | V165C | 99 | 97 | NT | NT | NT | NT | NT |
| 38 | A167C | 98 | 86 | NT | NT | NT | NT | NT |
| 39 | A167L | 95 | 792 | NT | NT | NT | NT | NT |
| 40 | Q184G | 97 | 79 | NT | NT | NT | NT | NT |
| 41 | V305M | 100 | 186 | NT | NT | NT | NT | NT |
| 42 | F324V | 59 | 140 | NT | NT | NT | NT | NT |
| 43 | L327T | 84 | 214 | NT | NT | NT | NT | NT |
| 44 | I340T | 19 | 216 | NT | NT | NT | NT | NT |
| 45 | F360T | 85 | 5,000 | NT | NT | NT | NT | NT |
| | | | | CyPPO13 | | | | |
| 1 | WT | 100 | 28 | 36 | 30 | 37 | NT | NT |
| 2 | F373M | 98 | 56 | 481 | 77 | 18 | NT | NT |
| 3 | F373I | 83 | 135 | 1,480 | NT | NT | NT | NT |
| 4 | F373L | 82 | 141 | 1,470 | NT | NT | NT | NT |
| 5 | F373C | 86 | 212 | NT | NT | NT | NT | NT |
| 6 | F373V | 83 | 339 | NT | NT | NT | NT | NT |
| 7 | F373T | 81 | 818 | NT | NT | NT | NT | NT |
| 8 | F373H | 26 | 114 | NT | NT | NT | NT | NT |
| 9 | F373N | 40 | 40 | NT | NT | NT | NT | NT |
| 10 | R101A + F373M | 55 | 615 | 5,000 | NT | NT | 573 | NT |
| 11 | A177C + F373M | 77 | 336 | 4,500 | NT | NT | NT | NT |
| 12 | A177I + F373M | 75 | 261 | 4,700 | NT | NT | NT | NT |
| 13 | A177L + F373M | 75 | 1,122 | 5,000 | 690 | 2,500 | 5,000 | 5,000 |
| 14 | A177L + F373I | 66 | 1,630 | 5,000 | 315 | 5,000 | 5,000 | 5,000 |
| 15 | A177L + F373L | 68 | 5,000 | 5,000 | 464 | 5,000 | 5,000 | 5,000 |
| 16 | V175L + F373M | 93 | 203 | 1,375 | NT | NT | NT | NT |
| 17 | V318M + F373M | 72 | 386 | 1,924 | NT | NT | NT | NT |
| 18 | A177L + F373T | 62 | 4,700 | 5,000 | 3,000 | 4,000 | 5,000 | 5,000 |
| 19 | A177L + F373V | 49 | 5,000 | 5,000 | 1,229 | 5,000 | 5,000 | 5,000 |
| 20 | A177C + F373T | 80 | 3,900 | NT | NT | NT | NT | NT |
| 21 | A177C + F373V | 56 | 3,200 | NT | NT | NT | NT | NT |
| 22 | G194E + F373M | 32 | 64 | 261 | NT | NT | 66 | NT |
| 23 | G194Q + F373M | 37 | 24 | 265 | NT | NT | 5.2 | NT |
| 24 | G194M + F373M | 43 | 20 | 475 | NT | NT | 53 | NT |
| 25 | G194K + F373M | 41 | 95 | 224 | NT | NT | 128 | NT |
| 26 | G194R + F373M | 35 | 67 | 218 | NT | NT | 81 | NT |
| 27 | R101A | 87 | 139 | NT | NT | NT | NT | NT |
| 28 | F171A | 70 | 70 | NT | NT | NT | NT | NT |
| 29 | V175C | 94 | 57 | NT | NT | NT | NT | NT |
| 30 | A177C | 98 | 113 | NT | NT | NT | NT | NT |
| 31 | A177L | 97 | 211 | NT | NT | NT | NT | NT |
| 32 | V318M | 81 | 211 | NT | NT | NT | NT | NT |
| 33 | F337V | 88 | 158 | NT | NT | NT | NT | NT |
| 34 | E340T | 83 | 443 | NT | NT | NT | NT | NT |
| 35 | I353T | 62 | 280 | NT | NT | NT | NT | NT |

NT(Not Tested)

As shown in Table 13, CyPPO protein variants exhibit more increased IC$_{50}$ values, compared to wild type CyPPO protein. Such results demonstrate that the amino acid mutations at certain positions of PPO protein can lead to increase in herbicide tolerance. Although the present data showed that CyPPO protein variants have reduced enzyme activity compared to the wild type, it might be caused by the different conditions of the protein folding, and/or hydrophobicity of recombinants PPOs compared to the native PPOs. While the native PPOs are hydrophobic and localize to the membranes of chloroplasts in plants, the recombinant PPOs produced in E. coli are hydrophilic containing a MBP as a fusion partner. Thus, when PPO variants are properly assembled and localized in chloroplasts membrane of plants, the enzyme activity would not be affected dr

Example 7. Generation of *A. thaliana* Transformants Using CyPPO and its Variants and PPO-Inhibiting Herbicide Tolerance Test

7-1. Construction of *A. thaliana* Transformation Vectors and Transformation of *A. thaliana*

*A. thaliana* was transformed with a binary vector having ORF of a selectable marker, bar gene (glufosinate-tolerant), and that of each encoding gene of CyPPO10 or CyPPO13 variants. The transgenic plant was examined for cross-tolerance towards glufosinate and PPO-inhibiting herbicides. The bar gene was also used to examine whether the transgene was stably inherited during generations. NOS promoter and E9 terminator were used for bar gene expression.

In order to express CyPPO10, CyPPO10 variants, CyPPO13 and CyPPO13 variants, respectively in a plant, CaMV35S promoter and NOS terminator were used. Encoding genes of CyPPO10, CyPPO10 variants, CyPPO13 and CyPPO13 variants were cloned using XhoI and BamHI restriction enzymes. For identification of expressed protein, hemagglutinin (HA) tag was fused to the 3'-terminal region using BamHI and SacI restriction enzymes. NOS terminator was inserted after HA tag, thereby terminating transcription of PPO gene. In addition, in order to transit proteins to chloroplast, transit peptide (TP) of AtPPO1 gene (SEQ ID NO: 10) was inserted in front of 5' of the inserted gene using XbaI and XhoI restriction enzymes. The transit peptide region inserted in the vector was represented by SEQ ID NO: 27 and the inserted HA tag sequence was represented by SEQ ID NO: 28. A schematic diagram of the plant transformation binary vector is shown in FIG. 6.

Each constructed vector above was introduced to *Agrobacterium tumefaciens* GV3101 competent cell by a freeze-thaw method. To prepare *Agrobacterium* GV3101 competent cell, *Agrobacterium* GV3101 strain was seed-cultured in 5 ml LB media under the condition of 30° C. and 200 rpm for 12 hrs. The culture medium was inoculated to 200 ml LB media, and then cultured at 200 rpm for 3-4 hrs at 30° C., and centrifuged at 3000×g for 20 minutes at 4° C. The pellet was washed with sterile distilled water, and resuspended in 20 ml LB media. Snap frozen 200 μl aliquots with liquid nitrogen were stored in a deep freezer.

Each transformed *Agrobacterium* was cultured in an antibiotic medium (LB agar containing spectinomycin) and screened. The screened colony was liquid cultured in LB broth. After *Agrobacterium* was harvested from the culture medium, it was resuspended in 5% (w/v) sucrose, 0.05% (v/v) Silwet L-77 solution (Momentive performance materials company) at an absorbance ($OD_{600}$) of 0.8. By Floral dipping method, Col-0 ecotype *A. thaliana* wild type was transformed, and then the seed ($T_1$) was harvested 1-2 months later.

Bar gene in the binary vector was used for screening of individual transformants. The obtained $T_1$ seeds were sown in ½ MS media (2.25 g/L MS salt, 10 g/L sucrose, 7 g/L Agar) supplemented with 25 μM glufosinate, and the surviving plants were selected after 7 days of sowing, and transplanted into soil.

In order to examine PPO-inhibiting herbicide tolerance of the transgenic plants, 4-week-old plants were evenly sprayed with 100 ml of 1 μM tiafenacil solution (0.05% Silwet L-77) per 40×60 cm area (0.24 m²). While wild type *A. thaliana* (Col-0 ecotype; Columbia-0 ecotype) completely died within 7 days after treatment, each transformant showed no damage to PPO-inhibiting herbicide treatment.

The $T_2$ seeds harvested from surviving plants were sown to ½ MS media (2.25 g/L MS salt, 10 g/L sucrose, 7 g/L Agar) supplemented with 25 μM glufosinate, and after 1 week, surviving plants were transplanted into soil.

To confirm the copy number of each line, the segregation ratios were investigated with $T_2$ seeds.

Tiafenacil tolerance of 4-week-old transformants was confirmed by spraying 100 ml of tiafenacil solution (1 μM, 5 μM, 10 μM or 25 μM tiafenacil+0.05% Silwet L-77) per 40×60 cm area (0.24 m²). $T_3$ seeds were harvested from tiafenacil-tolerant $T_2$ plants.

The seeds were selected in a ½ MS medium containing 25 μM glufosinate, and the lines in which all individuals were glufosinate-tolerant were judged as homolines.

7-2. Seed Germination

Herbicide tolerance of *A. thaliana* transformants introduced with wild type or variant genes of CyPPO10 and CyPPO13 was confirmed.

$T_3$ generation seeds of each transformant were sown in ½ MS media containing herbicides. Col-0 ecotype (wild type *Arabidopsis*) seeds were used as a control. The kinds of herbicides and concentration are as follows:

FIG. 31a: 25 μM gufosinate (PPT), 70 nM tiafenacil, 100 nM saflufenacil, 25 μM glufosinate+70 nM tiafenacil, or 25 μM glufosinate+30 nM tiafenacil+40 nM saflufenacil;

FIGS. 31b and 31c: 25 μM glufosinate (PPT), 0.1 μM or 1 μM tiafenacil, 0.3 μM or 3 μM saflufenacil, 0.1 μM or 1 μM flumioxazin, 0.5 μM or 5 μM pyraclonil, or 1 μM or 10 μM sulfentrazone.

The results of seed germination in 7 days after sowing were shown in FIGS. 31a, 31b, and 31c. In FIGS. 31a to 31c, 10-3 refers to CyPPO10 wild type, 10FM-4-7 to the CyPPO10 F360M transgenic line, 10FL-1-9 to the CyPPO10 F360L transgenic line, 10FC-3-5 to the CyPPO10 F360C transgenic line, 10AC-5-4 to the CyPPO10 A167C transgenic line, 13-1 to CyPPO13 wild type, 13FM-3-1 to the CyPPO13 F373M transgenic line, 13FC-1-1 to the CyPPO13 F373C transgenic line, 13FI-2-1 to the CyPPO13 F373I transgenic line, 13AC-1-3 to the CyPPO13 A177C transgenic line, CyPPO13_ALFL to the CyPPO13 A177L+F373L transgenic line, and CyPPO13_ALFI to the CyPPO13 A177L+F373I transgenic line, respectively.

As shown in FIGS. 31a to 31c, while the wild type *A. thaliana* (Col-0 ecotype) germinated in the ½ MS medium containing no herbicide, it did not germinate in the ½ MS medium containing herbicides. Therefore, germination test on the medium containing herbicides is useful to evaluate herbicide tolerance.

Meanwhile, transformed *A. thaliana* $T_3$ lines in which CyPPO10 wild type, CyPPO10 mutant genes (F360M, F360I, F360L, F360C, A167C), CyPPO13 wild type or CyPPO13 mutant genes (F373M, F373C, F373I, A177C, A177L+F373L, A177L+F373I) germinated in the media containing herbicides (containing 25 μM glufosinate, 25 μM glufosinate+70 nM tiafenacil, or 25 μM glufosinate+30 nM tiafenacil+40 nM saflufenacil). These results indicate that bar gene (glufosinate-tolerant gene) and CyPPO genes (PPO-inhibiting herbicide-tolerant gene) functioned as herbicide tolerant traits simultaneously and independently in the transgenic plants.

As shown in 31a to 31c, in the media containing various kinds and various concentrations of PPO-inhibiting herbicides, the transformed *A. thaliana* normally germinated and survived, while Col-0 did not normally germinate. Such result showed that transformed *A. thaliana* was conferred tolerance or retained enhanced tolerance to various PPO-inhibiting herbicides by the inserted genes of transformants.

7-3. Investigation of CyPPO Protein Expression in CyPPO Genes-Introduced *A. thaliana* (T$_2$)

Each protein expression was investigated in *A. thaliana* transformants (T$_2$) in which genes encoding CyPPO10, CyPPO10 variants (F360I or F360M), CyPPO13, or CyPPO13 variant (F373M) were inserted, respectively.

Four-week-old *A. thaliana* transformant leaves were ground with liquid nitrogen, and the protein was extracted by adding protein extraction buffer (0.05 M Tris-Cl pH7.5, 0.1 M NaCl, 0.01 M EDTA, 1% Triton X-100, 1 mM DTT). Then, western blotting was conducted using anti-HA antibody (Santa cruz). The expressed proteins in the transformants were detected using HA tag. To compare the amount of proteins loaded, the amount of RuBisCO large subunit was confirmed by Coomassie blue staining. Two independent lines per each variant were tested, and Col-0 was used as a control.

The result was shown in FIG. 7. All the *A. thaliana* transformants introduced with CyPPO10 variant (F360I variant or F360M variant) or CyPPO13 variant (F373M variant) genes exhibited successful expression of the PPO proteins.

7-4. Verification of Herbicide Tolerance of Transformed *A. thaliana* (T$_2$ or T$_3$)

Herbicide tolerance was tested with *A. thaliana* transformants (T$_2$ or T$_3$) in which genes encoding CyPPO10, CyPPO10 variant (F360C, F360I, F360L, F360M, F360V, F360T, A167C, A167L, A167L+F360M, A167C+F360M, A167C+F360I, or V305M+F360M), CyPPO13, or CyPPO13 variant (A177C, F373C, F373I, F373M, A177L+F373I, or A177L+F373L) were introduced respectively.

After treatment with tiafenacil solution (1 µM tiafenacil+ 0.05% (v/v) Silwet L-77) to CyPPO10 or CyPPO13 transformants (T$_3$) in the amount of 100 ml per 40×60 cm area (0.24 m$^2$), injury level of the plant was judged at the 7$^{th}$ day. For comparison, the same test was conducted using the wild type *A. thaliana* (Col-0 ecotype).

The result was shown in FIG. 8.

In addition, after treatment with 100 ml of tiafenacil solution (1 µM, 5 µM, 10 µM, or 25 µM tiafenacil+0.05% (v/v) Silwet L-77) per 40×60 cm area (0.24 m$^2$) to transformants (T$_2$) with genes encoding CyPPO10 variant (F360C, F360I, F360L, F360M, F360V, F360T, A167C, A167L, A167L+F360M, or A167C+F360I) or CyPPO13 variant (A177C, F373C, F373I, F373M, A177L+F373I, or A177L+F373L), injury level of the plant was judged at the 7$^{th}$ day.

The result was shown in FIG. 9 (CyPPO10 variant gene-introduced T$_2$ transformants) and FIG. 10 (CyPPO13 variant gene-introduced T$_2$ transformants).

In addition, the injury level (Injury index) of each line after tiafenacil treatment in FIGS. 8 to 10 was shown in the following Table 14 as numerical index.

TABLE 14

T$_2$ Injury Index (injury level)

| | Line No. | Tiafenacil | Average injury index |
|---|---|---|---|
| Col-0 | | 1 µM | 5 |
| CyPPO10 | | | |
| Wild type | | 1 µM | 0.5 |
| F360C | 3 | 1 µM | 0.3 |
| | | 5 µM | 0.9 |
| F360I | 7 | 1 µM | 0 |
| | | 5 µM | 0.1 |
| F360L | 3 | 1 µM | 0 |
| | | 5 µM | 0.3 |
| F360M | 4 | 1 µM | 0.1 |
| | | 5 µM | 0.3 |
| F360V | 4 | 1 µM | 0 |
| | | 5 µM | 0.3 |
| F360T | 3 | 1 µM | 2.6 |
| A167C | 3 | 1 µM | 0 |
| A167L | 3 | 1 µM | 0.2 |
| A167L + F360M | 12 | 25 µM | 2 |
| A167C + F360I | 19 | 25 µM | 2 |
| CyPPO13 | | | |
| Wild type | | 1 µM | 0.5 |
| A177C | 1 | 1 µM | 0 |
| F373C | 2 | 1 µM | 0.1 |
| F373I | 2 | 1 µM | 0.1 |
| F373M | 2 | 1 µM | 0 |
| A177L + F373I | 9 | 10 µM | 1.5 |
| A177L + F373L | 7 | 10 µM | 0 |

After treatment with tiafenacil solution (25 µM tiafenacil+ 0.05% (v/v) Silwet L-77) or saflufenacil solution (100 µM saflufenacil+0.05% (v/v) Silwet L-77) in the amount of 100 ml per 40×60 cm area (0.24 m$^2$) to transformants (T$_3$) in which genes encoding CyPPO10 variant (F360I, F360L, F360M, A167C+F360I, A167C+F360M, or V305M+ F360M) were introduced, injury level of the plants was judged at the 7$^{th}$ day.

The result of T$_3$ transformants introduced with CyPPO10 variant encoding genes was shown in FIG. 32.

In addition, the injury level (Injury index) by tiafenacil or saflufenacil treatment of CyPPO10 mutant gene-introduced *A. thaliana* transformants was shown in the following Table 15 as numerical index.

TABLE 15

T$_3$ Injury Index (injury level)

| | | Line No. | Tiafenacil | Average injury index | Saflufenacil | Average injury index |
|---|---|---|---|---|---|---|
| | Col-0 | | 25 µM | 5 | 100 µM | 5 |
| CyPPO10 | F360I | 7-2 | 25 µM | 1 | 100 µM | 1.1 |
| | | 10-2 | | | 100 µM | 0 |
| | F360M | 4-7 | 25 µM | 2 | | |
| | F360L | 3-2 | 25 µM | 1 | | |
| | A167C + F360I | 1-4 | 25 µM | 2 | | |
| | A167C + F360M | 4-5 | 25 µM | 2 | | |
| | V305M + F360M | 6-5 | 25 µM | 2 | | |

The Table 14 and 15 showed the average of injury levels of tested individuals (10 to 20 individuals) according to the criteria of the following Table 16.

TABLE 16

Definition of injury level

| Injury index | Symptom |
|---|---|
| 0 | No damage |
| 1 | Dried leaf end or less than 20% scorched |
| 2 | Over 20% and less than 30% of the plant was scorched |
| 2.5 | Over 30% and less than 50% of the plant was scorched |
| 3 | Over 50% and less than 70% of the plant was scorched |
| 4 | Over 70% of the plant was scorched |
| 5 | The whole plant was dried and died |

The tolerance level of A. thaliana transformants ($T_3$) introduced with CyPPO10 mutant genes (F360I or A167L+F360M) or CyPPO13 mutant genes (A177L+F373L or A177L+F373I) was confirmed at the 7th day after treating tiafenacil, saflufenacil, flumioxazin, or sulfentrazone (50 μM each). For comparison, A. thaliana wild type or A. thaliana PPO1 SLYM (AtPPO1 SLYM, S305L+Y426M) transformants ($T_3$) known for PPO-inhibiting herbicide tolerance was tested as the same condition.

In the tolerance experiment with various herbicides, 100 ml of 50 μM concentration of each herbicide was evenly sprayed per a 40×60 cm area (0.24 m²). The molecular weight (MW) of tiafenacil, saflufenacil, flumioxazin and sulfentrazone is 511.87, 500.85, 354.34 and 387.18, respectively. The converted treatment dosages correspond to 106.7 g ai/ha of tiafenacil, 104.4 g ai/ha of saflufenacil, 73.8 g ai/ha of flumioxazin and 80.7 g ai/ha of sulfentrazone.

The result was shown in FIGS. 33a and 33b.

In addition, the injury level (Injury index) of transformants was shown in FIG. 33 and Table 17 as numerical index.

TABLE 17

T3 Injury Index (injury level)

|  | Cy10 FI | AtPPO1 SLYM | Cy10 ALFM |
|---|---|---|---|
| Tiafenacil | 1 | 4 | 1 |
| Saflufenacil | 0 | 0-1 | 0-1 |
| Flumioxazin | 0-1 | 4-5 | 1 |
| Sulfentrazone | 0-1 | 0-1 | 1 |

In FIG. 33a and Table 17, Cy10 FI, AtPPO1 SLYM, Cy10 ALFM represented the transformants of CyPPO10 F360I, S305L+Y426M of AtPPO1 (control), and CyPPO10 A167L+F360M, respectively.

In FIG. 33b, Col-0, Cy13 ALFL and Cy13 ALFI represented the wild type, transformants of CyPPO13 A177L+F373L and CyPPO13 A177L+F373I, respectively.

As shown in FIG. 33a, transformants of mutant gene have equal or more tolerance than AtPPO1 SLYM. It was demonstrated that all of CyPPO10 FI and CyPPO10 ALFM conferred higher level of tolerance to various herbicides compared to the AtPPO1 SLYM.

As shown in Table 14 and FIG. 8, almost all of the transformants with CyPPO10 wild type, its variant genes, CyPPO13 wild type, or its variant genes grew after 1 μM tiafenacil treatment while wild type A. thaliana (Col-0) died.

In addition, as shown in Table 15 and 17, FIGS. 9 to 10, and FIGS. 32 to 33, CyPPO10 or CyPPO13 variant gene-introduced A. thaliana transformants exhibited no or weak level of damage after over 5 μM of tiafenacil treatment. The result showed that herbicide tolerance of A. thaliana was conferred and/or enhanced by introduction of CyPPO10, CyPPO13, or their mutant gene.

It was demonstrated that herbicide tolerance was maintained $T_2$ to $T_3$ generations, which indicates that herbicide tolerance was stably transferred even if generation progresses.

From this result, the CyPPO variants are expected to give various PPO-inhibition herbicide tolerances to other plants as well as A. thaliana.

7-5. Confirmation of Transgene Stability During Generation Passage

In this Example, whether introduced genes in A. thaliana were stably inherited during generations was confirmed.

$T_3$ lines 7-2, 10-2, and 10-5 transformant transformed with CyPPO10 F360I were further developed to $T_4$, $T_5$ generation, and thereby tiafenacil or saflufenacil tolerance and the expression of introduced genes in $T_4$ and $T_5$ generations of each line were confirmed.

Protein Extraction

Proteins were extracted from plants of each generation. After grinding seedling using liquid nitrogen, protein extraction buffer (0.05 M Tris-Cl pH7.5, 0.1 M NaCl, 0.01 M EDTA, 1% Triton X-100, 1 mM DTT) was added and the total protein was extracted. After the extracted protein was transferred to PVDF membrane following electrophoresis, western blotting was conducted using anti-HA antibody (Santacruz).

Confirmation of Herbicide Tolerance

One hundred milliliters of herbicide solution containing 15 μM of tiafenacil or 150 μM of saflufenacil were evenly sprayed in the 40×60 cm area (0.24 m²) to A. thaliana 4 weeks after transplanting. The herbicide injury level was observed at the 7th day after the treatment.

The result of herbicide tolerance was shown in FIG. 34 ($T_4$) and FIG. 35 ($T_5$), and the injury level (Injury index) of transformants by herbicides was shown in Table 18.

TABLE 18

$T_4$ and $T_5$ Injury Index (injury level)

|  | CyPPO10 F360I | |
|---|---|---|
|  | $T_4$ | $T_5$ |
| Tiafenacil | 0.5 | 0.5 |
| Saflufenacil | 0 | 1 |

While the negative control (Col-0; A. thaliana wild type) was susceptible to the herbicides treatment, $T_4$ and $T_5$ A. thaliana transformants of CyPPO10 F360I were tolerant.

In addition, the western blotting analysis for transgene expression was shown in FIG. 36. The CyPPO10 F360I protein was detected only in all $T_4$ and $T_5$ generations of transformants Therefore it was demonstrated that herbicide tolerance by introduction of CyPPO10 variants was stably inherited and maintained through $T_4$ and $T_5$ generations.

Example 8. Construction of Soybean Transformants Using CyPPO and its Variants and PPO-Inhibiting Herbicide Tolerance Test 8-1. A Recombinant Vector for Soybean Transformation and Construction of Soybean Transformants Using the Same A vector for soybean plant transformation to confer tiafenacil tolerance by expressing CyPPO10 A167L+F360M gene was constructed.

Specifically, the CyPPO10 A167L+F360M gene combined with the transit peptide of *A. thaliana* PPO1 gene was amplified by PCR using the vector used for *A. thaliana* transformation (refer to FIG. 6) as a template. The amplified product was cloned using pENTR Directional TOPO cloning kits (Invitrogen), and transformed to DH5 alpha competent cell (Invitrogen). Then, the cloned gene was moved to a vector, pB2GW7.0 binary vector (FIG. 37) for plant transformation, using Gateway LR Clonase II Enzyme Mix (Invitrogen) kit. After mixing pENTR/D-TOPO vector in which CyPPO10 A167L+F360M gene was cloned, TE buffer, and LR Clonase II enzyme mix, it was incubated at 25° C. for 1 hr. After Proteinase K solution (Invitrogen) was added to the reaction mixture, it was incubated for 10 minutes at 37° C., and transformed to DH5 alpha competent cell.

*Agrobacterium* EHA105 was electro-transformed with the binary vector constructed as above.

Kwangan soybean plants were used for the construction of soybean transformants

After removing seed coat from soybean seed, hypocotyl was cut and wounded 7-8 times by surgical scalpel (#11 blade). Approximately 50 pieces of explants were mixed with transformed *A. tumefaciens* EHA105 (Hood et al., New Agrobacterium helper plasmids for gene transfer to plants (EHA105). Trans Res. 1993 2:208-218), and the mixture was sonicated for 20 seconds and then incubated for 30 minutes for inoculation. It was placed on CCM (Co-cultivation media; 0.32 g/L Gamborg B5, 4.26 g/L MES, 30 g/L sucrose, 0.7% agar). Then, it was co-cultured in a growth chamber (25° C., 18 h light/6 h dark) for 5 days.

After that, it was washed for 10 minutes in liquid ½ SIM (shoot induction media; 3.2 g/L Gamborg B5, 1.67 mg/L BA, 3 mM MES, 0.8% (w/v) agar, 3% (w/v) sucrose, 250 mg/L cefotaxime, 50 mg/L vancomycin, 100 mg/L ticarcillin, pH 5.6) and was placed on SIM without antibiotics and cultured in the growth chamber (25° C., 18 h light/6 h dark) for 2 weeks.

The shoot-induced explants were transplanted on SIM-1 (SIM media supplemented with 10 mg/L DL-phosphinothricin, pH 5.6).

The browned shoots were transplanted on SEM (shoot elongation media; 4.4 g/L MS salt, 3 mM MES, 0.5 mg/L GA3, 50 mg/L Asparagine, 100 mg/L pyroglutamic acid, 0.1 mg/L IAA, 1 mg/L zeatin, 3% (w/v) sucrose, 0.8% (w/v) agar, 250 mg/L cefotaxime, 50 mg/L vancomycin, 100 mg/L ticarcillin, 5 mg/L DL-phosphinothricin, pH 5.6). The elongated shoots over height 4 cm were transferred on RIM (root induction medium; 4.4 g/L MS salt, 3 mM MES, 3% sucrose, 0.8% Agar, 50 mg/L cefotaxime, 50 mg/L vancomycin, 50 mg/L ticarcillin, 25 mg/L asparagine, 25 mg/L pyroglutamic acid, pH 5.6).

When the roots grew sufficiently, the plants were moved to bed soil (Bioplug No. 2, Farmhannong) mixed with vermiculite in 2:1 (v/v). After 10 days, leaves were painted with 100 mg/L DL-phosphinothricin.

8-2. Verification of Herbicide Tolerance of Transformed Soybeans

Five micromolar or 15 µM of tiafenacil was painted to the leaves of lines No. 2 of CyPPO10 A167L+F360M transformed soybean ($T_0$ generation) and non-transformed soybean (Kwangan; wild type soybean, control) 2-3 times with a brush. tiafenacil solution contains 0.05% (v/v) Silwet L-77 as a surfactant.

As shown in FIG. 38, Kwangan (non-transformed soybean) exhibited severe damage 7 days after 5 µM tiafenacil treatment, but CyPPO10 A167L+F360M transformed soybean showed no damage even after the treatment of 15 µM tiafenacil.

Meanwhile, tiafenacil or saflufenacil was treated to $T_1$ generation of CyPPO10 A167L+F360M transformant line No. 2 at the stage of V2-3. The 100 ml of 25 µM tiafenacil or 150 µM saflufenacil was evenly sprayed on the area of 40×60 cm (0.24 m$^2$), and the damage level was evaluated 5 days after spray.

In FIG. 40, Kwangan soybean was used as a control. Compared to control, CyPPO10 A167L+F360M (10ALFM) transformant soybean showed no damage even after the treatment of a relatively high concentration of tiafenacil or saflufenacil.

8-3. Confirmation of the Number of Inserted Genes in Transformed Soybeans

The genomic DNA was extracted in 250 mg of leaf tissues of CyPPO10 A167L+F360M transformed lines No. 2 or No. 23, to analyze the copy number of the transgene.

The genomic DNA was extracted using CTAB buffer method. After grinding leaf tissues using a pestle and a mortar in liquid nitrogen, 1.25 ml of DNA isolation buffer (2% (w/v) CTAB, 1.5 M NaCl, 25 mM EDTA, 0.2% (v/v) beta-mercaptoethanol, 100 mM Tris-Cl (pH 8.0)) was added and vortexed. After heating at 60° C. for 1 hour, 1 volume of chloroform:isoamyl alcohol (24:1) was added and mixed by inverting. After centrifugation at 7000×g for 10 minutes at 4° C., supernatant was transferred to a new tube, and 2.5 volume of ethanol was mixed. After centrifugation at 5000×g for 5 minutes at 4° C., supernatant was discarded and the pellet was dissolved with TE buffer (LPSS). After adding 20 µg/ml RNase A (Bioneer), it was incubated at 37° C. for 30 minutes. After adding 1 volume of phenol:chloroform (1:1), it was mixed and centrifuged at 10,000×g for 10 minutes at 4° C. Supernatant was transferred to a new tube, and then 1 volume chloroform:isoamyl alcohol (24:1) was added and mixed. After centrifugation at 10,000×g for 10 minutes at 4° C., supernatant was transferred to a new tube and 0.1 volume of NaOAc (pH 5.2) and 2 volume of ethanol were added and mixed. After centrifugation at 5,000×g for 5 minutes at 4° C., it was washed with 70% ethanol. After air dry, genomic DNA was dissolved with an appropriate amount of TE buffer.

The 10~40 µg of extracted DNA was digested overnight using EcoRI (Enzynomics).

Then, after 0.8% (w/v) Agarose gel electrophoresis (50 V), gel was treated as follows:

1) depurination: 0.25 N HCl, 15 min shaking
2) denaturation: 0.5 M NaOH, 1.5 M NaCl, 30 min shaking
3) neutralization: 0.5 M Tris(pH 7.5), 1.5 M NaCl, 20 min shaking Thereafter, DNA fragments were moved to nitrocellulose membrane using a capillary transfer method, cross linking was performed using UV Crosslinker (UVC-508; ULTRA LUM Inc.).

Hybridization was performed by the following method: The nitrocellulose membrane was dipped in DIG Easyhybridization solution (Roche), and incubated at 42° C. for 3 hrs. Then, the solution was discarded, substituted with a fresh DIG Easyhybridization solution with DIG-labelled probe, and incubated for 16-18 hours at 42° C.

The probe (DIG-labeled CyPPO8-M probe) was labelled by PCR reaction as follows:

Probe PCR

The DIG-labeled bar gene was amplified using DIG dUTP (Jena bioscience), and the primers used then were as follows:

```
Forward primer for bar probe:
                           (SEQ ID NO: 124)
5'- TTC CGT ACC GAG CCG CAG GA-3'

Reverse primer for bar probe:
                           (SEQ ID NO: 125)
5'- CGT TGG GCA GCC CGA TGA CA-3'
```

PCR: Using Solgent e-Taq Kit

Conditions: 95° C. for 5 min, 35 cycles of 94° C. for 30 sec, 60° C. for 30 sec, and 72° C. for 30 sec, and 72° C. for 2 min After hybridization, membrane was washed in low stringency washing buffer (2×SSC, 0.1% SDS) and high stringency washing buffer (0.5×SSC, 0.1% SDS). Southern blotting signal was detected as follows:

1) shaking for 30 minutes after adding blocking buffer (Roche) to the membrane
2) shaking for 30 minutes after adding DIG antibody (anti-digoxigenin-AP Fab fragments, Roche)
3) shaking for 15 minutes in washing buffer (Roche)
4) shaking for 3 minutes after adding detection buffer (Roche)
5) After applying CDP-Star (Roche) on the membrane, developing the blot on x-ray film.

For a negative control, the genomic DNA of non-transformed Kwangan soybean plants was used for southern blotting.

In FIG. 39, the number of bands shown on the film means the number of transgenes. Since one band was observed in CyPPO10 A167L+F360M transformant line No. 2 or No. 23 lines, it was determined that each transgenic plant had a single copy transgene.

Example 9: Activity Test of Mutated Genes Having Sequence Homology to PPO Variant Error-prone PCR was conducted under the following conditions using CyPPO plasmid (pACBB vector) as a template, thereby inducing random mutations in CyPPO:

|  |  |
| --- | --- |
| Template | 0.5 μl |
| 10X buffer | 5 μl |
| 10 mM MnCl$_2$ | 1.5 μl |
| dNTP | 5 μl |
| e-Taq(Solgent Inc.) | 1 μl |
| forward primer (100 μM) | 0.5 μl |
| reverse primer (100 μM) | 0.5 μl |
| DDW | 36 μl |
| total | 50 μl |

10× buffer: 100 mM Tris-Cl, pH8.3; 500 mM KCl, 70 mM MgCl$_2$, 0.1% (w/v) gelatin dNTP: 10 mM dATP, 10 mM dGTP, 100 mM dCTP, 100 mM dTTP 94° C. 3 min; (94° C. 30 sec, 57° C. 30 sec, 72° C. 1.5 min, 72° C. 5 min) 35 cycles Primer Sequences:

```
CyPPO10_BamHI F
                           (SEQ ID NO: 126)
ccccggatccATGATTGAAGTGGATGTGGCTA CyPPO10_XhoI R
                           (SEQ ID NO: 127)
cccctcgagTGATTGTCCACCAGCGAGGTAAG CyPPO13_BamHI F
                           (SEQ ID NO: 128)
ccccggatccATGAACCCTGCTACCCCTGAAC CyPPO13_XhoI R
                           (SEQ ID NO: 129)
cccctcgagCACCTGTGATAACAACTGCTGAG
```

The obtained error-prone PCR product was electrophoresed in agarose gel and then cleaned up from gel, and pACBB vector and PCR product were digested by BamHI and XhoI restriction enzymes. The digested vector and PCR product electrophoresed in agarose gel were cleaned up, and ligation was conducted. Ligation product was transformed into BT3 competent cell, and mutated CyPPO genes from growing BT3 colonies were sequenced. BT3 confirmed to have mutated CyPPO genes were spotted on LB plate comprising various concentrations (0 μM, 50 μM, 100 μM, and 200 μM) of tiafenacil or saflufenacil, thereby investigating the growth of *E. coli*, and testing the level of herbicide tolerance.

Among the mutated clones, a clone having the following mutations was used for this herbicide tolerance test:

CyPPO10m-6: comprising 9 amino acid mutations (E225G, G258S, Q266L, T336I, V356F, F360M, A364D, R406G, W419R); nucleic acid sequence—SEQ ID NO: 130, amino acid sequence—SEQ ID NO: 131 (98% sequence homology to the amino acid sequence of wild type CyPPO10)

BT3 cells transformed with the mutant genes of CyPPO10 were cultured in herbicide-contained medium, and cell growth inhibition was measured. In FIG. 41, 'AtPPO1 WY refers to wild type PPO1 of *A. thaliana*,' AtPPO1 SLYM' to mutant PPO1 (Y426M+S305L) of *A. thaliana*, 'CyPPO10 WT' to wild type CyPPO10, and 'CyPPO10m-6' to mutated CyPPO10 as described above, respectively.

As shown in FIG. 41, the cells transformed with the CyPPO10 mutants having the sequence homology of 98% or higher to that of the wild type CyPPO10 display cell viability similar to that of cells with wild type CyPPO10, even the case in the medium containing high concentration (up to 200 μM) of tiafenacil or saflufenacil. This result demonstrates that the CyPPO10 mutants having the sequence homology of 98% or higher can retain herbicide tolerance (viability in herbicide containing media) of the wild type.

The invention claimed is:

1. A polypeptide comprising:
an amino acid sequence, which is modified from SEQ ID NO: 4 by at least one modification selected from the followings:
(1) a substitution of V175 with C (Cys);
(2) a substitution of V318 with M (Met);
(3) a substitution of F337 with V (Val);
(4) a substitution of L340 with T (Thr); and
(5) a substitution of I353 with T (Thr);
and wherein the amino acid sequence is at least 90% identical with the full length SEQ ID NO: 4.

2. The polypeptide of claim 1, which is further modified by at least one modification selected from the followings:
a substitution of A177 with C (Cys) or L (Leu), and
a substitution of F373 with M (Met), I (Ile), L (Leu), or V (Val).

3. A polynucleotide encoding the polypeptide of claim 1.

4. A recombinant vector comprising the polynucleotide of claim 2.

5. A recombinant cell comprising the recombinant vector of claim 4.

6. A composition for conferring or enhancing herbicide tolerance of a plant or algae, comprising at least one selected from the group consisting of the polypeptide of claim 1; a polynucleotide encoding the polypeptide; a recombinant vector comprising the polynucleotide; and a recombinant cell comprising the recombinant vector.

7. The composition of claim 6, wherein the herbicide is an herbicide inhibiting protoporphyrinogen oxidase.

8. The composition of claim 7, wherein the herbicide is at least one selected from the group consisting of pyrimidinediones, diphenyl-ethers, phenylpyrazoles, N-phenylphthalimides, phenylesters, thiadiazoles, oxadiazoles, triazolinones, oxazolidinediones, pyraclonil, flufenpyr-ethyl and profluazol.

9. The composition of claim 8, wherein the herbicide is at least one selected from the group consisting of butafenacil, saflufenacil, benzfendizone, tiafenacil, fomesafen, oxyfluorfen, aclonifen, acifluorfen, bifenox, ethoxyfen, lactofen, chlomethoxyfen, chlorintrofen, fluoroglycofen-ethyl, halosafen, pyraflufen-ethyl, fluazolate, flumioxazin, cinidon-ethyl, flumiclorac-pentyl, fluthiacet, thidiazimin, oxadiargyl, oxadiazon, carfentrazone, sulfentrazone, azafenidin, pentoxazone, pyraclonil, flufenpyr-ethyl, profluazol, phenopylate, carbamate analogues of phenopylate, and agriculturally acceptable salt thereof.

10. A transformant of a plant or algae having herbicide tolerance, or a clone or progeny thereof, comprising the polypeptide of claim 1 or a polynucleotide encoding thereof.

11. The transformant, clone or progeny thereof of claim 10, wherein the transformant is plant cell, protoplast, callus, hypocotyl, seed, cotyledon, shoot, or whole plant.

12. A method of preparing a plant or algae having herbicide tolerance, the method comprising transforming algae, or plant cell, protoplast, callus, hypocotyl, seed, cotyledon, shoot, or whole plant, with the polypeptide of claim 1 or a polynucleotide encoding thereof, to prepare the plant or algae having herbicide tolerance.

13. A method of conferring or enhancing herbicide tolerance of a plant or algae, the method comprising transforming algae, or plant cell, protoplast, callus, hypocotyl, seed, cotyledon, shoot, or whole plant, with the polypeptide of claim 1 or a polynucleotide encoding thereof.

14. A method of controlling weeds in a cropland, the method comprising,
providing the cropland with a plant comprising the polypeptide of claim 1 or a polynucleotide encoding thereof, and
applying an effective dosage of protoporphyrinogen oxidase-inhibiting herbicide to the cropland.

15. The method of claim 14, wherein the step of applying an effective dosage of protoporphyrinogen oxidase-inhibiting herbicide to the cropland is performed by applying an effective dosage of two or more kinds of protoporphyrinogen oxidase-inhibiting herbicides sequentially or simultaneously.

16. The method of claim 14,
wherein the plant further comprises the second herbicide-tolerant polypeptide or a gene encoding thereof, and
the step of applying an effective dosage of protoporphyrinogen oxidase-inhibiting herbicide to the cropland is performed by applying an effective dosage of the protoporphyrinogen oxidase-inhibiting herbicide and a second herbicide are applied sequentially or simultaneously.

17. A method of removing an undesired aquatic organism from a culture medium, the method comprising,
providing a culture medium with algae comprising the polypeptide of claim 1 or a polynucleotide encoding thereof, and
applying an effective dosage of protoporphyrinogen oxidase-inhibiting herbicide to the culture medium.

18. The method of claim 13, wherein the plant or algae further comprise a second herbicide-tolerant polypeptide or a gene encoding thereof, and tolerance to the second herbicide is conferred or enhanced.

19. The method of claim 18, wherein the second herbicide is selected from the group consisting of glyphosate, glufosinate, dicamba, 2,4-D (2,4-dichlorophenoxyacetic acid), isoxaflutole, ALS (acetolactate synthase)-inhibiting herbicide, photosystem II-inhibiting herbicide, phenylurea-based herbicide, bromoxynil-based herbicide, and combinations thereof.

20. The method of claim 18, wherein the second herbicide-tolerant polypeptide is at least one selected from the group consisting of,
glyphosate herbicide-tolerant EPSPS (glyphosate tolerant 5-enolpyruvylshikimate-3-phosphate synthase), GOX (glyphosate oxidase), GAT (glyphosate-N-acetyltransferase) or glyphosate decarboxylase;
glufosinate herbicide-tolerant PAT (phosphinothricin-N-acetyltransferase);
dicamba herbicide-tolerant DMO (Dicamba monooxygenase);
2,4-D (2,4-dichlorophenoxyacetic acid) herbicide-tolerant 2,4-D monooxygenase or AAD (aryloxyalkanoate Dioxygenase);
ALS (acetolactate synthase)-inhibiting sulfonylurea-based herbicide-tolerant AHAS (acetohydroxyacid synthase), AHAS (acetohydroxyacid synthase) or Atahasl (acetohydroxyacid synthase large subunit);
photosystem II-inhibiting herbicide-tolerant photosystem II protein D1;
phenylurea herbicide-tolerant Cytochrome P450;
plastid-inhibiting herbicide-tolerant HPPD (Hydroxylphenylpyruvate dioxygenase);
bromoxynil herbicide-tolerant Nitrilase; and
combinations thereof.

21. The method of claim 18, wherein the gene encoding the second herbicide-tolerant polypeptide is at least one selected from the group consisting of,
glyphosate herbicide-tolerant cp4 epsps, epsps (AG), mepsps, 2mepsps, goxv247, gat4601 or gat4621 gene;
glufosinate herbicide-tolerant bar or pat gene;
dicamba herbicide-tolerant dmo gene;
2,4-D (2,4-Dichlorophenoxyacetic acid) herbicide-tolerant AAD-1 or AAD-12 gene;
isoxaflutole herbicide-tolerant HPPDPF W336 gene;
sulfonylurea herbicide-tolerant ALS, Csr1, Csr1-1, Csr1-2, GM-HRA, S4-HRA, Zm-HRA, SurA or SurB gene;
photosystem II-inhibiting herbicide-tolerant psbA gene;
phenylurea herbicide-tolerant CYP76B1 gene;
bromoxynil herbicide-tolerant bxn gene; and
combinations thereof.

* * * * *

SEQUENCE LISTING

<160> NUMBER OF SEQ ID NOS: 131

<210> SEQ ID NO 1
<211> LENGTH: 1404
<212> TYPE: DNA
<213> ORGANISM: Artificial Sequence
<220> FEATURE:
<223> OTHER INFORMATION: Synthetic: Polynucleotide encoding CyPPO10

<400> SEQUENCE: 1

```
atgattgaag tggatgtggc tattgttggt ggtggtctta gtggattgtc agtggcttgg        60
agattacaga ggagtgctcc tcattattct ggagttcttc ttgaggcttc tgatagactt       120
ggaggtaata tcactacaca agctgctgaa ggatttgtgt gggagcttgg tccaaacagt       180
ttcgctccta ctccagcact cttacagttg attgctgaag ttggactcca ttctgagtta       240
atcagaggag ataggcacct tccaagatat atatactgga ggggagaact ttatcctttg       300
gagccaacta ggcctcttgc tttggcaaca tcaaatcttt tgagtccttg gggaaaggtt       360
agagctgcac tcggagcttt aggttttgtg cctccatatc ttggatctgg agatgaaagt       420
gttgattctt tctttagaag gcatcttgga caagaagttg ctgagagatt ggtggcacca       480
tttgtttcag gagtgtacgc tggagatcct caacagcttt ctgctgctgc tgcttttaga       540
aggattgctc aacttgagaa gttgggaggt tcattgatcg ctggagcact cagattaaga       600
aggcaacagc ctccacagcc aaaacctcca gctcaagtgc agatgagacc tggagaactc       660
ggtagtttta gggagggtct cgctgcatta cctagagcta tcgcacaaca gttgaaggca       720
ccacttcatt tgcaaacacc tgttgaagct attaccccctg agccaaaagg aggttatctc       780
ttaaggagtg gtgaacagac ttggcacgct agatcagttg tgttggctac tccagcatac       840
caaactgctg aacttgttgc accattccag cctgctatcg ctagagcttt ggctaccata       900
ccttatccaa ctgttgcttg tgttgtgctt gcttaccctg ctggattggg tagatcagtt       960
agacctggat ttggtgtttt ggtgcctaga ggacaaggta taaggacact cggaaccatt      1020
tggtcttcat gcttattccc acaaagaact cctgctggtt ggcaggtttt tacctctttc      1080
ataggaggtg ctactgatcc tgatcttgca tcattgagag aagaggctat tgttgaacaa      1140
gtgcaacagg atctcacaag gcttcttgat cttcctgctg caaaggcaag actcttgggt      1200
atgaaggttt ggagaagggc tattccacaa tatatcgttg gttaccctca acagtggcaa      1260
caggtgacac acgctcttac ccagactcct ggtctcttct tatgttcaaa ctacgctgag      1320
ggagttgcat tgggagatag agtggaacac ggaaatagga ctgctgctgc tgtggctgct      1380
tacctcgctg gtggacaatc ataa                                              1404
```

<210> SEQ ID NO 2
<211> LENGTH: 467
<212> TYPE: PRT
<213> ORGANISM: Artificial Sequence
<220> FEATURE:
<223> OTHER INFORMATION: Synthetic: CyPPO10

<400> SEQUENCE: 2

```
Met Ile Glu Val Asp Val Ala Ile Val Gly Gly Gly Leu Ser Gly Leu
1               5                   10                  15

Ser Val Ala Trp Arg Leu Gln Arg Ser Ala Pro His Tyr Ser Gly Val
            20                  25                  30

Leu Leu Glu Ala Ser Asp Arg Leu Gly Gly Asn Ile Thr Thr Gln Ala
        35                  40                  45
```

```
Ala Glu Gly Phe Val Trp Glu Leu Gly Pro Asn Ser Phe Ala Pro Thr
 50                  55                  60

Pro Ala Leu Leu Gln Leu Ile Ala Glu Val Gly Leu His Ser Glu Leu
 65                  70                  75                  80

Ile Arg Gly Asp Arg His Leu Pro Arg Tyr Ile Tyr Trp Arg Gly Glu
                 85                  90                  95

Leu Tyr Pro Leu Glu Pro Thr Arg Pro Leu Ala Leu Ala Thr Ser Asn
                100                 105                 110

Leu Leu Ser Pro Trp Gly Lys Val Arg Ala Ala Leu Gly Ala Leu Gly
            115                 120                 125

Phe Val Pro Pro Tyr Leu Gly Ser Gly Asp Glu Ser Val Asp Ser Phe
130                 135                 140

Phe Arg Arg His Leu Gly Gln Glu Val Ala Glu Arg Leu Val Ala Pro
145                 150                 155                 160

Phe Val Ser Gly Val Tyr Ala Gly Asp Pro Gln Gln Leu Ser Ala Ala
                165                 170                 175

Ala Ala Phe Arg Arg Ile Ala Gln Leu Glu Lys Leu Gly Gly Ser Leu
                180                 185                 190

Ile Ala Gly Ala Leu Arg Leu Arg Arg Gln Gln Pro Pro Gln Pro Lys
            195                 200                 205

Pro Pro Ala Gln Val Gln Met Arg Pro Gly Glu Leu Gly Ser Phe Arg
210                 215                 220

Glu Gly Leu Ala Ala Leu Pro Arg Ala Ile Ala Gln Gln Leu Lys Ala
225                 230                 235                 240

Pro Leu His Leu Gln Thr Pro Val Glu Ala Ile Thr Pro Glu Pro Lys
                245                 250                 255

Gly Gly Tyr Leu Leu Arg Ser Gly Glu Gln Thr Trp His Ala Arg Ser
            260                 265                 270

Val Val Leu Ala Thr Pro Ala Tyr Gln Thr Ala Glu Leu Val Ala Pro
            275                 280                 285

Phe Gln Pro Ala Ile Ala Arg Ala Leu Ala Thr Ile Pro Tyr Pro Thr
290                 295                 300

Val Ala Cys Val Val Leu Ala Tyr Pro Ala Gly Leu Gly Arg Ser Val
305                 310                 315                 320

Arg Pro Gly Phe Gly Val Leu Val Pro Arg Gly Gln Gly Ile Arg Thr
                325                 330                 335

Leu Gly Thr Ile Trp Ser Ser Cys Leu Phe Pro Gln Arg Thr Pro Ala
            340                 345                 350

Gly Trp Gln Val Phe Thr Ser Phe Ile Gly Gly Ala Thr Asp Pro Asp
            355                 360                 365

Leu Ala Ser Leu Arg Glu Glu Ala Ile Val Glu Gln Val Gln Gln Asp
370                 375                 380

Leu Thr Arg Leu Leu Asp Leu Pro Ala Ala Lys Ala Arg Leu Leu Gly
385                 390                 395                 400

Met Lys Val Trp Arg Arg Ala Ile Pro Gln Tyr Ile Val Gly Tyr Pro
                405                 410                 415

Gln Gln Trp Gln Gln Val Thr His Ala Leu Thr Gln Thr Pro Gly Leu
            420                 425                 430

Phe Leu Cys Ser Asn Tyr Ala Glu Gly Val Ala Leu Gly Asp Arg Val
            435                 440                 445

Glu His Gly Asn Arg Thr Ala Ala Ala Val Ala Ala Tyr Leu Ala Gly
450                 455                 460

Gly Gln Ser
```

<210> SEQ ID NO 3
<211> LENGTH: 1458
<212> TYPE: DNA
<213> ORGANISM: Artificial Sequence
<220> FEATURE:
<223> OTHER INFORMATION: Synthetic: Polynucleotide encoding CyPPO13

<400> SEQUENCE: 3

```
atgaaccctg ctacccctga acctttgaat gctgaagttg ttgtgattgg tgctggaatt      60
tctggattga ccttggcttg gagactccaa cagggtctta gtgctagagg aggttctcca     120
caagcagttc ttttggctga agcatcttca agggtgggag ttgtattag tacccagtct     180
aaggatggat atagatggga gagggtcct aatagtttta ctccaacacc tgctctctta     240
aacctcattg cagaagttgg attaactgat caacttgtgt tggctgatgc aaagttgcca     300
agatatatct actgggaggg tgctcttttg ccagttcctc tttcacctgc tgctgctttg     360
ggatctaggc tcttatcagt tggaggtaaa cttagagctt gcaggggact tttgggtttt     420
gttcctccac ctccaggtca tgaagagact gtgagacaat ttttcagaag cagcttgga     480
tctgaagttg ctgagagatt ggtggagcct ttcacatcag gagtttatgc tggagatcct     540
gatcaactta gtgcagttgc agcttttcct agggtggctg gtctcgaaga gagatacgga     600
tcattattcg ctggtgctct tcaagctctt aggcaaagac acagcctag tccagcagct     660
atccagcctc cacctaaaag gggacaactt ggtaatttga cagggact ccaacagtta     720
cctgaagctc ttgcacaaaa gttgggagat tctctcagat taggttggag agcttttgcaa     780
ttgaaaagag caggagagct ttattgggtt ggtttcgaaa ctccagaggg atcaaggtgg     840
gttgctgcta caagttgt gctcgctta cctgcatacg aagcagctgc actcttacaa     900
gagttgaacc cacctgcttc tcagcttttg gcagaaatac tctatccacc tgttgctgtt     960
gtggctcttg catacccaca agaggctctc cctcagccat taagaggatt tggtcatctc    1020
atccctaggt ctcaaggact tagaaccttg gtactatat gggcttcatg tttgttccct    1080
gaaagagcac ctcaaggtta tcactcattt ctcagtttct taggaggtgc tacagatgct    1140
gcattggcaa gaaggagagg tattcctcct atccctgctc tcagtccaga agagagagca    1200
caaatagctc acgcagagct ttctcaggtt ctcttaacca ggagagctga accagtgtat    1260
cttggagaga ggttgtggcc tagagctata ccacaataca cacttggaca taggcagaga    1320
attgctcaag ttcaggctca cttggcatct caaaccctg gtatttgggt ttgcgctaat    1380
tacttggatg gagtggcact cggagattgc gttagaaggg cagaggcact cgctcagcag    1440
ttgttatcac aggtgtaa                                                  1458
```

<210> SEQ ID NO 4
<211> LENGTH: 485
<212> TYPE: PRT
<213> ORGANISM: Artificial Sequence
<220> FEATURE:
<223> OTHER INFORMATION: Synthetic: CyPPO13

<400> SEQUENCE: 4

Met Asn Pro Ala Thr Pro Glu Pro Leu Asn Ala Glu Val Val Val Ile
1               5                   10                  15

Gly Ala Gly Ile Ser Gly Leu Thr Leu Ala Trp Arg Leu Gln Gln Gly
            20                  25                  30

Leu Ser Ala Arg Gly Gly Ser Pro Gln Ala Val Leu Leu Ala Glu Ala

```
                35                  40                  45
Ser Ser Arg Val Gly Gly Cys Ile Ser Thr Gln Ser Lys Asp Gly Tyr
 50                  55                  60

Arg Trp Glu Glu Gly Pro Asn Ser Phe Thr Pro Thr Pro Ala Leu Leu
 65                  70                  75                  80

Asn Leu Ile Ala Glu Val Gly Leu Thr Asp Gln Leu Val Leu Ala Asp
                 85                  90                  95

Ala Lys Leu Pro Arg Tyr Ile Tyr Trp Glu Gly Ala Leu Leu Pro Val
                100                 105                 110

Pro Leu Ser Pro Ala Ala Leu Gly Ser Arg Leu Leu Ser Val Gly
            115                 120                 125

Gly Lys Leu Arg Ala Leu Gln Gly Leu Leu Gly Phe Val Pro Pro Pro
130                 135                 140

Pro Gly His Glu Glu Thr Val Arg Gln Phe Phe Arg Arg Gln Leu Gly
145                 150                 155                 160

Ser Glu Val Ala Glu Arg Leu Val Glu Pro Phe Thr Ser Gly Val Tyr
                165                 170                 175

Ala Gly Asp Pro Asp Gln Leu Ser Ala Val Ala Ala Phe Pro Arg Val
                180                 185                 190

Ala Gly Leu Glu Glu Arg Tyr Gly Ser Leu Phe Ala Gly Ala Leu Gln
            195                 200                 205

Ala Leu Arg Gln Arg Pro Gln Pro Ser Pro Ala Ala Ile Gln Pro Pro
210                 215                 220

Pro Lys Arg Gly Gln Leu Gly Asn Leu Arg Gln Gly Leu Gln Gln Leu
225                 230                 235                 240

Pro Glu Ala Leu Ala Gln Lys Leu Gly Asp Ser Leu Arg Leu Gly Trp
                245                 250                 255

Arg Ala Leu Gln Leu Lys Arg Ala Gly Glu Leu Tyr Trp Val Gly Phe
                260                 265                 270

Glu Thr Pro Glu Gly Ser Arg Trp Val Ala Ala Arg Gln Val Val Leu
            275                 280                 285

Ala Leu Pro Ala Tyr Glu Ala Ala Leu Leu Gln Glu Leu Asn Pro
290                 295                 300

Pro Ala Ser Gln Leu Leu Ala Glu Ile Leu Tyr Pro Pro Val Ala Val
305                 310                 315                 320

Val Ala Leu Ala Tyr Pro Gln Glu Ala Leu Pro Gln Pro Leu Arg Gly
                325                 330                 335

Phe Gly His Leu Ile Pro Arg Ser Gln Gly Leu Arg Thr Leu Gly Thr
                340                 345                 350

Ile Trp Ala Ser Cys Leu Phe Pro Glu Arg Ala Pro Gln Gly Tyr His
            355                 360                 365

Ser Phe Leu Ser Phe Leu Gly Ala Thr Asp Ala Ala Leu Ala Arg
            370                 375                 380

Arg Arg Gly Ile Pro Pro Ile Pro Ala Leu Ser Pro Glu Glu Arg Ala
385                 390                 395                 400

Gln Ile Ala His Ala Glu Leu Ser Gln Val Leu Leu Thr Arg Arg Ala
                405                 410                 415

Glu Pro Val Tyr Leu Gly Glu Arg Leu Trp Pro Arg Ala Ile Pro Gln
                420                 425                 430

Tyr Thr Leu Gly His Arg Gln Arg Ile Ala Gln Val Gln Ala His Leu
            435                 440                 445

Ala Ser Gln Thr Pro Gly Ile Trp Val Cys Ala Asn Tyr Leu Asp Gly
450                 455                 460
```

```
Val Ala Leu Gly Asp Cys Val Arg Arg Ala Glu Ala Leu Ala Gln Gln
465                 470                 475                 480

Leu Leu Ser Gln Val
            485

<210> SEQ ID NO 5
<211> LENGTH: 537
<212> TYPE: PRT
<213> ORGANISM: Arabidopsis thaliana
<220> FEATURE:
<221> NAME/KEY: PEPTIDE
<222> LOCATION: (1)..(537)
<223> OTHER INFORMATION: Wild type AtPPO1

<400> SEQUENCE: 5

Met Glu Leu Ser Leu Leu Arg Pro Thr Thr Gln Ser Leu Leu Pro Ser
1               5                   10                  15

Phe Ser Lys Pro Asn Leu Arg Leu Asn Val Tyr Lys Pro Leu Arg Leu
            20                  25                  30

Arg Cys Ser Val Ala Gly Gly Pro Thr Val Gly Ser Ser Lys Ile Glu
        35                  40                  45

Gly Gly Gly Gly Thr Thr Ile Thr Thr Asp Cys Val Ile Val Gly Gly
50                  55                  60

Gly Ile Ser Gly Leu Cys Ile Ala Gln Ala Leu Ala Thr Lys His Pro
65                  70                  75                  80

Asp Ala Ala Pro Asn Leu Ile Val Thr Glu Ala Lys Asp Arg Val Gly
                85                  90                  95

Gly Asn Ile Ile Thr Arg Glu Glu Asn Gly Phe Leu Trp Glu Glu Gly
            100                 105                 110

Pro Asn Ser Phe Gln Pro Ser Asp Pro Met Leu Thr Met Val Val Asp
        115                 120                 125

Ser Gly Leu Lys Asp Asp Leu Val Leu Gly Asp Pro Thr Ala Pro Arg
130                 135                 140

Phe Val Leu Trp Asn Gly Lys Leu Arg Pro Val Pro Ser Lys Leu Thr
145                 150                 155                 160

Asp Leu Pro Phe Phe Asp Leu Met Ser Ile Gly Gly Lys Ile Arg Ala
                165                 170                 175

Gly Phe Gly Ala Leu Gly Ile Arg Pro Ser Pro Pro Gly Arg Glu Glu
            180                 185                 190

Ser Val Glu Glu Phe Val Arg Arg Asn Leu Gly Asp Glu Val Phe Glu
        195                 200                 205

Arg Leu Ile Glu Pro Phe Cys Ser Gly Val Tyr Ala Gly Asp Pro Ser
210                 215                 220

Lys Leu Ser Met Lys Ala Ala Phe Gly Lys Val Trp Lys Leu Glu Gln
225                 230                 235                 240

Asn Gly Gly Ser Ile Ile Gly Gly Thr Phe Lys Ala Ile Gln Glu Arg
                245                 250                 255

Lys Asn Ala Pro Lys Ala Glu Arg Asp Pro Arg Leu Pro Lys Pro Gln
            260                 265                 270

Gly Gln Thr Val Gly Ser Phe Arg Lys Gly Leu Arg Met Leu Pro Glu
        275                 280                 285

Ala Ile Ser Ala Arg Leu Gly Ser Lys Val Lys Leu Ser Trp Lys Leu
290                 295                 300

Ser Gly Ile Thr Lys Leu Glu Ser Gly Gly Tyr Asn Leu Thr Tyr Glu
305                 310                 315                 320
```

```
Thr Pro Asp Gly Leu Val Ser Val Gln Ser Lys Ser Val Val Met Thr
                325                 330                 335

Val Pro Ser His Val Ala Ser Gly Leu Leu Arg Pro Leu Ser Glu Ser
            340                 345                 350

Ala Ala Asn Ala Leu Ser Lys Leu Tyr Tyr Pro Pro Val Ala Ala Val
        355                 360                 365

Ser Ile Ser Tyr Pro Lys Glu Ala Ile Arg Thr Glu Cys Leu Ile Asp
    370                 375                 380

Gly Glu Leu Lys Gly Phe Gly Gln Leu His Pro Arg Thr Gln Gly Val
385                 390                 395                 400

Glu Thr Leu Gly Thr Ile Tyr Ser Ser Ser Leu Phe Pro Asn Arg Ala
                405                 410                 415

Pro Pro Gly Arg Ile Leu Leu Asn Tyr Ile Gly Gly Ser Thr Asn
            420                 425                 430

Thr Gly Ile Leu Ser Lys Ser Glu Gly Glu Leu Val Glu Ala Val Asp
        435                 440                 445

Arg Asp Leu Arg Lys Met Leu Ile Lys Pro Asn Ser Thr Asp Pro Leu
    450                 455                 460

Lys Leu Gly Val Arg Val Trp Pro Gln Ala Ile Pro Gln Phe Leu Val
465                 470                 475                 480

Gly His Phe Asp Ile Leu Asp Thr Ala Lys Ser Ser Leu Thr Ser Ser
                485                 490                 495

Gly Tyr Glu Gly Leu Phe Leu Gly Gly Asn Tyr Val Ala Gly Val Ala
            500                 505                 510

Leu Gly Arg Cys Val Glu Gly Ala Tyr Glu Thr Ala Ile Glu Val Asn
        515                 520                 525

Asn Phe Met Ser Arg Tyr Ala Tyr Lys
    530                 535

<210> SEQ ID NO 6
<211> LENGTH: 1614
<212> TYPE: DNA
<213> ORGANISM: Arabidopsis thaliana
<220> FEATURE:
<221> NAME/KEY: gene
<222> LOCATION: (1)..(1614)
<223> OTHER INFORMATION: Synthetic: Wild type AtPPO1

<400> SEQUENCE: 6
atggagttat ctcttctccg tccgacgact caatcgcttc ttccgtcgtt ttcgaagccc      60
aatctccgat taaatgttta taagcctctt agactccgtt gttcagtggc cggtggacca     120
accgtcggat cttcaaaaat cgaaggcgga ggaggcacca ccatcacgac ggattgtgtg     180
attgtcggcg gaggtattag tggtctttgc atcgctcagg cgcttgctac taagcatcct     240
gatgctgctc cgaatttaat tgtgaccgag gctaaggatc gtgttggagg caacattatc     300
actcgtgaag agaatggttt tctctgggaa gaaggtccca atagttttca accgtctgat     360
cctatgctca ctatggtggt agatagtggt ttgaaggatg atttggtgtt gggagatcct     420
actgcgccaa ggtttgtgtt gtggaatggg aaattgaggc cggttccatc gaagctaaca     480
gacttaccgt tctttgattt gatgagtatt ggtgggaaga ttagagctgg ttttggtgca     540
cttggcattc gaccgtcacc tccaggtcgt gaagaatctg tggaggagtt tgtacggcgt     600
aacctcggtg atgaggtttt tgagcgcctg attgaaccgt tttgttcagg tgtttatgct     660
ggtgatcctc caaaactgag catgaaagca gcgtttggga aggtttggaa actagagcaa     720
aatggtggaa gcataatagg tggtactttt aaggcaattc aggagaggaa aaacgctccc     780
```

```
aaggcagaac gagacccgcg cctgccaaaa ccacagggcc aaacagttgg ttctttcagg    840
aagggacttc gaatgttgcc agaagcaata tctgcaagat taggtagcaa agttaagttg    900
tcttggaagc tctcaggtat cactaagctg gagagcggag gatacaactt aacatatgag    960
actccagatg gtttagtttc cgtgcagagc aaaagtgttg taatgacggt gccatctcat   1020
gttgcaagtg gtctcttgcg ccctcttcct gaatctgctg caaatgcact ctcaaaacta   1080
tattacccac cagttgcagc agtatctatc tcgtacccga aagaagcaat ccgaacagaa   1140
tgtttgatag atggtgaact aaagggtttt gggcaattgc atccacgcac gcaaggagtt   1200
gaaacattag gaactatcta cagctcctca ctctttccaa atcgcgcacc gcccggaaga   1260
attttgctgt tgaactacat tggcgggtct acaaacaccg gaattctgtc caagtctgaa   1320
ggtgagttag tggaagcagt tgacagagat ttgaggaaaa tgctaattaa gcctaattcg   1380
accgatccac ttaaattagg agttagggta tggcctcaag ccattcctca gtttctagtt   1440
ggtcactttg atatccttga cacggctaaa tcatctctaa cgtcttcggg ctacgaaggg   1500
ctattttggg gtggcaatta cgtcgctggt gtagccttag gccggtgtgt agaaggcgca   1560
tatgaaaccg cgattgaggt caacaacttc atgtcacggt acgcttacaa gtaa         1614
```

<210> SEQ ID NO 7
<211> LENGTH: 537
<212> TYPE: PRT
<213> ORGANISM: Artificial Sequence
<220> FEATURE:
<223> OTHER INFORMATION: Synthetic: Mutant type AtPPO1

<400> SEQUENCE: 7

```
Met Glu Leu Ser Leu Leu Arg Pro Thr Thr Gln Ser Leu Leu Pro Ser
1               5                   10                  15

Phe Ser Lys Pro Asn Leu Arg Leu Asn Val Tyr Lys Pro Leu Arg Leu
            20                  25                  30

Arg Cys Ser Val Ala Gly Gly Pro Thr Val Gly Ser Ser Lys Ile Glu
        35                  40                  45

Gly Gly Gly Gly Thr Thr Ile Thr Thr Asp Cys Val Ile Val Gly Gly
    50                  55                  60

Gly Ile Ser Gly Leu Cys Ile Ala Gln Ala Leu Ala Thr Lys His Pro
65                  70                  75                  80

Asp Ala Ala Pro Asn Leu Ile Val Thr Glu Ala Lys Asp Arg Val Gly
                85                  90                  95

Gly Asn Ile Ile Thr Arg Glu Glu Asn Gly Phe Leu Trp Glu Glu Gly
            100                 105                 110

Pro Asn Ser Phe Gln Pro Ser Asp Pro Met Leu Thr Met Val Val Asp
        115                 120                 125

Ser Gly Leu Lys Asp Asp Leu Val Leu Gly Asp Pro Thr Ala Pro Arg
    130                 135                 140

Phe Val Leu Trp Asn Gly Lys Leu Arg Pro Val Pro Ser Lys Leu Thr
145                 150                 155                 160

Asp Leu Pro Phe Phe Asp Leu Met Ser Ile Gly Gly Lys Ile Arg Ala
                165                 170                 175

Gly Phe Gly Ala Leu Gly Ile Arg Pro Ser Pro Gly Arg Glu Glu
            180                 185                 190

Ser Val Glu Glu Phe Val Arg Arg Asn Leu Gly Asp Glu Val Phe Glu
        195                 200                 205

Arg Leu Ile Glu Pro Phe Cys Ser Gly Val Tyr Ala Gly Asp Pro Ser
```

```
            210                 215                 220
Lys Leu Ser Met Lys Ala Ala Phe Gly Lys Val Trp Lys Leu Glu Gln
225                 230                 235                 240

Asn Gly Gly Ser Ile Ile Gly Gly Thr Phe Lys Ala Ile Gln Glu Arg
                245                 250                 255

Lys Asn Ala Pro Lys Ala Glu Arg Asp Pro Arg Leu Pro Lys Pro Gln
                260                 265                 270

Gly Gln Thr Val Gly Ser Phe Arg Lys Gly Leu Arg Met Leu Pro Glu
            275                 280                 285

Ala Ile Ser Ala Arg Leu Gly Ser Lys Val Lys Leu Ser Trp Lys Leu
        290                 295                 300

Leu Gly Ile Thr Lys Leu Glu Ser Gly Gly Tyr Asn Leu Thr Tyr Glu
305                 310                 315                 320

Thr Pro Asp Gly Leu Val Ser Val Gln Ser Lys Ser Val Val Met Thr
                325                 330                 335

Val Pro Ser His Val Ala Ser Gly Leu Leu Arg Pro Leu Ser Glu Ser
                340                 345                 350

Ala Ala Asn Ala Leu Ser Lys Leu Tyr Tyr Pro Pro Val Ala Ala Val
            355                 360                 365

Ser Ile Ser Tyr Pro Lys Glu Ala Ile Arg Thr Glu Cys Leu Ile Asp
        370                 375                 380

Gly Glu Leu Lys Gly Phe Gly Gln Leu His Pro Arg Thr Gln Gly Val
385                 390                 395                 400

Glu Thr Leu Gly Thr Ile Tyr Ser Ser Ser Leu Phe Pro Asn Arg Ala
                405                 410                 415

Pro Pro Gly Arg Ile Leu Leu Asn Met Ile Gly Gly Ser Thr Asn
            420                 425                 430

Thr Gly Ile Leu Ser Lys Ser Glu Gly Glu Leu Val Glu Ala Val Asp
        435                 440                 445

Arg Asp Leu Arg Lys Met Leu Ile Lys Pro Asn Ser Thr Asp Pro Leu
450                 455                 460

Lys Leu Gly Val Arg Val Trp Pro Gln Ala Ile Pro Gln Phe Leu Val
465                 470                 475                 480

Gly His Phe Asp Ile Leu Asp Thr Ala Lys Ser Ser Leu Thr Ser Ser
                485                 490                 495

Gly Tyr Glu Gly Leu Phe Leu Gly Gly Asn Tyr Val Ala Gly Val Ala
            500                 505                 510

Leu Gly Arg Cys Val Glu Gly Ala Tyr Glu Thr Ala Ile Glu Val Asn
        515                 520                 525

Asn Phe Met Ser Arg Tyr Ala Tyr Lys
530                 535

<210> SEQ ID NO 8
<211> LENGTH: 30
<212> TYPE: DNA
<213> ORGANISM: Artificial Sequence
<220> FEATURE:
<223> OTHER INFORMATION: Synthetic: CyPPO10co_BamHI F primer

<400> SEQUENCE: 8
ccccggatcc atgattgaag tggatgtggc                                    30

<210> SEQ ID NO 9
<211> LENGTH: 30
<212> TYPE: DNA
<213> ORGANISM: Artificial Sequence
```

```
<220> FEATURE:
<223> OTHER INFORMATION: Synthetic: CyPPO10co_XhoI R primer

<400> SEQUENCE: 9 cccccctcgag tgattgtcca ccagcgaggt                                30

<210> SEQ ID NO 10
<211> LENGTH: 30
<212> TYPE: DNA
<213> ORGANISM: Artificial Sequence
<220> FEATURE:
<223> OTHER INFORMATION: Synthetic: CyPPO13co_BamHI F primer

<400> SEQUENCE: 10
ccccggatcc atgaaccctg ctaccccctga                                30

<210> SEQ ID NO 11
<211> LENGTH: 30
<212> TYPE: DNA
<213> ORGANISM: Artificial Sequence
<220> FEATURE:
<223> OTHER INFORMATION: Synthetic: CyPPO13co_XhoI R primer

<400> SEQUENCE: 11 cccccctcgag cacctgtgat aacaactgct                                30

<210> SEQ ID NO 12
<211> LENGTH: 30
<212> TYPE: DNA
<213> ORGANISM: Artificial Sequence
<220> FEATURE:
<223> OTHER INFORMATION: Synthetic: CyPPO10co_XbaI F primer

<400> SEQUENCE: 12
cccctctaga atgattgaag tggatgtggc                                 30

<210> SEQ ID NO 13
<211> LENGTH: 30
<212> TYPE: DNA
<213> ORGANISM: Artificial Sequence
<220> FEATURE:
<223> OTHER INFORMATION: Synthetic: CyPPO10co_XhoI R primer

<400> SEQUENCE: 13 cccccctcgag tgattgtcca ccagcgaggt                                30

<210> SEQ ID NO 14
<211> LENGTH: 29
<212> TYPE: DNA
<213> ORGANISM: Artificial Sequence
<220> FEATURE:
<223> OTHER INFORMATION: Synthetic: CyPPO13co_XbaI F primer

<400> SEQUENCE: 14
ccctctagaa tgaaccctgc taccccctga                                 29

<210> SEQ ID NO 15
<211> LENGTH: 30
<212> TYPE: DNA
<213> ORGANISM: Artificial Sequence
<220> FEATURE:
<223> OTHER INFORMATION: Synthetic: CyPPO13co_XhoI R primer

<400> SEQUENCE: 15 cccccctcgag cacctgtgat aacaactgct                                30
```

<210> SEQ ID NO 16
<211> LENGTH: 30
<212> TYPE: DNA
<213> ORGANISM: Artificial Sequence
<220> FEATURE:
<223> OTHER INFORMATION: Synthetic: F primer for CyPPO10_F360M

<400> SEQUENCE: 16
gtttttacct ctatgatagg aggtgctact                                    30

<210> SEQ ID NO 17
<211> LENGTH: 30
<212> TYPE: DNA
<213> ORGANISM: Artificial Sequence
<220> FEATURE:
<223> OTHER INFORMATION: Synthetic: R primer for CyPPO10_F360M

<400> SEQUENCE: 17
agcacctcct atcatagagg taaaaacctg                                    30

<210> SEQ ID NO 18
<211> LENGTH: 30
<212> TYPE: DNA
<213> ORGANISM: Artificial Sequence
<220> FEATURE:
<223> OTHER INFORMATION: Synthetic: F primer for CyPPO10_F360V

<400> SEQUENCE: 18
gtttttacct ctgttatagg aggtgctact                                    30

<210> SEQ ID NO 19
<211> LENGTH: 30
<212> TYPE: DNA
<213> ORGANISM: Artificial Sequence
<220> FEATURE:
<223> OTHER INFORMATION: Synthetic: R primer for CyPPO10_F360V

<400> SEQUENCE: 19
agcacctcct ataacagagg taaaaacctg                                    30

<210> SEQ ID NO 20
<211> LENGTH: 30
<212> TYPE: DNA
<213> ORGANISM: Artificial Sequence
<220> FEATURE:
<223> OTHER INFORMATION: Synthetic: F primer for CyPPO10_F360I

<400> SEQUENCE: 20
gtttttacct ctattatagg aggtgctact                                    30

<210> SEQ ID NO 21
<211> LENGTH: 30
<212> TYPE: DNA
<213> ORGANISM: Artificial Sequence
<220> FEATURE:
<223> OTHER INFORMATION: Synthetic: R primer for CyPPO10_F360I

<400> SEQUENCE: 21
agcacctcct ataatagagg taaaaacctg                                    30

<210> SEQ ID NO 22
<211> LENGTH: 30
<212> TYPE: DNA
<213> ORGANISM: Artificial Sequence
<220> FEATURE:
<223> OTHER INFORMATION: Synthetic: F primer for CyPPO10_F360T -continued

```
<400> SEQUENCE: 22 gttttttacct ctactatagg aggtgctact                                    30

<210> SEQ ID NO 23
<211> LENGTH: 30
<212> TYPE: DNA
<213> ORGANISM: Artificial Sequence
<220> FEATURE:
<223> OTHER INFORMATION: Synthetic: R primer for CyPPO10_F360T

<400> SEQUENCE: 23
agctccacca atagtagagg taaaaacctg                                     30

<210> SEQ ID NO 24
<211> LENGTH: 30
<212> TYPE: DNA
<213> ORGANISM: Artificial Sequence
<220> FEATURE:
<223> OTHER INFORMATION: Synthetic: F primer for CyPPO10_F360L

<400> SEQUENCE: 24 gttttttacct ctcttatagg aggtgctact                                    30

<210> SEQ ID NO 25
<211> LENGTH: 30
<212> TYPE: DNA
<213> ORGANISM: Artificial Sequence
<220> FEATURE:
<223> OTHER INFORMATION: Synthetic: R primer for CyPPO10_F360L

<400> SEQUENCE: 25
agctccacca ataagagagg taaaaacctg                                     30

<210> SEQ ID NO 26
<211> LENGTH: 30
<212> TYPE: DNA
<213> ORGANISM: Artificial Sequence
<220> FEATURE:
<223> OTHER INFORMATION: Synthetic: F primer for CyPPO10_F360C

<400> SEQUENCE: 26 gttttttacct cttgtatagg aggtgctact                                    30

<210> SEQ ID NO 27
<211> LENGTH: 30
<212> TYPE: DNA
<213> ORGANISM: Artificial Sequence
<220> FEATURE:
<223> OTHER INFORMATION: Synthetic: R primer for CyPPO10_F360C

<400> SEQUENCE: 27
agctccacca atacaagagg taaaaacctg                                     30

<210> SEQ ID NO 28
<211> LENGTH: 30
<212> TYPE: DNA
<213> ORGANISM: Artificial Sequence
<220> FEATURE:
<223> OTHER INFORMATION: Synthetic: F primer for CyPPO10_A167C

<400> SEQUENCE: 28
tcaggagtgt actgtggaga tcctcaacag                                     30

<210> SEQ ID NO 29
```

```
<211> LENGTH: 30
<212> TYPE: DNA
<213> ORGANISM: Artificial Sequence
<220> FEATURE:
<223> OTHER INFORMATION: Synthetic: R primer for CyPPO10_A167C

<400> SEQUENCE: 29
ttgaggatct ccacagtaca ctcctgaaac                                    30

<210> SEQ ID NO 30
<211> LENGTH: 30
<212> TYPE: DNA
<213> ORGANISM: Artificial Sequence
<220> FEATURE:
<223> OTHER INFORMATION: Synthetic: F primer for CyPPO10_A167L

<400> SEQUENCE: 30
tcaggagtgt accttggaga tcctcaacag                                    30

<210> SEQ ID NO 31
<211> LENGTH: 30
<212> TYPE: DNA
<213> ORGANISM: Artificial Sequence
<220> FEATURE:
<223> OTHER INFORMATION: Synthetic: R primer for CyPPO10_A167L

<400> SEQUENCE: 31
ttgaggatct ccaaggtaca ctcctgaaac                                    30

<210> SEQ ID NO 32
<211> LENGTH: 30
<212> TYPE: DNA
<213> ORGANISM: Artificial Sequence
<220> FEATURE:
<223> OTHER INFORMATION: Synthetic: F primer for CyPPO10_P303L+V305L

<400> SEQUENCE: 32
ataccttatc ttactcttgc ttgtgttgtg                                    30

<210> SEQ ID NO 33
<211> LENGTH: 27
<212> TYPE: DNA
<213> ORGANISM: Artificial Sequence
<220> FEATURE:
<223> OTHER INFORMATION: Synthetic: R primer for CyPPO10_P303L+V305L

<400> SEQUENCE: 33
aacacaagca agagtaagat aaggtat                                       27

<210> SEQ ID NO 34
<211> LENGTH: 30
<212> TYPE: DNA
<213> ORGANISM: Artificial Sequence
<220> FEATURE:
<223> OTHER INFORMATION: Synthetic: F primer for CyPPO10_V305M

<400> SEQUENCE: 34
ccttatccaa ctatggcttg tgttgtgctt                                    30

<210> SEQ ID NO 35
<211> LENGTH: 30
<212> TYPE: DNA
<213> ORGANISM: Artificial Sequence
<220> FEATURE:
<223> OTHER INFORMATION: Synthetic: R primer for CyPPO10_V305M

<400> SEQUENCE: 35
```

```
cacaacacaa gccatagttg gataaggtat                                    30

<210> SEQ ID NO 36
<211> LENGTH: 25
<212> TYPE: DNA
<213> ORGANISM: Artificial Sequence
<220> FEATURE:
<223> OTHER INFORMATION: Synthetic: F primer for CyPPO10_N59T

<400> SEQUENCE: 36
gagcttggtc caactagttt cgctc                                         25

<210> SEQ ID NO 37
<211> LENGTH: 27
<212> TYPE: DNA
<213> ORGANISM: Artificial Sequence
<220> FEATURE:
<223> OTHER INFORMATION: Synthetic: R primer for CyPPO10_N59T

<400> SEQUENCE: 37
agcgaaacta gttggaccaa gctccca                                       27

<210> SEQ ID NO 38
<211> LENGTH: 30
<212> TYPE: DNA
<213> ORGANISM: Artificial Sequence
<220> FEATURE:
<223> OTHER INFORMATION: Synthetic: F primer for CyPPO10_R89A

<400> SEQUENCE: 38
caccttccag cttatatata ctggagggga                                    30

<210> SEQ ID NO 39
<211> LENGTH: 30
<212> TYPE: DNA
<213> ORGANISM: Artificial Sequence
<220> FEATURE:
<223> OTHER INFORMATION: Synthetic: R primer for CyPPO10_R89A

<400> SEQUENCE: 39
gtatatataa gctggaaggt gcctatctcc                                    30

<210> SEQ ID NO 40
<211> LENGTH: 33
<212> TYPE: DNA
<213> ORGANISM: Artificial Sequence
<220> FEATURE:
<223> OTHER INFORMATION: Synthetic: F primer for CyPPO10_V165S

<400> SEQUENCE: 40
gtttcaggat catacgctgg agatcctcaa cag                                33

<210> SEQ ID NO 41
<211> LENGTH: 33
<212> TYPE: DNA
<213> ORGANISM: Artificial Sequence
<220> FEATURE:
<223> OTHER INFORMATION: Synthetic: R primer for CyPPO10_V165S

<400> SEQUENCE: 41
tccagcgtat gatcctgaaa caaatggtgc cac                                33

<210> SEQ ID NO 42
<211> LENGTH: 30
<212> TYPE: DNA
```

```
<213> ORGANISM: Artificial Sequence
<220> FEATURE:
<223> OTHER INFORMATION: Synthetic: F primer for CyPPO10_V305T

<400> SEQUENCE: 42
ccttatccaa ctactgcttg tgttgtgctt                                    30

<210> SEQ ID NO 43
<211> LENGTH: 30
<212> TYPE: DNA
<213> ORGANISM: Artificial Sequence
<220> FEATURE:
<223> OTHER INFORMATION: Synthetic: R primer for CyPPO10_V305T

<400> SEQUENCE: 43
cacaacacaa gcagtagttg gataaggtat                                    30

<210> SEQ ID NO 44
<211> LENGTH: 33
<212> TYPE: DNA
<213> ORGANISM: Artificial Sequence
<220> FEATURE:
<223> OTHER INFORMATION: Synthetic: F primer for CyPPO10_S60T

<400> SEQUENCE: 44
ggtccaaaca ctttcgctcc tactccagca ctc                                33

<210> SEQ ID NO 45
<211> LENGTH: 33
<212> TYPE: DNA
<213> ORGANISM: Artificial Sequence
<220> FEATURE:
<223> OTHER INFORMATION: Synthetic: R primer for CyPPO10_S60T

<400> SEQUENCE: 45
aggagcgaaa gtgtttggac caagctccca cac                                33

<210> SEQ ID NO 46
<211> LENGTH: 33
<212> TYPE: DNA
<213> ORGANISM: Artificial Sequence
<220> FEATURE:
<223> OTHER INFORMATION: Synthetic: F primer for CyPPO10_I340T

<400> SEQUENCE: 46
ctcggaacca cctggtcttc atgcttattc cca                                33

<210> SEQ ID NO 47
<211> LENGTH: 33
<212> TYPE: DNA
<213> ORGANISM: Artificial Sequence
<220> FEATURE:
<223> OTHER INFORMATION: Synthetic: R primer for CyPPO10_I340T

<400> SEQUENCE: 47
tgaagaccag gtggttccga gtgtccttat acc                                33

<210> SEQ ID NO 48
<211> LENGTH: 30
<212> TYPE: DNA
<213> ORGANISM: Artificial Sequence
<220> FEATURE:
<223> OTHER INFORMATION: Synthetic: F primer for CyPPO10_R89L

<400> SEQUENCE: 48
caccttccac tttatatata ctggaggga                                     30
```

<210> SEQ ID NO 49
<211> LENGTH: 30
<212> TYPE: DNA
<213> ORGANISM: Artificial Sequence
<220> FEATURE:
<223> OTHER INFORMATION: Synthetic: R primer for CyPPO10_R89L

<400> SEQUENCE: 49
gtatatataa agtggaaggt gcctatctcc                               30

<210> SEQ ID NO 50
<211> LENGTH: 30
<212> TYPE: DNA
<213> ORGANISM: Artificial Sequence
<220> FEATURE:
<223> OTHER INFORMATION: Synthetic: F primer for CyPPO10_R89V

<400> SEQUENCE: 50
caccttccag tttatatata ctggagggga                               30

<210> SEQ ID NO 51
<211> LENGTH: 30
<212> TYPE: DNA
<213> ORGANISM: Artificial Sequence
<220> FEATURE:
<223> OTHER INFORMATION: Synthetic: R primer for CyPPO10_R89V

<400> SEQUENCE: 51
gtatatataa actggaaggt gcctatctcc                               30

<210> SEQ ID NO 52
<211> LENGTH: 33
<212> TYPE: DNA
<213> ORGANISM: Artificial Sequence
<220> FEATURE:
<223> OTHER INFORMATION: Synthetic: F primer for CyPPO10_F161A

<400> SEQUENCE: 52
agattggtgg caccagcagt ttcaggagtg tac                           33

<210> SEQ ID NO 53
<211> LENGTH: 33
<212> TYPE: DNA
<213> ORGANISM: Artificial Sequence
<220> FEATURE:
<223> OTHER INFORMATION: Synthetic: R primer for CyPPO10_F161A

<400> SEQUENCE: 53
gtacactcct gaaactgctg gtgccaccaa tct                           33

<210> SEQ ID NO 54
<211> LENGTH: 33
<212> TYPE: DNA
<213> ORGANISM: Artificial Sequence
<220> FEATURE:
<223> OTHER INFORMATION: Synthetic: F primer for CyPPO10_V165C

<400> SEQUENCE: 54
ccatttgttt caggatgcta cgctggagat cct                           33

<210> SEQ ID NO 55
<211> LENGTH: 33
<212> TYPE: DNA
<213> ORGANISM: Artificial Sequence
<220> FEATURE:

```
<223> OTHER INFORMATION: Synthetic: R primer for CyPPO10_V165C

<400> SEQUENCE: 55
aggatctcca gcgtagcatc ctgaaacaaa tgg                                 33

<210> SEQ ID NO 56
<211> LENGTH: 33
<212> TYPE: DNA
<213> ORGANISM: Artificial Sequence
<220> FEATURE:
<223> OTHER INFORMATION: Synthetic: F primer for CyPPO10_Q184G

<400> SEQUENCE: 56
tttagaagga ttgctggact tgagaagttg gga                                 33

<210> SEQ ID NO 57
<211> LENGTH: 33
<212> TYPE: DNA
<213> ORGANISM: Artificial Sequence
<220> FEATURE:
<223> OTHER INFORMATION: Synthetic: R primer for CyPPO10_Q184G

<400> SEQUENCE: 57
tcccaacttc tcaagtccag caatccttct aaa                                 33

<210> SEQ ID NO 58
<211> LENGTH: 33
<212> TYPE: DNA
<213> ORGANISM: Artificial Sequence
<220> FEATURE:
<223> OTHER INFORMATION: Synthetic: F primer for CyPPO10_F324V

<400> SEQUENCE: 58
tcagttagac ctggagttgg tgttttggtg cct                                 33

<210> SEQ ID NO 59
<211> LENGTH: 33
<212> TYPE: DNA
<213> ORGANISM: Artificial Sequence
<220> FEATURE:
<223> OTHER INFORMATION: Synthetic: R primer for CyPPO10_F324V

<400> SEQUENCE: 59
aggcaccaaa acaccaactc caggtctaac tga                                 33

<210> SEQ ID NO 60
<211> LENGTH: 33
<212> TYPE: DNA
<213> ORGANISM: Artificial Sequence
<220> FEATURE:
<223> OTHER INFORMATION: Synthetic: F primer for CyPPO10_L327T

<400> SEQUENCE: 60
cctggatttg gtgttaccgt gcctagagga caa                                 33

<210> SEQ ID NO 61
<211> LENGTH: 33
<212> TYPE: DNA
<213> ORGANISM: Artificial Sequence
<220> FEATURE:
<223> OTHER INFORMATION: Synthetic: R primer for CyPPO10_L327T

<400> SEQUENCE: 61
ttgtcctcta ggcacggtaa caccaaatcc agg                                 33
```

<210> SEQ ID NO 62
<211> LENGTH: 30
<212> TYPE: DNA
<213> ORGANISM: Artificial Sequence
<220> FEATURE:
<223> OTHER INFORMATION: Synthetic: F primer for CyPPO10_A167I

<400> SEQUENCE: 62
tcaggagtgt acattggaga tcctcaacag          30

<210> SEQ ID NO 63
<211> LENGTH: 30
<212> TYPE: DNA
<213> ORGANISM: Artificial Sequence
<220> FEATURE:
<223> OTHER INFORMATION: Synthetic: R primer for CyPPO10_A167I

<400> SEQUENCE: 63
ttgaggatct ccaatgtaca ctcctgaaac          30

<210> SEQ ID NO 64
<211> LENGTH: 33
<212> TYPE: DNA
<213> ORGANISM: Artificial Sequence
<220> FEATURE:
<223> OTHER INFORMATION: Synthetic: F primer for CyPPO10_I408R

<400> SEQUENCE: 64
agaagggctc gtccacaata tatcgttggt tac          33

<210> SEQ ID NO 65
<211> LENGTH: 30
<212> TYPE: DNA
<213> ORGANISM: Artificial Sequence
<220> FEATURE:
<223> OTHER INFORMATION: Synthetic: R primer for CyPPO10_I408R

<400> SEQUENCE: 65
tattgtggac gagcccttct ccaaaccttc          30

<210> SEQ ID NO 66
<211> LENGTH: 36
<212> TYPE: DNA
<213> ORGANISM: Artificial Sequence
<220> FEATURE:
<223> OTHER INFORMATION: Synthetic: F primer for CyPPO10_I408W

<400> SEQUENCE: 66
ggtttggaga agggcttggc cacaatatat cgttgg          36

<210> SEQ ID NO 67
<211> LENGTH: 36
<212> TYPE: DNA
<213> ORGANISM: Artificial Sequence
<220> FEATURE:
<223> OTHER INFORMATION: Synthetic: R primer for CyPPO10_I408W

<400> SEQUENCE: 67
ccaacgatat attgtggcca gcccttctc caaacc          36

<210> SEQ ID NO 68
<211> LENGTH: 30
<212> TYPE: DNA
<213> ORGANISM: Artificial Sequence
<220> FEATURE:
<223> OTHER INFORMATION: Synthetic: F primer for CyPPO13_F373M

<400> SEQUENCE: 68
tcatttctca gtatgttagg aggtgctaca                                   30

<210> SEQ ID NO 69
<211> LENGTH: 30
<212> TYPE: DNA
<213> ORGANISM: Artificial Sequence
<220> FEATURE:
<223> OTHER INFORMATION: Synthetic: R primer for CyPPO13_F373M

<400> SEQUENCE: 69
agcacctcct aacatactga gaaatgagtg                                   30

<210> SEQ ID NO 70
<211> LENGTH: 30
<212> TYPE: DNA
<213> ORGANISM: Artificial Sequence
<220> FEATURE:
<223> OTHER INFORMATION: Synthetic: F primer for CyPPO13_F373V

<400> SEQUENCE: 70
tcatttctca gtgttttagg aggtgctaca                                   30

<210> SEQ ID NO 71
<211> LENGTH: 30
<212> TYPE: DNA
<213> ORGANISM: Artificial Sequence
<220> FEATURE:
<223> OTHER INFORMATION: Synthetic: R primer for CyPPO13_F373V

<400> SEQUENCE: 71
agcacctcct aaaacactga gaaatgagtg                                   30

<210> SEQ ID NO 72
<211> LENGTH: 30
<212> TYPE: DNA
<213> ORGANISM: Artificial Sequence
<220> FEATURE:
<223> OTHER INFORMATION: Synthetic: F primer for CyPPO13_F373I

<400> SEQUENCE: 72
tcatttctca gtattttagg aggtgctaca                                   30

<210> SEQ ID NO 73
<211> LENGTH: 30
<212> TYPE: DNA
<213> ORGANISM: Artificial Sequence
<220> FEATURE:
<223> OTHER INFORMATION: Synthetic: R primer for CyPPO13_F373I

<400> SEQUENCE: 73
agcacctcct aaaatactga gaaatgagtg                                   30

<210> SEQ ID NO 74
<211> LENGTH: 30
<212> TYPE: DNA
<213> ORGANISM: Artificial Sequence
<220> FEATURE:
<223> OTHER INFORMATION: Synthetic: F primer for CyPPO13_F373T

<400> SEQUENCE: 74
tcatttctca gtactttagg aggtgctaca                                   30

<210> SEQ ID NO 75
<211> LENGTH: 30

```
<212> TYPE: DNA
<213> ORGANISM: Artificial Sequence
<220> FEATURE:
<223> OTHER INFORMATION: Synthetic: R primer for CyPPO13_F373T

<400> SEQUENCE: 75
agcacctcct aaagtactga gaaatgagtg                                           30

<210> SEQ ID NO 76
<211> LENGTH: 30
<212> TYPE: DNA
<213> ORGANISM: Artificial Sequence
<220> FEATURE:
<223> OTHER INFORMATION: Synthetic: F primer for CyPPO13_F373L

<400> SEQUENCE: 76
tcatttctca gtcttttagg aggtgctaca                                           30

<210> SEQ ID NO 77
<211> LENGTH: 30
<212> TYPE: DNA
<213> ORGANISM: Artificial Sequence
<220> FEATURE:
<223> OTHER INFORMATION: Synthetic: R primer for CyPPO13_F373L

<400> SEQUENCE: 77
agcacctcct aaaagactga gaaatgagtg                                           30

<210> SEQ ID NO 78
<211> LENGTH: 30
<212> TYPE: DNA
<213> ORGANISM: Artificial Sequence
<220> FEATURE:
<223> OTHER INFORMATION: Synthetic: F primer for CyPPO13_F373C

<400> SEQUENCE: 78
tcatttctca gttgtttagg aggtgctaca                                           30

<210> SEQ ID NO 79
<211> LENGTH: 30
<212> TYPE: DNA
<213> ORGANISM: Artificial Sequence
<220> FEATURE:
<223> OTHER INFORMATION: Synthetic: R primer for CyPPO13_F373C

<400> SEQUENCE: 79
agcacctcct aaacaactga gaaatgagtg                                           30

<210> SEQ ID NO 80
<211> LENGTH: 32
<212> TYPE: DNA
<213> ORGANISM: Artificial Sequence
<220> FEATURE:
<223> OTHER INFORMATION: Synthetic: F primer for CyPPO13_R101A

<400> SEQUENCE: 80
aagttgccag catatatcta ctgggagggt gc                                        32

<210> SEQ ID NO 81
<211> LENGTH: 32
<212> TYPE: DNA
<213> ORGANISM: Artificial Sequence
<220> FEATURE:
<223> OTHER INFORMATION: Synthetic: R primer for CyPPO13_R101A

<400> SEQUENCE: 81
```
agtagatata tgctggcaac tttgcatcag cc          32

<210> SEQ ID NO 82
<211> LENGTH: 30
<212> TYPE: DNA
<213> ORGANISM: Artificial Sequence
<220> FEATURE:
<223> OTHER INFORMATION: Synthetic: F primer for CyPPO13_A177C

<400> SEQUENCE: 82
tcaggagttt attgtggaga tcctgatcaa          30

<210> SEQ ID NO 83
<211> LENGTH: 30
<212> TYPE: DNA
<213> ORGANISM: Artificial Sequence
<220> FEATURE:
<223> OTHER INFORMATION: Synthetic: R primer for CyPPO13_A177C

<400> SEQUENCE: 83
atcaggatct ccacaataaa ctcctgatgt          30

<210> SEQ ID NO 84
<211> LENGTH: 30
<212> TYPE: DNA
<213> ORGANISM: Artificial Sequence
<220> FEATURE:
<223> OTHER INFORMATION: Synthetic: F primer for CyPPO13_A177L

<400> SEQUENCE: 84
tcaggagttt atcttggaga tcctgatcaa          30

<210> SEQ ID NO 85
<211> LENGTH: 30
<212> TYPE: DNA
<213> ORGANISM: Artificial Sequence
<220> FEATURE:
<223> OTHER INFORMATION: Synthetic: R primer for CyPPO13_A177L

<400> SEQUENCE: 85
atcaggatct ccaagataaa ctcctgatgt          30

<210> SEQ ID NO 86
<211> LENGTH: 32
<212> TYPE: DNA
<213> ORGANISM: Artificial Sequence
<220> FEATURE:
<223> OTHER INFORMATION: Synthetic: F primer for CyPPO13_A177I

<400> SEQUENCE: 86
ggagtttata ttggagatcc tgatcaactt ag          32

<210> SEQ ID NO 87
<211> LENGTH: 32
<212> TYPE: DNA
<213> ORGANISM: Artificial Sequence
<220> FEATURE:
<223> OTHER INFORMATION: Synthetic: R primer for CyPPO13_A177I

<400> SEQUENCE: 87
aggatctcca atataaactc ctgatgtgaa ag          32

<210> SEQ ID NO 88
<211> LENGTH: 30
<212> TYPE: DNA
<213> ORGANISM: Artificial Sequence
<220> FEATURE:
<223> OTHER INFORMATION: Synthetic: F primer for CyPPO13_P316L+V318L

<400> SEQUENCE: 88
atactctatc ttcctcttgc tgttgtggct                               30

<210> SEQ ID NO 89
<211> LENGTH: 30
<212> TYPE: DNA
<213> ORGANISM: Artificial Sequence
<220> FEATURE:
<223> OTHER INFORMATION: Synthetic: R primer for CyPPO13_P316L+V318L

<400> SEQUENCE: 89
cacaacagca agaggaagat agagtatttc                               30

<210> SEQ ID NO 90
<211> LENGTH: 33
<212> TYPE: DNA
<213> ORGANISM: Artificial Sequence
<220> FEATURE:
<223> OTHER INFORMATION: Synthetic: F primer for CyPPO13_V318L

<400> SEQUENCE: 90
tatccacctc ttgctgttgt ggctcttgca tac                           33

<210> SEQ ID NO 91
<211> LENGTH: 32
<212> TYPE: DNA
<213> ORGANISM: Artificial Sequence
<220> FEATURE:
<223> OTHER INFORMATION: Synthetic: R primer for CyPPO13_V318L

<400> SEQUENCE: 91
caacagcaag aggtggatag agtatttctg cc                            32

<210> SEQ ID NO 92
<211> LENGTH: 30
<212> TYPE: DNA
<213> ORGANISM: Artificial Sequence
<220> FEATURE:
<223> OTHER INFORMATION: Synthetic: F primer for CyPPO13_V318M

<400> SEQUENCE: 92
ctctatccac ctatggctgt tgtggctctt                               30

<210> SEQ ID NO 93
<211> LENGTH: 30
<212> TYPE: DNA
<213> ORGANISM: Artificial Sequence
<220> FEATURE:
<223> OTHER INFORMATION: Synthetic: R primer for CyPPO13_V318M

<400> SEQUENCE: 93
agccacaaca gccataggtg gatagagtat                               30

<210> SEQ ID NO 94
<211> LENGTH: 30
<212> TYPE: DNA
<213> ORGANISM: Artificial Sequence
<220> FEATURE:
<223> OTHER INFORMATION: Synthetic: F primer for CyPPO13_P316A+V318L

<400> SEQUENCE: 94
atactctatg ctcctcttgc tgttgtggct                               30

<210> SEQ ID NO 95
<211> LENGTH: 30
<212> TYPE: DNA
<213> ORGANISM: Artificial Sequence
<220> FEATURE:
<223> OTHER INFORMATION: Synthetic: R primer for CyPPO13_P316A+V318L

<400> SEQUENCE: 95
cacaacagca gcaggaagat agagtatttc                                       30

<210> SEQ ID NO 96
<211> LENGTH: 32
<212> TYPE: DNA
<213> ORGANISM: Artificial Sequence
<220> FEATURE:
<223> OTHER INFORMATION: Synthetic: F primer for CyPPO13_F373N

<400> SEQUENCE: 96
tttctcagta acttaggagg tgctacagat gc                                    32

<210> SEQ ID NO 97
<211> LENGTH: 31
<212> TYPE: DNA
<213> ORGANISM: Artificial Sequence
<220> FEATURE:
<223> OTHER INFORMATION: Synthetic: R primer for CyPPO13_F373N

<400> SEQUENCE: 97
cctcctaagt tactgagaaa tgagtgataa c                                     31

<210> SEQ ID NO 98
<211> LENGTH: 32
<212> TYPE: DNA
<213> ORGANISM: Artificial Sequence
<220> FEATURE:
<223> OTHER INFORMATION: Synthetic: F primer for CyPPO13_F373H

<400> SEQUENCE: 98
tttctcagtc acttaggagg tgctacagat gc                                    32

<210> SEQ ID NO 99
<211> LENGTH: 31
<212> TYPE: DNA
<213> ORGANISM: Artificial Sequence
<220> FEATURE:
<223> OTHER INFORMATION: Synthetic: R primer for CyPPO13_F373H

<400> SEQUENCE: 99
cctcctaagt gactgagaaa tgagtgataa c                                     31

<210> SEQ ID NO 100
<211> LENGTH: 38
<212> TYPE: DNA
<213> ORGANISM: Artificial Sequence
<220> FEATURE:
<223> OTHER INFORMATION: Synthetic: F primer for CyPPO13_G194Q

<400> SEQUENCE: 100
gcttttccta gggtggctca gctcgaagag agatacgg                              38

<210> SEQ ID NO 101
<211> LENGTH: 38
<212> TYPE: DNA
<213> ORGANISM: Artificial Sequence
<220> FEATURE:
<223> OTHER INFORMATION: Synthetic: R primer for CyPPO13_G194Q

<400> SEQUENCE: 101
ccgtatctct cttcgagctg agccacccta ggaaaagc                38

<210> SEQ ID NO 102
<211> LENGTH: 38
<212> TYPE: DNA
<213> ORGANISM: Artificial Sequence
<220> FEATURE:
<223> OTHER INFORMATION: Synthetic: F primer for CyPPO13_G194K

<400> SEQUENCE: 102
gcttttccta gggtggctaa actcgaagag agatacgg                38

<210> SEQ ID NO 103
<211> LENGTH: 38
<212> TYPE: DNA
<213> ORGANISM: Artificial Sequence
<220> FEATURE:
<223> OTHER INFORMATION: Synthetic: R primer for CyPPO13_G194K

<400> SEQUENCE: 103
ccgtatctct cttcgagttt agccacccta ggaaaagc                38

<210> SEQ ID NO 104
<211> LENGTH: 38
<212> TYPE: DNA
<213> ORGANISM: Artificial Sequence
<220> FEATURE:
<223> OTHER INFORMATION: Synthetic: F primer for CyPPO13_G194R

<400> SEQUENCE: 104
gcttttccta gggtggctcg tctcgaagag agatacgg                38

<210> SEQ ID NO 105
<211> LENGTH: 38
<212> TYPE: DNA
<213> ORGANISM: Artificial Sequence
<220> FEATURE:
<223> OTHER INFORMATION: Synthetic: R primer for CyPPO13_G194R

<400> SEQUENCE: 105
ccgtatctct cttcgagacg agccacccta ggaaaagc                38

<210> SEQ ID NO 106
<211> LENGTH: 38
<212> TYPE: DNA
<213> ORGANISM: Artificial Sequence
<220> FEATURE:
<223> OTHER INFORMATION: Synthetic: F primer for CyPPO13_G194E

<400> SEQUENCE: 106
gcttttccta gggtggctga actcgaagag agatacgg                38

<210> SEQ ID NO 107
<211> LENGTH: 38
<212> TYPE: DNA
<213> ORGANISM: Artificial Sequence
<220> FEATURE:
<223> OTHER INFORMATION: Synthetic: R primer for CyPPO13_G194E

<400> SEQUENCE: 107
ccgtatctct cttcgagttc agccacccta ggaaaagc                38

<210> SEQ ID NO 108

<210> SEQ ID NO 108
<211> LENGTH: 38
<212> TYPE: DNA
<213> ORGANISM: Artificial Sequence
<220> FEATURE:
<223> OTHER INFORMATION: Synthetic: F primer for CyPPO13_G194M

<400> SEQUENCE: 108
gcttttccta gggtggctat gctcgaagag agatacgg        38

<210> SEQ ID NO 109
<211> LENGTH: 38
<212> TYPE: DNA
<213> ORGANISM: Artificial Sequence
<220> FEATURE:
<223> OTHER INFORMATION: Synthetic: R primer for CyPPO13_G194M

<400> SEQUENCE: 109
ccgtatctct cttcgagcat agccacccta ggaaaagc        38

<210> SEQ ID NO 110
<211> LENGTH: 32
<212> TYPE: DNA
<213> ORGANISM: Artificial Sequence
<220> FEATURE:
<223> OTHER INFORMATION: Synthetic: F primer for CyPPO13_F337V

<400> SEQUENCE: 110
cagccattaa gaggagtggg tcatctcatc cc        32

<210> SEQ ID NO 111
<211> LENGTH: 32
<212> TYPE: DNA
<213> ORGANISM: Artificial Sequence
<220> FEATURE:
<223> OTHER INFORMATION: Synthetic: R primer for CyPPO13_F337V

<400> SEQUENCE: 111
gggatgagat gacccactcc tcttaatggc tg        32

<210> SEQ ID NO 112
<211> LENGTH: 33
<212> TYPE: DNA
<213> ORGANISM: Artificial Sequence
<220> FEATURE:
<223> OTHER INFORMATION: Synthetic: F primer for CyPPO13_L340T

<400> SEQUENCE: 112
gaggatttgg tcataccatc cctaggtctc aag        33

<210> SEQ ID NO 113
<211> LENGTH: 33
<212> TYPE: DNA
<213> ORGANISM: Artificial Sequence
<220> FEATURE:
<223> OTHER INFORMATION: Synthetic: R primer for CyPPO13_L340T

<400> SEQUENCE: 113
cttgagacct agggatggta tgaccaaatc ctc        33

<210> SEQ ID NO 114
<211> LENGTH: 32
<212> TYPE: DNA
<213> ORGANISM: Artificial Sequence
<220> FEATURE:
<223> OTHER INFORMATION: Synthetic: F primer for CyPPO13_I353T

<400> SEQUENCE: 114
gaaccttggg tactacctgg gcttcatgtt tg								32

<210> SEQ ID NO 115
<211> LENGTH: 32
<212> TYPE: DNA
<213> ORGANISM: Artificial Sequence
<220> FEATURE:
<223> OTHER INFORMATION: Synthetic: R primer for CyPPO13_I353T

<400> SEQUENCE: 115
caaacatgaa gcccaggtag tacccaaggt tc								32

<210> SEQ ID NO 116
<211> LENGTH: 33
<212> TYPE: DNA
<213> ORGANISM: Artificial Sequence
<220> FEATURE:
<223> OTHER INFORMATION: Synthetic: F primer for CyPPO13_F171A

<400> SEQUENCE: 116
agattggtgg agcctgctac atcaggagtt tat								33

<210> SEQ ID NO 117
<211> LENGTH: 33
<212> TYPE: DNA
<213> ORGANISM: Artificial Sequence
<220> FEATURE:
<223> OTHER INFORMATION: Synthetic: R primer for CyPPO13_F171A

<400> SEQUENCE: 117
ataaactcct gatgtagcag gctccaccaa tct								33

<210> SEQ ID NO 118
<211> LENGTH: 33
<212> TYPE: DNA
<213> ORGANISM: Artificial Sequence
<220> FEATURE:
<223> OTHER INFORMATION: Synthetic: F primer for CyPPO13_R101A

<400> SEQUENCE: 118
gatgcaaagt tgccagctta tatctactgg gag								33

<210> SEQ ID NO 119
<211> LENGTH: 33
<212> TYPE: DNA
<213> ORGANISM: Artificial Sequence
<220> FEATURE:
<223> OTHER INFORMATION: Synthetic: R primer for CyPPO13_R101A

<400> SEQUENCE: 119
ctcccagtag atataagctg gcaactttgc atc								33

<210> SEQ ID NO 120
<211> LENGTH: 33
<212> TYPE: DNA
<213> ORGANISM: Artificial Sequence
<220> FEATURE:
<223> OTHER INFORMATION: Synthetic: F primer for CyPPO13_V175C

<400> SEQUENCE: 120
cctttcacat caggatgtta tgctggagat cct								33

<210> SEQ ID NO 121
<211> LENGTH: 33
<212> TYPE: DNA

```
<213> ORGANISM: Artificial Sequence
<220> FEATURE:
<223> OTHER INFORMATION: Synthetic: R primer for CyPPO13_V175C

<400> SEQUENCE: 121
aggatctcca gcataacatc ctgatgtgaa agg                                    33

<210> SEQ ID NO 122
<211> LENGTH: 31
<212> TYPE: DNA
<213> ORGANISM: Artificial Sequence
<220> FEATURE:
<223> OTHER INFORMATION: Synthetic: F primer for CyPPO13_V175L

<400> SEQUENCE: 122
acatcaggat tgtatgctgg agatcctgat c                                     31

<210> SEQ ID NO 123
<211> LENGTH: 33
<212> TYPE: DNA
<213> ORGANISM: Artificial Sequence
<220> FEATURE:
<223> OTHER INFORMATION: Synthetic: R primer for CyPPO13_V175L

<400> SEQUENCE: 123
tccagcatac aatcctgatg tgaaaggctc cac                                    33

<210> SEQ ID NO 124
<211> LENGTH: 20
<212> TYPE: DNA
<213> ORGANISM: Artificial Sequence
<220> FEATURE:
<223> OTHER INFORMATION: Synthetic: Forward primer for bar probe

<400> SEQUENCE: 124
ttccgtaccg agccgcagga                                                   20

<210> SEQ ID NO 125
<211> LENGTH: 20
<212> TYPE: DNA
<213> ORGANISM: Artificial Sequence
<220> FEATURE:
<223> OTHER INFORMATION: Synthetic: Reverse primer for bar probe

<400> SEQUENCE: 125
cgttgggcag cccgatgaca                                                   20

<210> SEQ ID NO 126
<211> LENGTH: 32
<212> TYPE: DNA
<213> ORGANISM: Artificial Sequence
<220> FEATURE:
<223> OTHER INFORMATION: Synthetic: Restriction site of CyPPO10_BamHIF

<400> SEQUENCE: 126
ccccggatcc atgattgaag tggatgtggc ta                                     32

<210> SEQ ID NO 127
<211> LENGTH: 33
<212> TYPE: DNA
<213> ORGANISM: Artificial Sequence
<220> FEATURE:
<223> OTHER INFORMATION: Synthetic: Restriction site of CyPPO10_XhoIR

<400> SEQUENCE: 127
cccnctcgag tgattgtcca ccagcgaggt aag                                    33
```

<210> SEQ ID NO 128
<211> LENGTH: 32
<212> TYPE: DNA
<213> ORGANISM: Artificial Sequence
<220> FEATURE:
<223> OTHER INFORMATION: Synthetic: Restriction site of CyPPO13_BamHIF

<400> SEQUENCE: 128
ccccggatcc atgaaccctg ctacccctga ac                                 32

<210> SEQ ID NO 129
<211> LENGTH: 33
<212> TYPE: DNA
<213> ORGANISM: Artificial Sequence
<220> FEATURE:
<223> OTHER INFORMATION: Synthetic: Restriction site of CyPPO13_XhoIR

<400> SEQUENCE: 129 cccccctcgag cacctgtgat aacaactgct gag                               33

<210> SEQ ID NO 130
<211> LENGTH: 1404
<212> TYPE: DNA
<213> ORGANISM: Artificial Sequence
<220> FEATURE:
<223> OTHER INFORMATION: Synthetic: nucleic acid sequence of CyPPO10m-6

<400> SEQUENCE: 130
atgattgaag tggatgtggc tattgttggt ggtggtctta gtggattgtc agtggcttgg     60
agattacaga ggagtgctcc tcattattct ggagttcttc ttgaggcttc tgatagactt    120
ggaggtaata tcactacaca agctgctgaa ggatttgtgt gggagcttgg tccaaacagt    180
ttcgctccta ctccagcact cttacagttg attgctgaag ttggactcca ttctgagtta    240
atcagaggag ataggcacct tccaagatat atatactgga ggggagaact ttatcctttg    300
gagccaacta ggcctcttgc tttggcaaca tcaaatcttt tgagtccttg ggaaaggtt     360 agagctgcac tcggagcttt aggttttgtg cctccatatc ttggatctgg agatgaaagt    420
gttgattctt tctttagaag gcatcttgga caagaagttg ctgagagatt ggtggcacca    480
tttgtttcag gagtgtacgc tggagatcct caacagcttt ctgctgctgc tgcttttaga    540
aggattgctc aacttgagaa gttgggaggt tcattgatcg ctggagcact cagattaaga    600
aggcaacagc ctccacagcc aaaacctcca gctcaagtgc agatgagacc tggagaactc    660
ggtagtttta gggggggtct cgctgcatta cctagagcca tcgcacaaca gttgaaggca    720
ccacttcatt tgcaaacacc tgttgaagct attacccctg agccaaaagg aagttatctc    780
ttaaggagtg gtgaactgac ttggcacgct agatcagttg tgttggctac tccagcatac    840
caaactgctg aacttgttgc accattccag cctgctatcg ctagagcttt ggctaccata    900
ccttatccaa ctgttgcttg tgttgtgctt gcttaccctg ctggattggg tagatcagtt    960
agacctggat ttggtgtttt ggtgcctaga ggacaaggta taaggatact cggaaccatt   1020
tggtcttcat gcttattccc acaaaggact cctgctggtt ggcaggcttt tacctctatg   1080
ataggaggtg atactgatcc tgatcttgca tcattgagag aagaggccat tgttgaacaa   1140
gtgcaacagg atctcacaag gcttcttgat cttcctgctg caaaggcaag actcttgggt   1200
atgaaggttt ggagaggggc tattccacaa tatatcgttg gttaccctca acagaggcaa   1260
caggtgacac acgctcttac ccagactcct ggtctcttct tatgttcaaa ctacgcagag   1320

```
ggagttgcat tggggatag agtggaacac ggaaatagga ctgctgctgc tgtggctgct    1380
tacctcgctg gtggacaatc atga                                          1404
```

<210> SEQ ID NO 131
<211> LENGTH: 467
<212> TYPE: PRT
<213> ORGANISM: Artificial Sequence
<220> FEATURE:
<223> OTHER INFORMATION: Synthetic: CyPPO10m-6

<400> SEQUENCE: 131

```
Met Ile Glu Val Asp Val Ala Ile Val Gly Gly Gly Leu Ser Gly Leu
1               5                   10                  15

Ser Val Ala Trp Arg Leu Gln Arg Ser Ala Pro His Tyr Ser Gly Val
            20                  25                  30

Leu Leu Glu Ala Ser Asp Arg Leu Gly Gly Asn Ile Thr Thr Gln Ala
        35                  40                  45

Ala Glu Gly Phe Val Trp Glu Leu Gly Pro Asn Ser Phe Ala Pro Thr
    50                  55                  60

Pro Ala Leu Leu Gln Leu Ile Ala Glu Val Gly Leu His Ser Glu Leu
65                  70                  75                  80

Ile Arg Gly Asp Arg His Leu Pro Arg Tyr Ile Tyr Trp Arg Gly Glu
                85                  90                  95

Leu Tyr Pro Leu Glu Pro Thr Arg Pro Leu Ala Leu Ala Thr Ser Asn
            100                 105                 110

Leu Leu Ser Pro Trp Gly Lys Val Arg Ala Ala Leu Gly Ala Leu Gly
        115                 120                 125

Phe Val Pro Pro Tyr Leu Gly Ser Gly Asp Glu Ser Val Asp Ser Phe
    130                 135                 140

Phe Arg Arg His Leu Gly Gln Glu Val Ala Glu Arg Leu Val Ala Pro
145                 150                 155                 160

Phe Val Ser Gly Val Tyr Ala Gly Asp Pro Gln Gln Leu Ser Ala Ala
                165                 170                 175

Ala Ala Phe Arg Arg Ile Ala Gln Leu Glu Lys Leu Gly Gly Ser Leu
            180                 185                 190

Ile Ala Gly Ala Leu Arg Leu Arg Arg Gln Gln Pro Gln Pro Lys
        195                 200                 205

Pro Pro Ala Gln Val Gln Met Arg Pro Gly Glu Leu Gly Ser Phe Arg
    210                 215                 220

Gly Gly Leu Ala Ala Leu Pro Arg Ala Ile Ala Gln Gln Leu Lys Ala
225                 230                 235                 240

Pro Leu His Leu Gln Thr Pro Val Glu Ala Ile Thr Pro Glu Pro Lys
                245                 250                 255

Gly Ser Tyr Leu Leu Arg Ser Gly Glu Leu Thr Trp His Ala Arg Ser
            260                 265                 270

Val Val Leu Ala Thr Pro Ala Tyr Gln Thr Ala Glu Leu Val Ala Pro
        275                 280                 285

Phe Gln Pro Ala Ile Ala Arg Ala Leu Ala Thr Ile Pro Tyr Pro Thr
    290                 295                 300

Val Ala Cys Val Val Leu Ala Tyr Pro Ala Gly Leu Gly Arg Ser Val
305                 310                 315                 320

Arg Pro Gly Phe Gly Val Leu Val Pro Arg Gly Gln Gly Ile Arg Ile
                325                 330                 335

Leu Gly Thr Ile Trp Ser Ser Cys Leu Phe Pro Gln Arg Thr Pro Ala
            340                 345                 350
```

```
Gly Trp Gln Ala Phe Thr Ser Met Ile Gly Gly Asp Thr Asp Pro Asp
            355                 360                 365

Leu Ala Ser Leu Arg Glu Glu Ala Ile Val Glu Gln Val Gln Gln Asp
        370                 375                 380

Leu Thr Arg Leu Leu Asp Leu Pro Ala Ala Lys Ala Arg Leu Leu Gly
385                     390                 395                 400

Met Lys Val Trp Arg Gly Ala Ile Pro Gln Tyr Ile Val Gly Tyr Pro
                405                 410                 415

Gln Gln Arg Gln Gln Val Thr His Ala Leu Thr Gln Thr Pro Gly Leu
            420                 425                 430

Phe Leu Cys Ser Asn Tyr Ala Glu Gly Val Ala Leu Gly Asp Arg Val
        435                 440                 445

Glu His Gly Asn Arg Thr Ala Ala Ala Val Ala Ala Tyr Leu Ala Gly
    450                 455                 460

Gly Gln Ser
465
```